US007702464B1

(12) United States Patent
Emig et al.

(10) Patent No.: US 7,702,464 B1

(45) Date of Patent: Apr. 20, 2010

(54) METHOD AND APPARATUS FOR CODON DETERMINING

(75) Inventors: Robin A. Emig, Oakland, CA (US); Richard John Fox, Redwood City, CA (US); Claes Gustafsson, Belmont, CA (US); Sridhar Govindarajan, Redwood City, CA (US); Jeremy S. Minshull, Los Altos, CA (US); Guy Cavet, Seattle, WA (US)

(73) Assignee: Maxygen, Inc., Redwood City, CA (US)

(*) Notice: Subject to any disclaimer, the term of this patent is extended or adjusted under 35 U.S.C. 154(b) by 0 days.

(21) Appl. No.: 10/232,770

(22) Filed: Aug. 30, 2002

Related U.S. Application Data

(63) Continuation-in-part of application No. 10/225,564, filed on Aug. 20, 2002.

(60) Provisional application No. 60/392,511, filed on Jun. 27, 2002, provisional application No. 60/363,505, filed on Mar. 9, 2002, provisional application No. 60/339,886, filed on Nov. 1, 2001, provisional application No. 60/316,852, filed on Aug. 31, 2001, provisional application No. 60/314,131, filed on Aug. 21, 2001.

(51) Int. Cl.
*G06F 19/00* (2006.01)
*C40B 50/00* (2006.01)
*C40B 50/02* (2006.01)

(52) U.S. Cl. ............................ 702/19; 702/20; 506/23; 506/24

(58) Field of Classification Search ................... 702/19, 702/20; 435/6

See application file for complete search history.

(56) References Cited

U.S. PATENT DOCUMENTS

| | | | |
|---|---|---|---|
| 4,959,312 A | 9/1990 | Sirotkin | |
| 5,043,272 A | 8/1991 | Hartly et al. | |
| 5,066,584 A | 11/1991 | Gyllenstein et al. | |
| 5,264,563 A | 11/1993 | Huse | |
| 5,506,793 A | 4/1996 | Straayer | |
| 5,521,077 A | 5/1996 | Khosla | |
| 5,789,577 A | 8/1998 | Geysen | |
| 5,824,469 A | 10/1998 | Horwitz | |
| 5,825,978 A | 10/1998 | Digalakis et al. | |
| 5,864,810 A | 1/1999 | Digalakis et al. | |
| 5,866,363 A | 2/1999 | Pieczenik | |
| 5,869,644 A | 2/1999 | Shortle et al. | |
| 6,001,574 A | 12/1999 | Short et al. | |
| 6,030,779 A | 2/2000 | Short | |
| 6,054,267 A | 4/2000 | Short | |
| 6,055,498 A | 4/2000 | Neumeyer et al. | |
| 6,096,548 A | 8/2000 | Stemmer | |
| 6,117,679 A | 9/2000 | Stemmer | |
| 6,132,970 A | 10/2000 | Stemmer | |
| 6,153,410 A | 11/2000 | Arnold et al. | |
| 6,159,690 A | 12/2000 | Borrebaeck et al. | |
| 6,188,965 B1 | 2/2001 | Mayo et al. | |
| 6,226,611 B1 | 5/2001 | Neumeyer et al. | |
| 6,256,607 B1 | 7/2001 | Digalakis et al. | |
| 6,269,312 B1 | 7/2001 | Mayo et al. | |
| 6,615,253 B1* | 9/2003 | Bowman-Amuah | 709/219 |
| 7,118,096 B2 | 10/2006 | Luo et al. | |
| 2007/0037214 A1* | 2/2007 | Luo et al. | 435/7.1 |

FOREIGN PATENT DOCUMENTS

| | | |
|---|---|---|
| WO | WO 90/00626 A1 | 1/1990 |
| WO | WO 92/06176 A1 | 4/1992 |
| WO | WO 00/00632 A1 | 1/2000 |
| WO | WO 00/23564 A2 | 4/2000 |
| WO | WO 00/42560 * | 7/2000 |
| WO | WO 00/47612 A2 | 8/2000 |

OTHER PUBLICATIONS

Moreria (Theoretical Computer Science (2004) vol. 322, pp. 297-312).*

Current Opinion in Chemical Biology (1999) vol. 3, pp. 284-290).*

Allawi et al. (1997) "Thermodynamics and NMR of internal G.T mismatches in DNA." Biochemistry, 36 10581-10594.

Arkin (1992) "An algorithm for protein engineering: Simulations of recursive ensemble mutagenesis." Proc Natl Acad Sci Aug. 15;89(16):7811-5.

Kayushin et al. (1996) "A convenient approach to the synthesis of trinucleotide phosphoroamidites-synthons for the generation of oligonucleotide/peptide libraries." Nucleic Acids Res. 24:3748-3755.

Moore et al. (2001) "Predicting crossover generation in DNA shuffling", PNAS, vol. 98, No. 6, pp. 3226-3231 (available at http://www.pnas.org/cgi/reprint/98/6/3226.pdf).

Santalucia (1998) "A unified view of polymer, dumbbell, and oligonucleotide DNA nearest-neighbor thermodynamics." PNAS, 95, 1460-1465.

Shao et al. (1998) "Random-priming in vitro recombination: an effective tool for directed evolution." Nucleic Acids Research 26(2):681-683.

(Continued)

*Primary Examiner*—Lori A Clow

(74) *Attorney, Agent, or Firm*—Weaver Austin Villeneuve & Sampson LLP; Norm Kruse

(57) ABSTRACT

Computer processing methods and/or systems for minimizing and/or optimizing data strings in accordance with rules and options. Minimized data strings can represent data sequences important in certain biologic analyses and/or syntheses. In specific embodiments, a request is generated by a user at a client system and received by a server system. The server system accesses initial data indicated or provided by the client system. The server system then performs an analysis to minimize the data needed for further reactions. In specific embodiments, a server can use proprietary methods or data at the server side while protecting those proprietary methods and data from access by the client system.

20 Claims, 26 Drawing Sheets

OTHER PUBLICATIONS

U.S. Appl. No. 09/618,579, filed Jul. 18, 2000 "Methods for Making Character Strings, Polynucleotides and Polypeptides Having Desired Characteristics" Inventors: Selifonov et al.

U.S. Appl. No. 10/225,564, filed Aug. 20, 2002 "Method and System Using Systematicaly Varied Data Libraries" Inventors: Claes Gustafsson et al.

U.S. Appl. No. 10/279,762, filed Oct. 23, 2002 "Method and Apparatus for Recombination Calculators" Inventors: Emily C. Mundorff, et al.

U.S. Appl. No. 10/607,817, filed Jun. 26, 2003 "Method and Apparatus for Sequence Backtranslating Using a Computer System" Inventors: Robin A. Emig, et al.

U.S. Appl. No. 60/284,407, filed Apr. 17, 2001, Peizhi Luo.

* cited by examiner

| Symbol | Meaning | Origin of designation |
|---|---|---|
| a | a | adenine |
| g | g | guanine |
| c | c | cytosine |
| t | t | thymine |
| u | u (generally RNA only) | uracil |
| ***r*** | g or a ***(here and below are ambiguous codes)*** | purine |
| ***y*** | t/u or c | pyrimidine |
| ***m*** | a or c | amino |
| ***k*** | g or t/u | keto |
| ***s*** | g or c | strong interactions 3H-bonds |
| ***w*** | a or t/u | weak interactions 2H-bonds |
| ***b*** | g or c or t/u not a | |
| ***d*** | a or g or t/u not c | |
| ***h*** | a or c or t/u not g | |
| ***v*** | a or g or c not t, not u | |
| ***n*** | a or g or c or t/u, | any |

*FIG. 1: NUCLEOTIDE BASE CODES (PRIOR ART)*

| names of the 20 common amino acids | 3 letter abbreviation | single letter codes |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

*FIG. 2: AMINO ACID CODES (PRIOR ART)*

| | U | | C | | A | | G | |
|---|---|---|---|---|---|---|---|---|
| U | UUU | Phe (F) | UCU | Ser (S) | UAU | Tyr (Y) | UGU | Cys(C) |
| | UUC | | UCC | | UAC | | UGC | |
| | UUA | Leu (L) | UCA | | UAA | STOP | UGA | STOP |
| | UUG | | UCG | | UAG | | UGG | Trp (W) |
| C | CUU | Leu (L) | CCU | Pro (P) | CAU | His (H) | CGU | Arg (R) |
| | CUC | | CCC | | CAC | | CGC | |
| | CUA | | CCA | | CAA | Gln (Q) | CGA | |
| | CUG | | CCG | | CAG | | CGG | |
| A | AUU | Ile (I) | ACU | Thr (T) | AAU | Asn (N) | AGU | Ser (S) |
| | AUC | | ACC | | AAC | | AGC | |
| | AUA | | ACA | | AAA | Lys (K) | AGA | Arg (R) |
| | AUG | Met (M) | ACG | | AAG | | AGG | |
| G | GUU | Val (V) | GCU | Ala (A) | GAU | Asp (D) | GGU | Gly (G) |
| | GUC | | GCC | | GAC | | GGC | |
| | GUA | | GCA | | GAA | Glu (E) | GGA | |
| | GUG | | GCG | | GAG | | GGG | |

*FIG. 3: COMMON TRIPLET CODONS (PRIOR ART) THOUGH OTHER CODES ARE POSSIBLE IN SOME ORGANISMS AND ORGANELLES*

| | File　　　　Options　　　　　Help |
|---|---|
| | (x) Select to indicate New Diversity |
| A | 　　　10　　　20　　　30　　　40　　　50　　↕<br>　　　　　　　　　C |

| | (x) Select to open Protein |
|---|---|
| B | 　　　　10 *b b*　20　　*v* 30　　　40　　　50　　↕<br>Pr1　T　W S G... D D <u>**N**</u>...S - A ***K*** H ***V*** R G ...　E<br>Pr2　T　W T G... D D T...S - A A H ***V*** R G ...　N<br>Pr3　T　W T G... D D T...S - A A H V R G ...　N |

| | ( ) Select to open DNA |
|---|---|
| C | ↕ |

| | ( ) Select to open Minimal Degenerate Codons |
|---|---|
| D | 　　　10　　　　　20　　　　30　　　　40　　　　50　↕<br>Pr1 AGT __ AGG ACT GGA AAT　TGC GGC ACT AAG TGT AGA TCA CAC TGT ...<br>Pr2　　　　TCT　　　　　　　GAC GAC __ CAG　... |

| | ( ) Select to open All Codons |
|---|---|
| E | ↕ |

| | ( ) Select to open Oligos |
|---|---|
| F | ↕ |

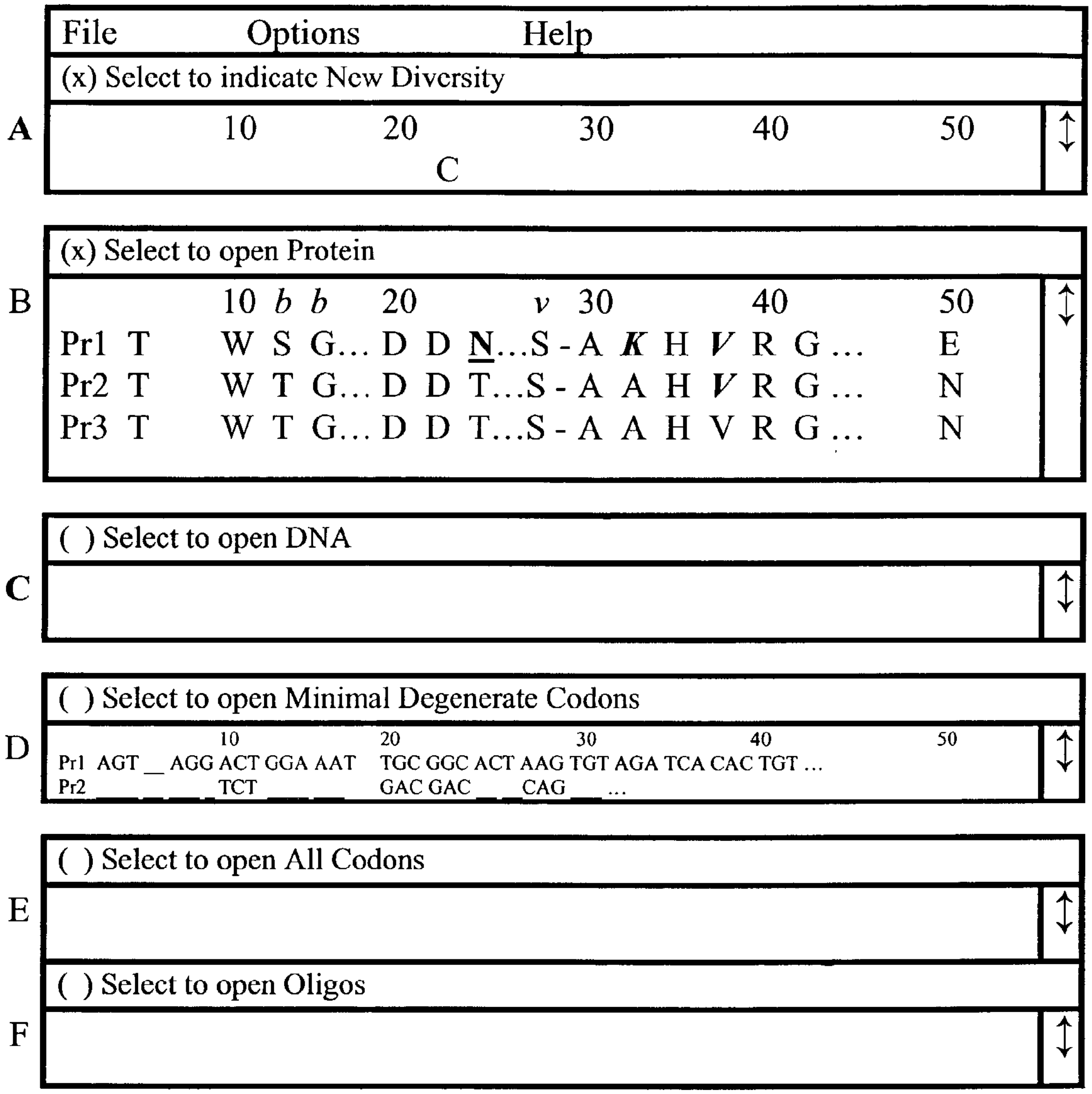

*FIG. 4*

End DNA

Custom
No HIS TAG-Sfil
HIS TAG-Sfil

| Options | Codon Bias Table | Processing |
|---|---|---|

Arabidopsis thaliana

Custom
Arabidopsis thaliana
Aspergillus nidulans
Bacillus subtilis
Escherichia coli
Homo sapiens
Klebsiella pneumoniae
Maize

```
Gln     CAG     231.00     21.27     0.53
Gln     CAA     202.00     18.60     0.47
His     CAT      96.00      8.84     0.40
His     CAC     144.00     13.26     0.60

Leu     CTG     106.00      9.76     0.11
Leu     CTA      91.00      8.38     0.09
Leu     CTT     257.00     23.67     0.26
Leu     CTC     203.00     18.69     0.21

Pro     CCG      85.00      7.83     0.16
Pro     CCA     174.00     16.02     0.33
Pro     CCT     177.00     16.30     0.34
Pro     CCC      84.00      7.74     0.16
```

| OK | Cancel |

| | |
|---|---|
| Sites to Change | 5-20,29-47,60 |

☐ All Sites

| | |
|---|---|
| Sites to Fix | 15,36-38,45 |
| Peptides | ACL, WER |
| Substitution Matrix | DARWIN100 ▼ |

Oligo Positioning

⦿ Manual (for spiking)   ○ Automatic (for total gene synthesis)

| | |
|---|---|
| Oligo Length | 30 |
| Oligo Offset | 5 |
| Oligo Direction | ⦿ Forward Oligos   ○ Reverse Oligos |

[ Scan ]  [ Cancel ]

```
PileUp
   MSF: 50    Type: P    Check: 3776 ..
Name: POLYPEP1  Len: 50 Check: 5160 Weight: 0
Name: POLYPEP2  Len: 50 Check: 4401 Weight: 0
Name: POLYPEP3  Len: 50 Check: 4215 Weight: 0
//
                                    1                                          50
POLYPEP1  ML------TW S...D DNKCRS--GA K...G KWKCFCYFNC
POLYPEP2  MLCE----TW T...C DTQCKS--GA A...G KWMCFCYFNC
POLYPEP3  MLCEKAS-TW T...C DTKCRSWEGA A...G KHMCFCYFNC
                                    1                                          50
POLYPEP1  ELCEKASRTW S...D DNKCRSWEGA K...G KWKCFCYFNC
POLYPEP2  NLCEKASLTW T...C DTQCKSWEGA A...G KWMCFCYFNC
POLYPEP3  NLCEKASLTW T...C DTKCRSWEGA A...G KHMCFCYFNC
```

FIG. 18

```
>BT_of_P10
ATG ACC AAC CAG CCG ACT GAG ATT GCG … ATT GTT GGA GGT GGA ATG GTG GGT GGC GCA CTC GCG CTG
GGC TTG GCA CAG CAC GGA TTC GCG GTG ACG GTG ATT GAG CAT GCT GAG CCA          GCC CCT …
>BT_of_P11
ATG CAC GCT GAT CTT GTG ATT GTT GGA GCT GGA ATG GTG GGT TCC GCA CTC GCG CTG GCC TTG GAA GGT
TCG GGA TTG GAG GTG TTG TTG GTT GAT GGT GGT TCT CTT GAT GTT GCC CCT TTT AAA CCA GAG …
>BT_of_P12
ATG CAC GCT GAT CTT GTG ATT GTT GGA GCT GGA ATG GTG GGT TCC GCA CTC GCG CTG GCC TTG GAA GGT
TCG GGA TTG GAG GTG TTG TTG GTT GAT GGT GGT TCT CTT GAT GTT GCC CCT TTT AAA CCA GAG …
>BT_of_P13
ATG ACC AAC CAG CCG ACT GAG ATT GCG ATT GTT GGA GGT GGA ATG GTG GGT GGC GCA CTC GCG CTG GGC
TTG GCA CAG CAC GGA TTC ACG GTG ACG GTG ATT GAG CAT GCT GAG CCA          GCC CCT TTT …
>BT_of_P14
ATG CAC GTT ATC CAG AAG GAT ATG ATC GTT GTT GGA GGT GGA ATG GTG GGT GCC GCA TGC GCG CTG GGC
TTG GGA AAG CAG GGA CAC CAG GTG CAG TTG ATT GAG CAT GCT CCT CTT          CCC CAG TTT …
>BT_of_P15
ATG ACC AAC CAG CCG ACT GAG ATT GCG ATT GTT GGA GGT GGA ATG GTG GGT GGC GCA CTC GCG CTG GGC
TTG GCA CAG CAC GGA TTC GCG GTG ACG GTG ATT GAG CAT GCT GAG CCA          GCC CCT TTT …
```

FIG. 19

```
- <Alloy>
- <com.maxygen.alloy.program.ProteinModel>
- <Sequence>
<Name />
<States>3333333333…333333333</States>
<Values>-----------…---------</Values>
<Links>-1-1-1-1-1-1-1-1-1-1-1…-1-1-1-1-1-1-1-1-1-1-1</Links>
</Sequence> - <Sequence>
<Name>TRANSLATION_OF_MD(LIB3ACT)P-1_G03_020.AB1</Name> …
<Name>TRANSLATION_OF_MD(LIB3ACT)P-1_G10_072.AB1</Name> …
<Values>MLCEKAS-TW…KHMCFCYFNC</Values>
</com.maxygen.alloy.program.ProteinModel>
- <com.maxygen.alloy.program.NewDiversityModel>
  <Length>101</Length>
  </com.maxygen.alloy.program.NewDiversityModel>
- <com.maxygen.alloy.program.AlloyOptionsModel>
  <AllowStopCodonsFromExtraDiversity>0</AllowStopCodonsFromExtraDiversity>
  <MaxDegeneracyInOligo>1</MaxDegeneracyInOligo>
  <MaxOligoLength>60</MaxOligoLength>
  <MinBaseOverlap>15</MinBaseOverlap>
  <MinOligoLength>24</MinOligoLength>
  <MinTmOverlap>0</MinTmOverlap>
  <NoDegenerateEndForBases>1</NoDegenerateEndForBases>
```

FIG. 19 CONTINUED

```
  <OligoOverlapStyle>1</OligoOverlapStyle>
  <Circularize>1</Circularize>
  <DnaStart />
  <DnaEnd />
- <com.maxygen.alloy.program.CodonBiasTableModel>
- <Data byteArray="1">
- <![CDATA[
QXJhYmlkb3BzaXMgdGhhbGlhbmEKCjMxIGdlbmVzIGZvdW5kIGluIEdlbkJhbmsgNjMuCgogUHJv
...
NApQcm8gICAgIENDQyAgICAgICA4NC4wMCAgICAgIDcuNzQgICAgICAwLjE2
  ]]>
  </Data>
  </com.maxygen.alloy.program.CodonBiasTableModel>
  <ExportText>oligonucleotide</ExportText>
  <Process>0</Process>
  <ServerUrl>http://localhost:8080/oedipus/servlet</ServerUrl>
  </com.maxygen.alloy.program.AlloyOptionsModel>
- <com.maxygen.alloy.program.AllCodonsModel>
- <Sequence>
<Values>ATGCAGA...   ... TATC</Values>
  </Sequence>
</com.maxygen.alloy.program.AllCodonsModel>
- <com.maxygen.alloy.program.DegenerateCodonsModel>
- <Sequence>
<Values>ATGCAGACCCTATCGATTCAACACGGGACCTTGGTCACAA_ACTGTGCTGAAGCAGTCCGCAGTGGTATC</Values>
  </Sequence>
  </com.maxygen.alloy.program.DegenerateCodonsModel>
- <com.maxygen.alloy.program.OligosModel>
- <Sequence>
<States>11111111111111111111111111111111111111111_11111111111111111111111111111</States>
<Values>ATGCAGACCCTAT_GTT_TATC</Values>
  </Sequence>
- <Sequence>
<States>000000000222222222222222222222222222222222222222222222222222222222222222222222
22222222222222222222222222222222222</States>
<Values>____________________________TGGAACCAGTGTTACCTGGTCATGGCAGCCCAGAACCCACTGTCAACCCATGTACA
AGTC______________________C_ ______________________CCATAG</Values>
  </Sequence>
  </com.maxygen.alloy.program.OligosModel>
- <com.maxygen.alloy.program.CustomCodonsModel>
  <SymbolList Position="0" />
- <SymbolList Position="1">
  <Codon>ATG</Codon>
  <Codon>---</Codon>
  </SymbolList>
- <SymbolList Position="2">
  <Codon>---</Codon>
  <Codon>CAA</Codon>
  <Codon>CAG</Codon>
  </SymbolList>
- <SymbolList Position="3">
  <Codon>ACG</Codon>
  <Codon>---</Codon>
  <Codon>ACC</Codon>
  <Codon>ACT</Codon>
  <Codon>ACA</Codon>
  </SymbolList>
-
- <SymbolList Position="119">
  <Codon>---</Codon>
  <Codon>GGG</Codon>
  <Codon>GGT</Codon>
  <Codon>GGA</Codon>
```

*FIG. 19 CONTINUED*

```
<Codon>GGC</Codon>
</SymbolList>
<SymbolList Position="120">
<Codon>ATT</Codon>
<Codon>---</Codon>
<Codon>ATC</Codon>
<Codon>ATA</Codon>
</SymbolList>
</com.maxygen.alloy.program.CustomCodonsModel>
<ModelHandle>986255320515</ModelHandle>
<ModelEvent method="submitData" selected="1" />
</Alloy>
```

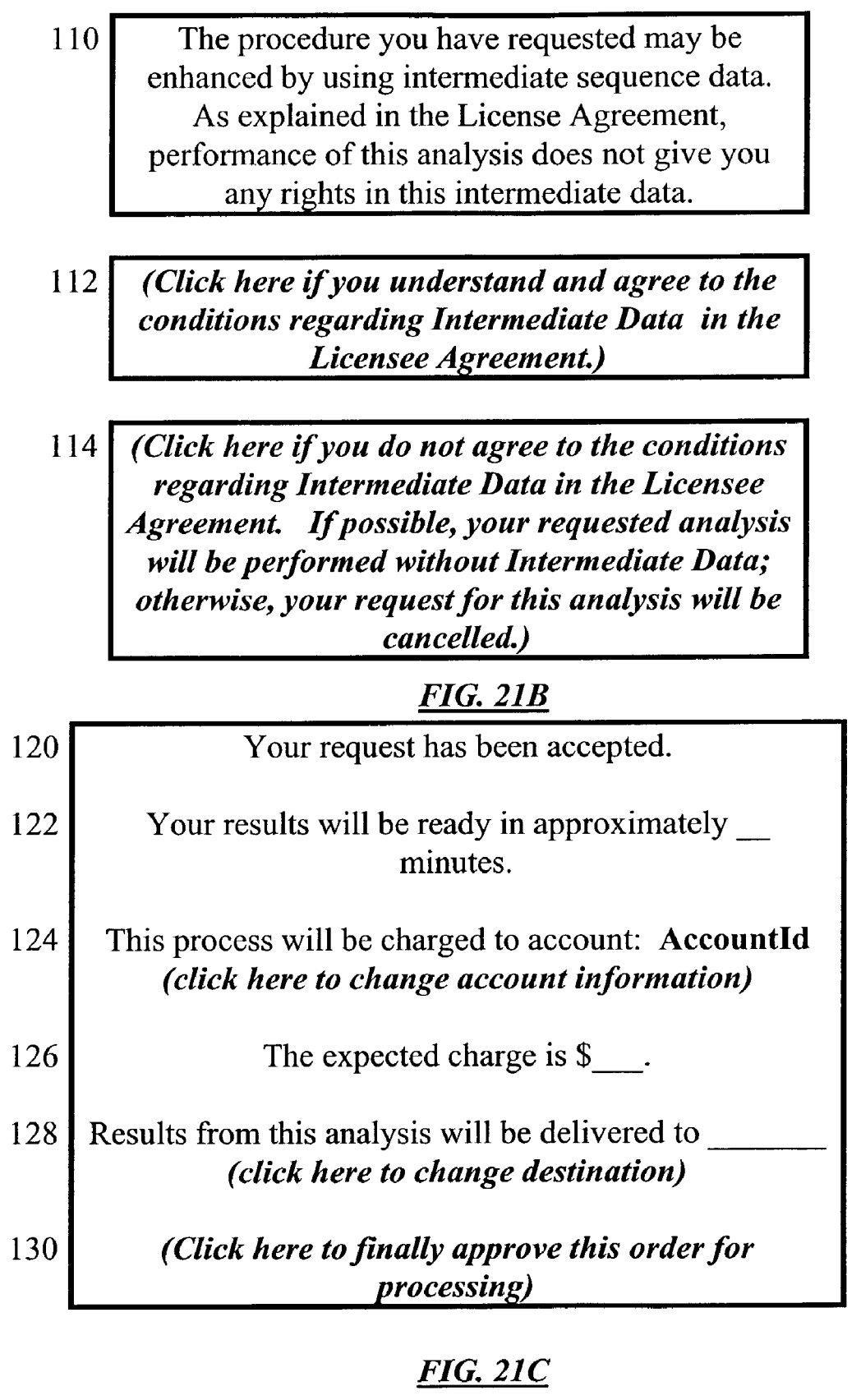

110 The procedure you have requested may be enhanced by using intermediate sequence data. As explained in the License Agreement, performance of this analysis does not give you any rights in this intermediate data.

112 *(Click here if you understand and agree to the conditions regarding Intermediate Data in the Licensee Agreement.)*

114 *(Click here if you do not agree to the conditions regarding Intermediate Data in the Licensee Agreement. If possible, your requested analysis will be performed without Intermediate Data; otherwise, your request for this analysis will be cancelled.)*

*FIG. 21B*

120 Your request has been accepted.

122 Your results will be ready in approximately __ minutes.

124 This process will be charged to account: AccountId
*(click here to change account information)*

126 The expected charge is $___.

128 Results from this analysis will be delivered to _______
*(click here to change destination)*

130 *(Click here to finally approve this order for processing)*

*FIG. 21C*

METHOD AND APPARATUS FOR CODON DETERMINING

CROSS REFERENCE TO RELATED APPLICATIONS

This application claims priority from provisional patent application U.S. Ser. No. 60/316,852 filed 31 Aug. 2001. That application and all documents referred to therein are incorporated herein by reference to the extent allowed by patent office practice.

This application also claims priority from provisional patent application U.S. Ser. No. 60/363,505 filed 9 Mar. 2002. That application and all documents referred to therein are incorporated herein by reference to the extent allowed by patent office practice.

This application claims priority from provisional patent application U.S. Ser. No. 60/339,886, filed 1 Nov. 2001 and is incorporated herein by reference for all purposes.

This application claims priority from provisional patent application U.S. Ser. No. 60/392,511, filed 27 Jun. 2002 and is incorporated herein by reference for all purposes.

This application is a continuation in part of U.S. Ser. No. 10/225,564 filed 20 Aug. 2002 which claims priority from provisional patent application titled METHOD AND SYSTEM USING SYSTEMATICALLY VARIED DATA LIBRARIES 60/314,131 filed 21 Aug. 2001. That application and all documents referred to therein are incorporated herein by reference to the extent allowed by patent office practice.

This application is related to other provisional and non-provisional patent applications assigned to Maxygen, Inc. All such applications and all documents referred to therein are incorporated herein by reference to the extent allowed by patent office practice.

COPYRIGHT NOTICE

Pursuant to 37 C.F.R. 1.71(e), Applicants note that a portion of this disclosure contains material that is subject to copyright protection (such as, but not limited to, source code listings, screen shots, user interfaces, or user instructions, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to methods and/or systems for facilitating the identification of data sequences of interest or of biological polymers (e.g., RNA, DNA, proteins, etc.) of interest. In specific embodiments, the invention involves a method and/or system for identifying a set of oligonucleotides from an initial set of one or more polypeptide sequences that will allow further analysis and/or processing of the initial sequence(s). In further embodiments, the invention involves providing graphical user interfaces and methods that facilitate design and selection of particular sequences of interest using either standalone or networked computer systems. In further embodiments, the invention involves providing results over a communications network, such as the world-wide Internet. In further embodiments, the invention includes methods and/or systems for providing associated services, such as billing, reporting, managing licensing agreements, etc.

BACKGROUND OF THE INVENTION

Various directed evolution, recombination, or diversity generation operations, synthesis, and/or analysis, have proven useful in a variety of chemical and biologic research and development settings. Thus, there is an increasing interest among diverse institutions to utilize such methods.

Effectively performing such methods, however, generally requires a specialized knowledge and skill in the selection and preparation of materials to enable the reactions. Methods requiring significant amounts of human skill and/or trial and error merely to select effective initial compounds are expensive to run in house and are not easily provided as a service to outside institutions. Thus, there remains a continuing need for novel methods and/or systems for more easily and/or automatically determining initial compounds that will enable various recombination, directed evolution, or diversity generation processes.

Communication Using Networked Information Appliances

The Internet comprises computers, information appliances, and computer networks that are interconnected through communication links. The interconnected computers exchange information using various services, such as electronic mail, ftp, the World Wide Web ("WWW") and other services, including secure services. The WWW service can be understood as allowing a server computer system (e.g., a Web server or a Web site) to send web pages of information to a remote client information appliance or computer system. The remote client computer system can then display the web pages. Generally, each resource (e.g., computer or web page) of the WWW is uniquely identifiable by a Uniform Resource Locator ("URL"). To view or interact with a specific web page, a client computer system specifies a URL for that web page in a request. The request is forwarded to a server that supports that web page. When the server receives the request, it sends that web page to the client information system. When the client computer system receives that web page, it can display the web page using a browser or can interact with the web page or interface as otherwise provided. A browser is a logic module that effects the requesting of web pages and displaying or interacting with web pages.

Currently, displayable web pages are typically defined using a Hyper Text Markup Language ("HTML"). HTML provides a standard set of tags that define how a web page is to be displayed. An HTML document contains various tags that control the displaying of text, graphics, controls, and other features. The HTML document may contain URLs of other Web pages available on that server computer system or other server computer systems. URLs can also indicate other types of interfaces, including such things as CGI scripts or executable interfaces, that information appliances use to communicate with remote information appliances or servers without necessarily displaying information to a user.

The Internet is especially conducive to providing information services to one or more remote customers. Services can include items (e.g., music or stock quotes) that are delivered electronically to a purchaser over the Internet. Services can also include handling orders for items (e.g., groceries, books, or chemical or biologic compounds, etc.) that may be delivered through conventional distribution channels (e.g., a common carrier). Services may also include handling orders for items, such as airline or theater reservations, that a purchaser accesses at a later time. A server computer system may provide an electronic version of an interface that lists items or services that are available. A user or a potential purchaser may access the interface using a browser and select various items of interest. When the user has completed selecting the items desired, the server computer system may then prompt the user for information needed to complete the service. This transaction-specific order information may include the purchaser's name or other identification, an identification for payment (such as a corporate purchase order number or account number), or additional information needed to complete the service, such as flight information.

NCBI Databases and Software

Among services of particular interest that can be provided over the internet and over other networks are biological data and biological databases. Such services include a variety of services provided by the National Center for Biotechnology Information (NCBI) of the National Institutes of Health (NIH). NCBI is charged with creating automated systems for storing and analyzing knowledge about molecular biology, biochemistry, and genetics; facilitating the use of such databases and software by the research and medical community; coordinating efforts to gather biotechnology information both nationally and internationally; and performing research into advanced methods of computer-based information processing for analyzing the structure and function of biologically important molecules.

NCBI holds responsibility for the GenBank DNA sequence database. The database has been constructed from sequences submitted by individual laboratories and by data exchange with the international nucleotide sequence databases, the European Molecular Biology Laboratory (EMBL) and the DNA Database of Japan (DDBJ), and includes patent sequence data submitted to the U.S. patent office. In addition to GenBank, NCBI supports and distributes a variety of databases for the medical and scientific communities. These include the Online Mendelian Inheritance in Man (OMIM), the Molecular Modeling Database (MMDB) of 3D protein structures, the Unique Human Gene Sequence Collection (UniGene), a Gene Map of the Human Genome, the Taxonomy Browser, and the Cancer Genome Anatomy Project (CGAP), in collaboration with the National Cancer Institute. Entrez is NCBI's search and retrieval system that provides users with integrated access to sequence, mapping, taxonomy, and structural data. Entrez also provides graphical views of sequences and chromosome maps. A feature of Entrez is the ability to retrieve related sequences, structures, and references. BLAST is a program for sequence similarity searching developed at NCBI for identifying genes and genetic features that can execute sequence searches against the entire DNA database. Additional software tools provided by NCBI include: Open Reading Frame Finder (ORF Finder), Electronic PCR, and the sequence submission tools, Sequin and BankIt. NCBI's various databases and software tools are available from the WWW or by FTP or by e-mail servers. Further information is available at www|.|ncbi|.|nlm|.|nih|.|gov.

CHIME

Some biologic data available over the internet is data that is generally viewed with a special browser "plug-in" or other executable code. One example of such a system is CHIME, a browser plug-in that allows an interactive virtual 3-dimensional display of molecular structures, including biological molecular structures. Further information regarding CHIME is available at www.mdlchime.com/chime/.

Online Oligos, Gene, or Protein Ordering

A variety of companies and institutions provide online systems for ordering biological compounds. Examples of such systems can be found at www|.|genosys|.|com/oligo_custinfo.cfm or www|.|genomictechnologies|.|com/Qbrowser2_FP.html. Typically, these systems accept some descriptor of a desired biological compound (such as an oligonucleotide, DNA strand, RNA strand, amino acid sequence, etc.) and then the requested compound is manufactured and is shipped to the customer in a liquid solution or other appropriate form.

SUMMARY

Various embodiments of the present invention provide methods and/or systems for facilitating the identification and/or synthesis of systematically varied libraries of biologic sequences and/or corresponding biological molecules. Requests for such sequences and input data for such sequences can be carried over a network, such as the Internet, or can be conveyed by other convenient digital communication means.

According to specific embodiments, the present invention provides a method and/or system for more efficiently determining desired oligonucleotides to enable a recombination and/or recombination reaction. According to further embodiments, the present invention provides a method and/or system for more efficiently identifying and/or synthesizing a minimum set of oligonucleotides that will produce all desired recombined products of one or more input sequences of polypeptides or oligonucleotides.

More specifically, according to further specific embodiments, the present invention can be understood as assisting in the identification of low-homology high-crossover oligonucleotides from one or more input data sequences. In some standard recombination reactions, it is less likely that a crossover will occur between amino acids near each other (e.g. less than 5 amino acids or 15 nucleotides apart). It is also less likely that a crossover will occur with low homology between the regions in question. According to specific embodiments of the present invention, by generating oligonucleotides as described herein, the invention allows synthetic creation of all possible crossovers in that area, regardless of distance and homology.

According to specific embodiments, the invention back-translates from a multiple-sequence aligned polypeptide sequence to determine degenerate oligonucleotides that will assemble to form nucleotide sequences encoding the desired polypeptides. According to specific embodiments, this process is carried out in such a way as to minimize the degeneracy of the output oligonucleotides, so as to make the oligonucleotides more useful in a recombination (e.g. recombination) reaction.

According to specific embodiments of the present invention, the invention can be embodied in a software package-Such a package can include algorithmic and usability features to speed various analyses and can be provided as a stand-alone program or as a set of services accessible from a server by one or more clients. A computer program according to specific embodiments of the present invention does one or more of: (1) back-translates polypeptide sequences from a multiple sequence alignment and designs degenerate oligonucleotides that will assemble to form oligonucleotide sequences encoding the desired polypeptides; or (2) accepts a number of parameters which can be used to control various aspects of its function.

Various software implementations can be constructed or designed according to the teachings provided herein to provide backtranslation services. For example, in specific embodiments, a software program according to specific embodiments of the present invention can be created as a CGI or JAVA program that can be accessed via a web browser. Such an implementation allows a program to be used both locally at an individual computer system or institutional local area network server or remotely over a wide area network, such as the Internet. In various embodiments, a user interacts with the program by entering choices into a form using a web browser and submitting those choices to an analysis component of the program, with the results of the processing displayed in the browser window and/or returned to a user as a results file and/or a chemical composition or mixture. In particular embodiments, an input to a program according to the invention is digital data indicating a multiple polypeptide sequence alignment (such as in MSF format). In specific embodiments, a user interface can allow input of additional parameters such as a codon bias table, parameters controlling the processing of polypeptide sequences, their backtranslation, the division of coding sequences into oligonucleotides, termination codons or types of output oligonucleotides and the format of the program's output and can also allow a user to input reference sequences. Default values for parameters can be automatically entered into an empty form, allowing a user to only address those parameters that the user wishes to specify a different value.

Thus, according to specific embodiments of the invention, a software system is provided that allows a user to input data representing one or more polypeptide sequences. Typically this data will comprise two or more aligned sequences of somewhat related (e.g. homologous) proteins, with some variations in some amino acid position(s). (In an alternative embodiment, one sequence can be used as an initial sequence, with diversity indications placed at particular positions by an operator.) In a general embodiment, the present invention outputs a plurality of listing of nucleotide sequences (oligonucleotides) that can be used in a recombination procedure to generate systematically varied libraries of oligonucleotides that can be used to synthesize systematically varied libraries of polypeptides from the input protein sequences.

In further embodiments, a system or method according to specific embodiments of the invention allows a user to indicate additional input data or options, such as particular codon biases, options to vary or not vary particular locations, minimum and/or maximum length of output sequences, end degeneracy, maximum degeneracy, etc.

The analysis provided according to specific embodiments of the present invention may be done entirely in a digital information processing system (e.g. one or more computers) or may be done using chemical or biological synthesis and chemical or biological systematic variation techniques, or a combination of both digital information processing analysis and chemical or biological synthesis analysis. Results of such an analysis can be provided to a client as a digital file indicating output sequences or as one or more preparations of biological molecules or oligonucleotides of interest.

The input to a system or method according to specific embodiments of the present invention for providing systematically varied libraries of biologic sequences can be either digital data or a molecule or mixture of molecules of interest. The input can be either provided by the client, or can be derived from other sources such as publicly available biologic sequence data banks. Input data, in the case of digital data, can be provided to a system or method according to specific embodiments of the present invention or fetched by a system or method according to specific embodiments of the present invention over a network, such as the Internet.

In further embodiments, the present invention may be understood in the context of biologic analysis services provided over a communication media. An important application for the present invention, and an independent embodiment, is in the field of providing biologic data services over the Internet, optionally using Internet media protocols and formats, such as HTTP, RTTP, XML, HTML, dHTML, VRML, as well as image, audio, or video formats etc. However, using the teachings provided herein, it will be understood by those of skill in the art that the methods and apparatus of the present invention could be advantageously used in other related situations where users access content over a communication channel, such as modem access systems, institution network systems, wireless systems, etc.

In specific embodiments, the present invention can be understood as involving new business methods related to providing biologic sequences or services, such as providing for sale a set of nucleotide sequences that will facilitate or enable further directed evolution analysis.

A further advantage that will be understood from the teachings herein is that in specific embodiments, the present invention can allow a biologic service provider to provide biologic analysis and/or libraries using data and/or methods that reside at a server side system and never are made known to a user of a system. For example, in some recombination methods, it is desirable to use either intermediate sequences, bridging sequences, or homologous sequences (either synthetic or from nature) during the recombination reaction. According to specific embodiments of the invention, the invention can provide a user with a systematically varied library result of an input, optionally while using intermediate or bridging sequences that are never made available to the user.

Similarly, in specific embodiments, the present invention can allow a biologic service provider to provide biologic analysis and/or systematically varied libraries based on data received from a client, while preserving confidentiality of the data received from the client and of the results provided to the client. Thus, according to specific embodiments of the present invention, a biologic sequence library provider can provide libraries of never-before synthesized sequences while preserving the secrecy and confidentiality of both the client's input sequence data and any provided output sequence data.

In a further aspect, according to specific embodiments, the invention may involve one or more different algorithms for generating degenerate codons. One such algorithm is a unique approach adapted from a statistical-mechanics Monte-Carlo algorithm. A different algorithm is an adaptation of a Genetic Algorithm for determining best oligonucleotides. While these algorithms provide advantages in specific embodiments, neither is a necessary part of all embodiments and other computerized methods can be used for identifying degenerate codons of interest such as, for example, by performing an exhaustive search.

The invention and various specific aspects and embodiments will be better understood with reference to the following drawings and detailed descriptions. In some of the drawings and detailed descriptions below, the present invention is described in terms of the important independent embodiment of a system operating on a digital data network. This should not be taken to limit the invention, which, using the teachings provided herein, can be applied to other situations, such as cable television networks, wireless networks, etc. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. The functional aspects of the invention that are implemented on a computer, as will be understood from the teachings herein, may be implemented or accomplished using any appropriate implementation environment or programming language, such as C, C++, Cobol, Pascal, Java, Java-script, HTML, XML, dHTML, assembly or machine code programming, etc. All references, publications, patents, and patent applications cited herein are hereby incorporated by reference in their entirety for all purposes.

Furthermore, in some aspects, the present invention is described in terms of client/server systems. A number of computing systems and computing architectures are described in the art as client/server. For the purposes of this description, client/server should be understood to include any architecture or configuration wherein a program or device (e.g., a client) accesses another remote or separate program or device that is providing the desired service (e.g., a server).

BRIEF DESCRIPTION OF THE DRAWINGS

FIG. 1 is a table illustrating nucleotide base codes.

FIG. 2 is a table illustrating amino acid codes.

FIG. 3 is a table illustrating triplet codons and corresponding amino acids.

FIG. 4 illustrates an example main graphical user interface according to specific embodiments of the present invention. The graphical user interface depicts sequences corresponding to SEQ ID NOS: 6-10.

FIG. 18 illustrates a portion of an example of initial aligned sequence data according to specific embodiments of the invention. The sequences depicted correspond to SEQ ID NOS: 27-32.

FIG. 19 illustrates a portion of an example of backtranslation results data showing codon listings according to specific embodiments of the invention. The sequences depicted correspond to SEQ ID NOS: 33-38.

FIG. 20 illustrates a portion of an example XML data holding input data, output data, and processing options according to specific embodiments of the invention. The sequences depicted correspond to SEQ ID NOS: 39-42.

FIGS. 21A-C is a block diagram illustrating example interfaces and a process for oligonucleotide determination results according to specific embodiments of the present invention.

DESCRIPTION OF SPECIFIC EMBODIMENTS

1. Diversity Generation Operations

Figure 5:
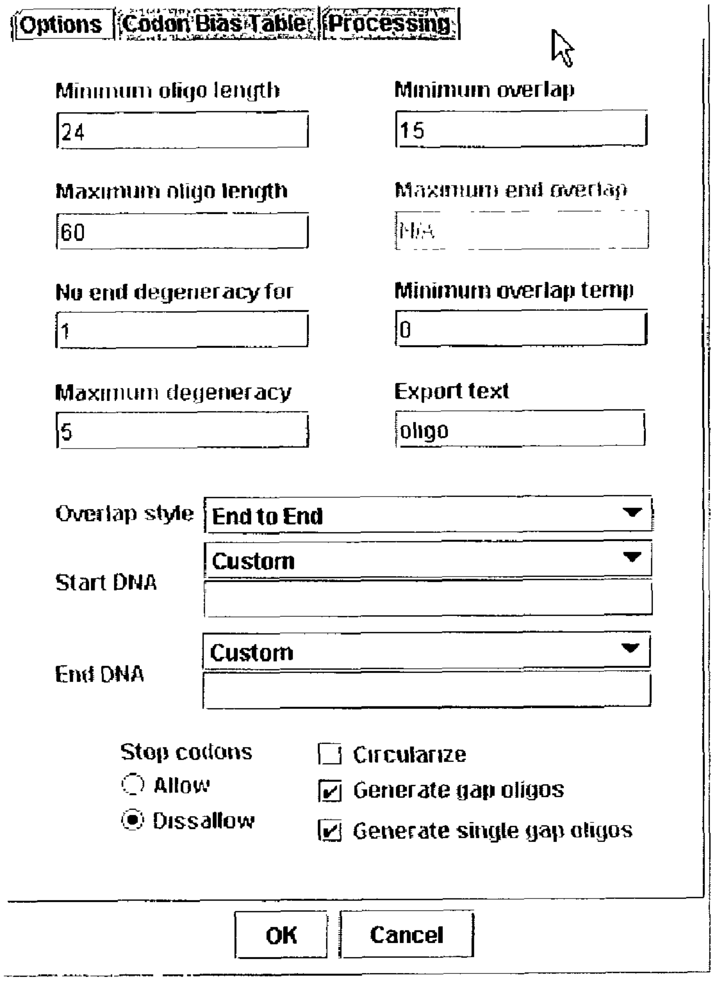
FIG. 5 illustrates an example options graphical user interface according to specific embodiments of the present invention.

A variety of diversity generating techniques and/or processes that can be facilitated according to specific embodiments of the invention are available and described in the art. Other techniques are described in coassigned patent applications or may be developed or modified in the future. Thus, the present invention according to specific embodiments can be used to facilitate any known or yet to be developed diversity generation operation. Various diversity generation operation can be used separately and/or in combination to produce one or more variants of a nucleic acid or set of nucleic acids (or oligonucleotides), as well as variants of encoded proteins (or polypeptides). Individually and collectively, these procedures provide robust, widely applicable ways of generating diversified sequences (e.g. nucleic acids, sets of nucleic acids (including, e.g., nucleic acid libraries), polypeptides, or sets of polypeptides) useful, e.g., for the engineering or rapid evolution of nucleic acids, proteins, pathways, cells and/or organisms with new and/or improved characteristics. While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties, or that encode proteins with or which confer desirable properties. Following diversification by one or more of the methods herein, or otherwise available to one of skill, any nucleic acids that are produced can be selected for encoding and distribution according to specific embodiments of the present invention. This can include identifying any activity that can be detected, for example, in an automated or automatable format, by any of the assays in the art prior to encoding and distribution as described herein.

Descriptions of a variety of diversity generating procedures for generating modified nucleic acid sequences are found in the following publications and the references cited therein: Soong, N. et al. (2000) "Molecular breeding of viruses" *Nat Genet* 25(4):436-439; Stemmer, et al. (1999) "Molecular breeding of viruses for targeting and other clinical properties" *Tumor Targeting* 4:1-4; Ness et al. (1999) "DNA Shuffling of subgenomic sequences of subtilisin" *Nature Biotechnology* 17:893-896; Chang et al. (1999) "Evolution of a cytokine using DNA family shuffling" *Nature Biotechnology* 17:793-797; Minshull and Stemmer (1999) "Protein evolution by molecular breeding" *Current Opinion in Chemical Biology* 3:284-290; Christians et al. (1999) "Directed evolution of thymidine kinase for AZT phosphorylation using DNA family shuffling" *Nature Biotechnology* 17:259-264; Crameri et al. (1998) "DNA shuffling of a family of genes from diverse species accelerates directed evolution" *Nature* 391:288-291; Crameri et al. (1997) "Molecular evolution of an arsenate detoxification pathway by DNA shuffling," *Nature Biotechnology* 15:436-438; Zhang et al. (1997) "Directed evolution of an effective fucosidase from a galactosidase by DNA shuffling and screening" *Proc. Natl. Acad. Sci. USA* 94:4504-4509; Patten et al. (1997) "Applications of DNA Shuffling to Pharmaceuticals and Vaccines" *Current Opinion in Biotechnology* 8:724-733; Crameri et al. (1996) "Construction and evolution of antibody-phage libraries by DNA shuffling" *Nature Medicine* 2:100-103; Crameri et al. (1996) "Improved green fluorescent protein by molecular evolution using DNA shuffling" *Nature Biotechnology* 14:315-319; Gates et al. (1996) "Affinity selective isolation of ligands from peptide libraries through display on a lac repressor 'headpiece dimer'" *Journal of Molecular Biology* 255: 373-386; Stemmer (1996) "Sexual PCR and Assembly PCR" In: *The Encyclopedia of Molecular Biology*. VCH Publishers, New York. pp. 447-457; Crameri and Stemmer (1995) "Combinatorial multiple cassette mutagenesis creates all the permutations of mutant and wildtype cassettes" *BioTechniques* 18:194-195; Stemmer et al., (1995) "Single-step assembly of a gene and entire plasmid form large numbers of oligodeoxyribonucleotides" *Gene,* 164:49-53; Stemmer (1995) "The Evolution of Molecular Computation" *Science* 270: 1510; Stemmer (1995) "Searching Sequence Space" *Bio/Technology* 13:549-553; Stemmer (1994) "Rapid evolution of a protein in vitro by DNA shuffling" *Nature* 370:389-391; and Stemmer (1994) "DNA shuffling by random fragmentation and reassembly: In vitro recombination for molecular evolution." *Proc. Natl. Acad. Sci. USA* 91:10747-10751.

Mutational methods of generating diversity include, for example, site-directed mutagenesis (Ling et al. (1997) "Approaches to DNA mutagenesis: an overview" *Anal Biochem.* 254(2): 157-178; Dale et al. (1996) "Oligonucleotide-directed random mutagenesis using the phosphorothioate method" *Methods Mol. Biol.* 57:369-374; Smith (1985) "In vitro mutagenesis" *Ann. Rev. Genet.* 19:423-462; Botstein & Shortle (1985) "Strategies and applications of in vitro mutagenesis" *Science* 229:1193-1201; Carter (1986) "Site-directed mutagenesis" *Biochem. J.* 237:1-7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488-492; Kunkel et al. (1987) "Rapid and efficient site-specific mutagenesis without phenotypic selection" *Methods in Enzymol.* 154, 367-382; and Bass et al. (1988) "Mutant Trp repressors with new DNA-binding specificities" *Science* 242:240-245); oligonucleotide-directed mutagenesis (*Methods in Enzymol.* 100: 468-500 (1983); *Methods in Enzymol.* 154: 329-350 (1987); Zoller & Smith (1982) "Oligonucleotide-directed mutagenesis using M13-derived vectors: an efficient and general procedure for the production of point mutations in any DNA fragment" *Nucleic Acids Res.* 10:6487-6500; Zoller & Smith (1983) "Oligonucleotide-directed mutagenesis of DNA fragments cloned into M13 vectors" *Methods in Enzymol.* 100: 468-500; and Zoller & Smith (1987) "Oligonucleotide-directed mutagenesis: a simple method using two oligonucleotide primers and a single-stranded DNA template" *Methods in Enzymol.* 154:329-350); phosphorothioate-modified DNA mutagenesis (Taylor et al. (1985) "The use of phosphorothioate-modified DNA in restriction enzyme reactions to prepare nicked DNA" *Nucl. Acids Res.* 13: 8749-8764; Taylor et al. (1985) "The rapid generation of oligonucleotide-directed mutations at high frequency using phosphorothioate-modified DNA" *Nucl. Acids Res.* 13: 8765-8787 (1985); Nakamaye & Eckstein (1986) "Inhibition of restriction endonuclease Nci I cleavage by phosphorothioate groups and its application to oligonucleotide-directed mutagenesis" *Nucl. Acids Res.* 14: 9679-9698; Sayers et al. (1988) "Y-T Exonucleases in phosphorothioate-based oligonucleotide-directed mutagenesis" *Nucl. Acids Res.* 16:791-802; and Sayers et al. (1988) "Strand specific cleavage of phosphorothioate-containing DNA by reaction with restriction endonucleases in the presence of ethidium bromide"

*Nucl. Acids Res.* 16: 803-814); mutagenesis using gapped duplex DNA (Kramer et al. (1984) "The gapped duplex DNA approach to oligonucleotide-directed mutation construction" *Nucl. Acids Res.* 12: 9441-9456; Kramer & Fritz (1987) *Methods in Enzymol.* "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" *Nucl. Acids Res.* 16: 7207; and Fritz et al. (1988) "Oligonucleotide-directed construction of mutations: a gapped duplex DNA procedure without enzymatic reactions in vitro" *Nucl. Acids Res.* 16: 6987-6999).

Additional suitable methods include point mismatch repair (Kramer et al. (1984) "Point Mismatch Repair" *Cell* 38:879-887), mutagenesis using repair-deficient host strains (Carter et al. (1985) "Improved oligonucleotide site-directed mutagenesis using M13 vectors" *Nucl. Acids Res.* 13: 4431-4443; and Carter (1987) "Improved oligonucleotide-directed mutagenesis using M13 vectors" *Methods in Enzymol.* 154: 382-403), deletion mutagenesis (Eghtedarzadeh & Henikoff (1986) "Use of oligonucleotides to generate large deletions" *Nucl. Acids Res.* 14: 5115), restriction-selection and restriction-purification (Wells et al. (1986) "Importance of hydrogen-bond formation in stabilizing the transition state of subtilisin" *Phil. Trans. R. Soc. Lond.* A 317: 415-423), mutagenesis by total gene synthesis (Nambiar et al. (1984) "Total synthesis and cloning of a gene coding for the ribonuclease S protein" *Science* 223: 1299-1301; Sakamar and Khorana (1988) "Total synthesis and expression of a gene for the a-subunit of bovine rod outer segment guanine nucleotide-binding protein (transducin)" *Nucl. Acids Res.* 14: 6361-6372; Wells et al. (1985) "Cassette mutagenesis: an efficient method for generation of multiple mutations at defined sites" *Gene* 34:315-323; and Grundström et al. (1985) "Oligonucleotide-directed mutagenesis by microscale 'shot-gun' gene synthesis" *Nucl. Acids Res.* 13: 3305-3316), double-strand break repair (Mandecki (1986) "Oligonucleotide-directed double-strand break repair in plasmids of *Escherichia coli*: a method for site-specific mutagenesis" *Proc. Natl. Acad. Sci. USA,* 83:7177-7181; and Arnold (1993) "Protein engineering for unusual environments" *Current Opinion in Biotechnology* 4:450-455). Additional details on many of the above methods can be found in *Methods in Enzymology* Volume 154, which also describes useful controls for trouble-shooting problems with various mutagenesis methods.

Additional details regarding various diversity generating methods can be found in the following U.S. patents, PCT publications and applications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" PCT/US00/26708 by Welch et al., "Use of Codon-Varied Oligonucleotide Synthesis for Synthetic Shuffling;" and PCT/US01/06775 "Single-Stranded Nucleic Acid Template-Mediated Recombination and Nucleic Acid Fragment Isolation" by Affholter.

In brief, several different general classes of sequence modification methods, such as mutation, recombination, etc. can be used at a server system as described herein according to specific embodiments of the present invention. The following exemplify some of the different types of preferred formats for diversity generation in the context of the present invention, including, e.g., certain recombination based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described in several of the references above, e.g., in Stemmer (1994) *Proc. Natl. Acad. Sci. USA* 91:10747-10751.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above.

Whole genome recombination methods can also be used in which whole genomes of cells or other organisms are recombined, optionally including spiking of the genomic recombination mixtures with desired library components (e.g., genes corresponding to the pathways of the present invention). These methods have many applications, including those in which the identity of a target gene is not known. Details on such methods are found, e.g., in WO 98/31837 by del Cardayre et al. "Evolution of Whole Cells and Organisms by Recursive Sequence Recombination;" and in, e.g., PCT/US99/15972 by del Cardayre et al., also entitled "Evolution of Whole Cells and Organisms by Recursive Sequence Recombination."

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561 by Crameri et al., "Olgonucleotide Mediated Nucleic Acid Recombination;" PCT/US00/26708 by Welch et al., "Use of Codon-Varied Oligonucleotide Synthesis for Synthetic Shuffling;" WO 00/42560 by Selifonov et al., "Methods for Making Character Strings, Polynucleotides and Polypeptides Having Desired Characteristics;" and WO 00/42559 by Selifonov and Stemmer "Methods of Populating Data Structures for Use in Evolutionary Simulations."

According to specific embodiments of the invention, methods of recombination can be performed digitally on an information processing system. For example, algorithms can be used in a computer to recombine sequence strings that correspond to homologous (or even non-homologous) biologic molecules. According to specific embodiments of the invention, after processing in a computer system, the resulting sequence strings can be converted into nucleic acids by synthesis of nucleic acids which correspond to the recombined sequences, e.g., in concert with oligonucleotide synthesis/gene reassembly techniques. This approach can generate random, partially random or designed variants. Many details regarding various embodiments of computer enabled recombination, including the use of various algorithms, operators and the like in computer systems, as well as combinations of designed nucleic acids and/or proteins (e.g., based on cross-over site selection) as well as designed, pseudo-random or random recombination methods are described in WO 00/42560 by Selifonov et al., "Methods for Making Character Strings, Polynucleotides and Polypeptides Having Desired Characteristics" and WO 00/42559 by Selifonov and Stemmer "Methods of Populating Data Structures for Use in Evolutionary Simulations." Extensive details regarding computer (e.g., in silico) recombination methods are found in these applications.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. These methods can be used in physical systems or can be performed in computer systems according to specific embodiments of the invention. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "Single-Stranded Nucleic Acid Template-Mediated Recombination and Nucleic Acid Fragment Isolation" by Affholter, PCT/US01/06775.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see e.g., U.S. Pat. No. 5,965,408, "Method of DNA reassembly by interrupting synthesis" to Short, and the references above), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) "A combinatorial approach to hybrid enzymes independent of DNA homology" *Nature Biotech* 17:1205. This approach can be used to generate an initial a library of variants which can optionally serve as a substrate for one or more in vitro or in vivo recombination methods. See, also, Ostermeier et al. (1999) "Combinatorial Protein Engineering by Incremental Truncation," *Proc. Natl. Acad. Sci. USA,* 96: 3562-67; Ostermeier et al. (1999), "Incremental Truncation as a Strategy in the Engineering of Novel Biocatalysts," *Biological and Medicinal Chemistry,* 7: 2139-44.

Mutational methods which result in the alteration of individual nucleotides or groups of contiguous or non-contiguous nucleotides can be favorably employed to introduce nucleotide diversity, prior to preparing a sequence for encoding. Many mutagenesis methods are found in the above-cited references; additional details regarding mutagenesis methods can be found in following, which can also be applied to the present invention. For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) *Technique* 1: 11-15 and Caldwell et al. (1992) *PCR Methods Applic.* 2:28-33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and, e.g., in Reidhaar-Olson et al. (1988) *Science,* 241:53-57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) *Proc. Natl. Acad. Sci. USA* 89:7811-7815.

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11: 1548-1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g., Schellenberger U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783,431 "METHODS FOR GENERATING AND SCREENING NOVEL METABOLIC PATHWAYS," and Thompson, et al. (1998) U.S. Pat. No. 5,824,485 METHODS FOR GENERATING AND SCREENING NOVEL METABOLIC PATHWAYS) and their use to identify protein activities of interest has been proposed (In addition to the references noted above, see, Short (1999) U.S. Pat. No. 5,958,672 "PROTEIN ACTIVITY SCREENING OF CLONES HAVING DNA FROM UNCULTIVATED MICROORGANISMS"). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above described procedures have been largely directed to increasing nucleic acid and/or encoded protein diversity. However, in many cases, not all of the diversity is useful (e.g., functional) and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" *Gene* 215: 471) prior to diversifying according to any of the methods described herein.

Libraries can be biased towards nucleic acids which encode proteins with desirable enzyme activities. For example, after identifying a clone from a library which exhibits a specified activity, the clone can be mutagenized using any known method for introducing DNA alterations. A library comprising the mutagenized homologues is then screened for a desired activity, which can be the same as or different from the initially specified activity. An example of such a procedure is proposed in Short (1999) U.S. Pat. No. 5,939,250 for "PRODUCTION OF ENZYMES HAVING DESIRED ACTIVITIES BY MUTAGENESIS." Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above.

"Non-Stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods be applied to the present invention as well. Random or semi-random mutagenesis using doped or degenerate oligonucleotides is also described in, e.g., Arkin and Youvan (1992) "Optimizing nucleotide mixtures to encode specific subsets of amino acids for semi-random mutagenesis" *Biotechnology* 10:297-300; Reidhaar-Olson et al. (1991) "Random mutagenesis of protein sequences using oligonucleotide cassettes" *Methods Enzymol.* 208:564-86; Lim and Sauer (1991) "The role of internal packing interactions in determining the structure and stability of a protein" *J. Mol. Biol.* 219:359-76; Breyer and Sauer (1989) "Mutational analysis of the fine specificity of binding of monoclonal antibody 5° F. to lambda repressor" *J. Biol. Chem.* 264:13355-60); and "Walk-Through Mutagenesis" (Crea, R; U.S. Pat. Nos. 5,830,650 and 5,798,208, and EP Patent 0527809 B1.

It will readily be appreciated that any of the above described techniques suitable for enriching a library prior to diversification can also be used to screen the products, or libraries of products, produced by the diversity generating methods.

Kits for mutagenesis, library construction and other diversity generation methods are also commercially available. For example, kits are available from, e.g., Stratagene (e.g., QuickChange™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology Ltd (e.g., using the Carter/Winter method above).

The above references provide many mutational formats, including recombination, recursive recombination, recursive mutation and combinations or recombination with other forms of mutagenesis, as well as many modifications of these formats. Regardless of the diversity generation operations used, a result according to specific embodiments of the invention can be recombined (with each other, or with related (or even unrelated) sequences) to produce a diverse set of recombinant nucleic acids, including, e.g., sets of homologous nucleic acids, as well as corresponding polypeptides.

Back-Translating Polypeptides to Facilitate Codon Recombination

Other issues arise when the desired initial parent sequences of a recombination reaction are proteins or amino acid sequences (more generally referred to herein as polypeptides) rather than genes or gene portions. A typical example of such a recombination reaction will start with two or more related polypeptide sequences. (Though a single polypeptide sequence can be used in some embodiments, with additionally specified variation data as described further below. Also, the relatedness of the initial sequence can vary widely, with some additional techniques, such as bridging oligonucleotides, allowing reaction of relatively unrelated amino acid and/or other biological sequences.) These related amino acid sequences will include regions that are homologous and one or more regions or positions that differ. A desired end-product goal of a directed evolution (or recombination) procedure performed on the initial sequences might be a mixture or library of new proteins containing all possible combinations of the variations in the parent protein.

To accomplish the directed evolution of the polypeptides using gene-recombination techniques, it is often desirable to first back-translate the initial polypeptides to corresponding codon sequences. The codon sequences can then be used in a gene-recombination or directed-evolution procedure. Directed evolution of codon sequences can either be performed in a computer system (sometimes referred to as in silico) or in a test-tube or similar artificial container reaction (in vitro). In some systems, steps of a recombination reaction may be performed using a living vector or culture (in vivo). In some systems, directed evolution steps may be partially performed by a computer system and partially using in vitro or in vivo processes. Once the directed evolution or recombination processing is performed on the oligonucleotides, one or more of the recombined oligonucleotides can then be forward-translated to produce the desired systematically varied polypeptide sequence or sequences.

In performing the backtranslation, a number of choices can be made. As is well-known, the majority of naturally occurring amino acids correspond to more than one possible codon. Arginine, for example, is encoded by the DNA codons: CGU, CGC, CGA, or CGG, (which can also be expressed as the degenerate or ambiguous code CGN). Thus, in back-translating a position containing only Arginine, a choice of codon can be made. Oftentimes, this choice is made with reference to a codon bias table, which specifies one or more preferred codons used in particular species for encoding the desired amino acid. Further issues that arise is whether once a codon is chosen for an amino acid, will that codon choice by used for every occurrence of the amino acid in the initial string, or will codons be selected according to some statistical values, such as the occurrence of that particular codon in a particular natural system.

When a position in encountered where there exists two or more different amino acids in different input polypeptides or where further diversity has been specified by the user, a further issue arises in selecting one or more backtranslation codons that will encode for the all of desired different amino acids and that will generally not encode for other amino acids or stop codes.

An issue that arises when it is desired to use outputs of a backtranslation particularly in a physical directed-evolution (or recombination) procedure is minimizing the costs of creating the oligonucleotides needed for the reaction. Generally, in oligonucleotide synthesis, every varying nucleotide position (sometimes referred to as a degeneracy or degenerate position) can result in additional costs for such things as synthesis, purification, and final recombination reaction. Therefore, when performing such backtranslations, it can be desirable to identify a minimum set of oligonucleotides that will provide all desired variations in the end products of a directed evolution reaction. Another way of expressing this goal is to determine a minimum number of oligonucleotides with a minimum amount of degeneracy. It will be understood from the present discussion that a degenerate or ambiguous code is any code representation that indicates two or more physical codons or bases. Thus, the degenerate codon GCN indicates the four oligonucleotides GCG, GCC, GCT, GCA. The degenerate code N indicated the four bases ACTG. Thus, according to specific embodiments of the invention, a desired degenerate codon can be understood as a set of non-degenerate codons that can be synthesized using standard techniques and which, once synthesized, does not code for any amino acids that are not wanted. Table 1 illustrates commonly used nucleotide base codes, including ambiguous/degenerate codes. (It is understood in the art that in some very rare situations, some organisms are able to change between two very similar amino acids for the same codon. Also, there are some organisms that edit RNA during protein translations so that one codon can become another codon or two codons.)

Earlier Disclosed General Algorithm for Designing Oligonucleotides for Synthesis Earlier techniques for selecting oligonucleotides have been described (such as discussed in patent application Ser. No. 09/618,579 filed 18 Jul. 2000, but these techniques often did not produce oligonucleotides with minimum degeneracy. These described techniques also did not include features to increase their usability to the oligonucleotide designers.

The present invention, in various embodiments, modifies and extends previously discussed methods of determining a best set of oligonucleotides. In specific embodiments, the invention provides a set of computer interfaces that allow a user to select desired input data and options. In further embodiments, a computer system according to specific embodiments of the invention is able to identify an optimal set of oligonucleotides for performing a recombination reaction. In further embodiments, a computer system according to specific embodiments of the invention is able to complete a business transaction with an outside institute for identifying and/or ordering desired oligonucleotides.

According to further specific embodiments, the present invention involves making such data available to clients/customers over a communication media in the form of libraries of biologic sequence data. These libraries can be provided as digital data or as synthesized biological molecules. In specific embodiments, provision of such libraries can be facilitated using various information processing methods and systems as described herein, including communication over a network. In various specific embodiments, such libraries can be generated using, either entirely or in part, from data provided by a client. In various other specific embodiments, such libraries can be generated using, either entirely or in part, initial sequence data available from various commercial or public biologic databases.

According to specific embodiments of the present invention, a system allows access by customers to sophisticated and/or proprietary biologic analysis or synthesis including recombination or shuffling routines over a network, while allowing a service provider to keep those routines secret. According to further specific embodiments of the invention, the invention can also provide a user with recombination or analysis results wherein intermediate data is used to facilitate or create the results, while keeping that intermediate data secret. Thus, the invention allows a server to reduce the amount of sensitive information that is exposed to a client system or a user on a client system. According to further specific embodiments of the invention, the invention can also provide a user with recombination or analysis results from a user's initial data, while keeping that user's initial data secret.

An understanding of the following discussion may be aided by reference to symbol tables regarding bases, codons, degenerate codons, and amino acid that are generally familiar in the art. For the readers convenience, these tables are reproduced in the figures. FIG. 1 is a table illustrating nucleotide base codes. FIG. 2 is a table illustrating amino acid codes. FIG. 3 is a table illustrating triplet codons and corresponding amino acids.

2. Example Software Interface

According to specific embodiments, aspects of the present invention can be understood by considering an example computer software interface that allows a user to specify input data and options for identifying oligonucleotides of interest. FIG. 4 illustrates an example main graphical user interface according to specific embodiments of the present invention. On this example interface are labels A-F. These labels are not part of the interface but are used to aid description and correspond to the descriptions below.

(A) This area indicates new diversity a user wants to add to a protein/polypeptide alignment. To add diversity, according to specific embodiments of the present invention, a user can click on the amino acid column to which the user wishes to add diversity and click a "New" button. To remove added diversity, a user can double click on the diversity the user wishes to remove. According to further embodiments, this area can also show new diversity that the algorithm adds when the user allows it. Thus, amino acids can be displayed using different indications (such as different fonts or font styles or different colors) depending on whether the user added them, or the user told the algorithm to allow more amino acids to reduce oligonucleotide count.

(B) This area can when selected display aligned polypeptide input data. Typically, a user will import this data from a file, using an import menu option provided in the menu area of the screen. (For example, by clicking File→Import Alignment.) According to specific embodiments of the present invention, a computer software system will read MSF formatted data files, though other input formats can be provided for according to specific embodiments of the invention. In other embodiments, a user can "Paste" data into the window, using a familiar paste function provided by a computer operating system. According to further embodiments, area A not only displays the polypeptide input data, but allows a user to specify particular option parameters for particular amino acids in the input sequences. (To clear the settings, a user in specific embodiments can click on the amino acid and click the trash can for clear state or alternatively can double-click or an amino acid code that has settings set.) According to specific embodiments of the invention, sequences may be displayed in a collapsed form, or in a sequence logos form.

As an example, the following option parameters can be set for amino acids in the input sequence strings. These settings can be indicated by different font styles or different colors over the amino acid codes on color display computer systems.

Deleted Diversity (Red or underlined). This option allows a user to indicate amino acids that are in the polypeptide alignment but that the user does not want reflected in the output oligonucleotides thus indicating the amino acids are deleted causes the method to treat them as if they were not in the alignment.

Required Diversity (Blue or small b). This option allows a user to indicate for which amino acids the output oligonucleotides must code. This option is useful in embodiments where a user can indicate that the method can automatically drop related amino acids to reduce the output oligonucleotide count. This option, as all options indicated herein, will not be present in all embodiments.

Linkage Group (Other indications, e.g. violet or small v or green or italics). This option allows a user to indicate that the amino acids are part of a linkage group. For amino acids in a linkage group the method will attempt to place the codons on the same output oligonucleotides.

(C) Oligo Positions. This area displays the oligo positions. The positions of the oligos are normally calculated by the program, but the user can manually set the positions.

(D) According to specific embodiments of the present invention, this area can be open to indicate a minimal/best set of codons that the algorithm identified for each position. These codons will sometimes have degenerate codes, generally only if there are multiple amino acids for that position in the aligned input group. Thus, in one example, at the $11^{th}$ amino acid position, the possible amino acids are S and T, and the resultant minimum redundant codon is WCT. Likewise, at position 24, the minimum redundant codon identified code be MAG. The user can also elect to import a set of reference codons for back translation. The program will attempt to back translate to the provided codon(s) at a given position.

Note that it is often true that a degenerate codon code is only used in area D when there is a single base difference between the codons that are coding for the peptides at that position. This is because when there are more than one differences, often use of TWO degenerate codes will result in a codon that will have some instances that do not code for ONLY the two peptides in the parent sequences.

Also note that there are some artifacts that may show up in area D, based on the particular algorithm used to generate the oligonucleotides. This is due to the probabilistic nature of algorithms such as the MC and GA described below, which always produce a correct answer given the specified criteria, but can produce different correct answers, even with the same input data, when they are run more than once.

(E) According to specific embodiments of the present invention, this area indicates the set of codons that are generated from the degenerate codon output. This is useful for further showing the actual variability in codons and to help a user get a feel for how many different DNA sequences will actually be created.

(F) According to specific embodiments of the present invention, this area displays the oligonucleotides that were created by the algorithm. In specific embodiments, this area can include forward and reverse oligonucleotides, and these can be indicated using different display indications (such as GREEN or plain test for forward and RED or italic text for reverse.) According to specific embodiments of the present invention, a user can change an oligonucleotide, for example by indicating (e.g. using double click) a codon the user wants to change and selecting the desired one from a provided list of expanded codons and the non-expanded (i.e. degenerate) codons for that position. If a user wants to add/extend an oligonucleotide, the user can indicate the blank space next to the oligonucleotide and select the appropriate codon to add from the list. In one example, which represents a default in some embodiments, oligonucleotides identified by the computer system are all 20 codons long, with oligonucleotides selected so that there is 10 codon crossover for each.

3. Functions that can be Accessed from the Main Interface According to Specific Embodiments According to specific embodiments of the present invention, the invention further provides a graphical user interface with menu options to facilitate processing of proteins to determine oligonucleotides. For description purposes, these commands can be grouped into commands that are common to a variety of different computer programs and those that are more specifically tailored to computer assisted identification of oligonucleotides according to specific embodiments of the present invention. These commands are available from the example main screen illustrated in FIG. 4.

Example top-level commands and/or buttons:

Open: Opens a saved file (in XML or other file format) containing alignment(s), option(s), and result(s) from a previous session with the software application.

Save: Saves current settings, results, and options in a file for later accessing. Generally saved as an XML file that contains settings, sequence data, and output oligonucleotides if the processing has run.

Import alignment: Imports a file (such as a Multiple Sequence File (MSF)) of a group of related and aligned amino acid sequences.

Export Oligos Exports the oligonucleotides generated by the program in a data file format (such as text) that without gap characters that can be used for oligonucleotide synthesis.

Buttons

As shown in the example interface in FIG. 4, a number of options can be provided to a user via buttons displayed on the main screen in this example at the top of the interface. It will be understood to those of skill in the art that many variations on the examples provided herein are within the scope of the invention.

Starting from the left at the top of the illustrated example interface of FIG. 4, the first two buttons provide button activations for opening and saving files.

It will be understood to a person of skill in the art from the teachings herein that these example indications are just examples and that other different visual buttons or indications, or spoken-recognition commands, could be substituted or added to the example indications shown to activate the same functions or options.

4. Functions that can be Accessed Using Submenu or Options Screens According to Specific Embodiments As will be understood in the art, the present invention can provide a number of other functions or options that are not necessarily entered at the main screen, but that may be entered in one or more sub-menu interfaces or options interfaces. As discussed above, the illustrations and discussion below are of specific examples of interfaces according to specific embodiments of the present invention. Other interfaces, including interfaces in different languages, interfaces using different display devices or graphical indications, and interfaces that are voice activated or that communicating with another information processing system rather than a human user, are also possible according to various embodiments of the invention.

FIG. 5 illustrates an example options graphical user interface according to specific embodiments of the present invention. The example interface allows a user to specify a number of options according to various specific embodiments of the present invention. Not all of these options are present in all embodiments, and additional options can be provided in specific embodiments. As an example, the following options can be provided in specific software implementation of the invention:

Minimum Oligo Length: The minimum length of Oligonucleotides that will be created by the program.

Minimum overlap: The minimum overlap between a forward and reverse oligonucleotide. In specific embodiments, only one oligonucleotide has to overlap with at least this length to be satisfied. According to various specific embodiments of the present invention, output data can include oligonucleotides that are all of the same length or can include oligonucleotide that have varying lengths.

Maximum Oligo Length: The maximum length of output Oligonucleotides.

Maximum end overlap: This optional input in some embodiments can be used to limit the amount of overlap between two forward Oligonucleotides that are covering different but consecutive parts of the sequence.

No end degeneracy for _: This option prevents output oligonucleotides from having degeneracy within a number of codons from the end of the oligonucleotide.

Minimum overlap temp: An optional input that when present causes the processing module when designing oligonucleotides to calculate an estimated $T_m$ (temperature of melting) for the overlap area between a forward and reverse oligonucleotide and the program automatically extends the oligonucleotide if this value is not met. According to specific embodiments of the invention, with this option, a processing module extends the length of the oligonucleotides one codon at a time until the average Tm of the overlap is above the cutoff. To determine the average Tm, the processing module generates all possible Non-degenerate oligonucleotides at this position based on the minimal degenerate codons list and calculates the Tm for each. Tm, according to specific embodiments of the invention, is the temperature of melting at which ½ of the oligonucleotides in solution will be hydrogen-bonded (based on complementary bases) and ½ will not be.

Maximum degeneracy: This setting allows a user to set the maximum amount of degeneracy per oligonucleotide. If an oligonucleotide exceeds this value, it is split up (horizontally) into multiple oligonucleotides, each of roughly or exactly the same length, with the degenerate codons split between them. Thus, each of the new oligonucleotides will still cover the same area of sequence and be close to or exactly the same length but each will code for less diversity. Unless a user requires 0 degenerate codons, the output codons might have degeneracy after splitting, e.g. GANTAN could be split into GANTAC and GACTAN or it could be split into GARTAR and GAYTAY.

Export Text: This string is pre-pended to each oligonucleotide exported into text to help a user remember what the Oligonucleotides are.

Stop codons: Allows a user to specify whether or not to allow stop codons to be created by degenerate codons. In some situations a user may want to allow it to create varability in the length of the protein, though in many situations this option will be set to not allow stop codons.

Append Stop Codon: This option will append a stop codon to the end of each sequence in the alignment if one does not already exist. This is useful because protein multiple alignments often drop out the ending stop symbol. Not having a stop codon at the end of a sequence could cause extra DNA to be used to code for the end of the protein, most likely resulting in a non-functional protein. A user should be careful using this option in conjunction with END DNA because if one appends a stop codon, but the end DNA encodes for a purification peptide or other protein, there will not be produced sequences that in-vivo code for that purification peptide or other protein.

Circularize: This option creates Oligonucleotides at the end and beginning of the sequence that will cause a fully assembled sequence to circularize in-vitro.

Generate Gap Oligos: This option will create oligonucleotides that will not include any diversity at positions where there are gaps in the alignment. This option relates to gaps longer than one codon/amino acid. Gaps are places in a sequence alignment where one or more sequences have undergone one or more insertions or deletions along their evolutionary history. Although gaps are represented by special symbols (--- or _) they are in essence the absence of sequence. Therefore a gap oligonucleotide ATG---GAC will in fact be the oligonucleotide ATGGAC.

Generate Single Gap Oligos: This option will create oligonucleotides that will not include any diversity at positions where there are gaps in the alignment. This option relates to gaps which are only one codon/amino acid.

Figure 6:
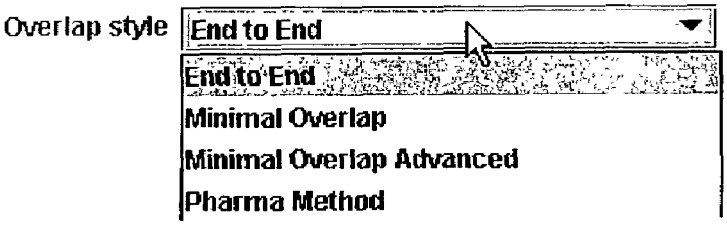
FIG. 6 illustrates an example graphical user interface for specifying an overlap style according to specific embodiments of the present invention.

Overlap Style: An option for a user to indicate the method the user wants to use for selecting the positions of the Oligonucleotides. FIG. 6 illustrates an example graphical user interface for specifying an overlap style according to specific embodiments of the present invention. This option can be selected by a user to facilitate the style of recombination the user want to perform with the output oligonucleotides. Example options are:

a) The End to End method creates Oligonucleotides for ligation assembly.
b) The Minimal Overlap creates Oligonucleotides for PCR extension assembly.
c) The Minimal Overlap Advanced tries to adjust the positions of the Oligonucleotides to make the overlap regions as similar length or $T_m$ as possible, while trying to reduce total Oligonucleotide number. According to specific embodiments of the invention, this processing can be accomplished through a genetic algorithm as described in more detail below.

d) The Pharma Method creates something similar to End to End but creates both forward and complimentary oligonucleotides for all oligonucleotide positions. This method can reduce the probability of including a mutation due to poor oligonucleotide quality.

Start DNA is the DNA sequence to append to the beginning of all oligonucleotides that start at the start of the alignment. (note: if it is a reverse oligonucleotide, this sequence will be reverse+complemented before adding. Various built-in DNA sequences can be used according to specific embodiments of the invention, such a set of vectors (e.g. plasmids for cloning and expressing genes) that are useful for recombination that are described in coassigned patent applications. According to specific embodiments of the invention, some of the cloning region of these vectors can be included in a list so that if a user want to add it to their end oligonucleotides, the user can choose it from the list. This reduces errors due to mistyped sequences.

Figure 7A:
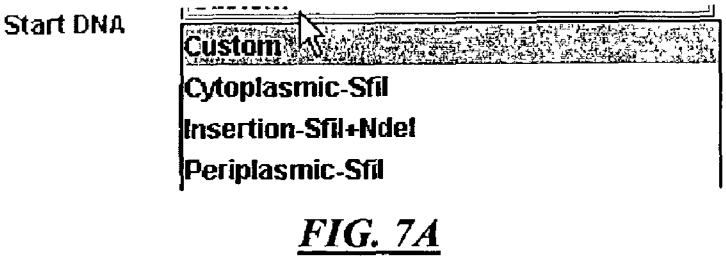
FIGS. 7A-B illustrate example graphical user interfaces for indicating START and END codons according to specific embodiments of the present invention.
Figure 7B:
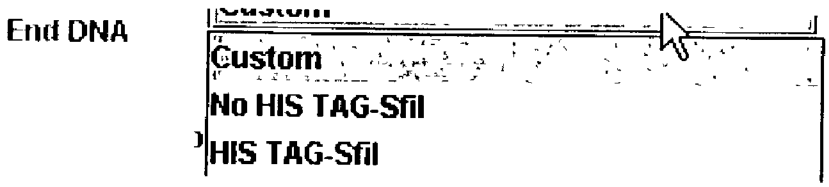

End DNA is the DNA sequence to append to the end of all Oligonucleotides that end at the end of the alignment. (note: if it is a reverse oligonucleotide, this sequence will be reverse+complemented before adding. FIGS. 7A-B illustrate example graphical user interfaces for indicating START and END codons according to specific embodiments of the present invention.

Codon Bias

Figure 8:
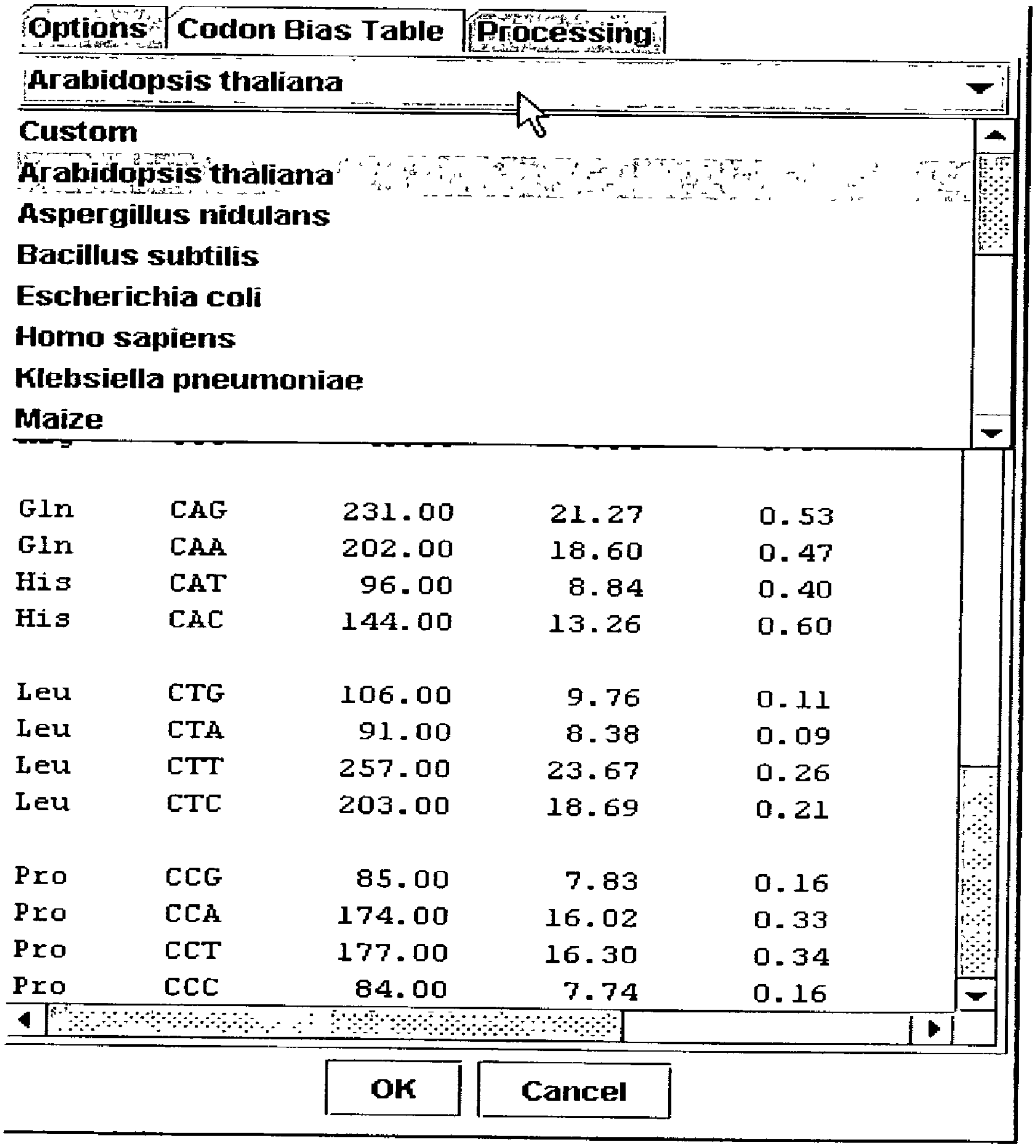
FIG. 8 illustrates an example graphical user interface for selecting a codon bias table according to specific embodiments of the present invention.

FIG. 8 illustrates an example graphical user interface for selecting a codon bias table according to specific embodiments of the present invention. This interface allows a user to select the codon bias table to use when back-translating Amino acids to codons. According to specific embodiments of the present, a user can paste in one from an existing source or select from a list of included tables. Pasted in tables should be in GCG format. A Codon Frequency Cutoff option can allow a user to select a cutoff frequency when the user does not want to use codons that do not occur frequently in nature.

5. Other Software Embodiment

As previously indicated, the previous detailed discussion provides just one example embodiment of the invention. Other software embodiments are possible and within the scope of skill of ordinary practitioners in the art. For example, the invention can provide a textual file interface that includes input data and options in a text file format (such as XML) and then batch processes based on those input and options. Below is provided some descriptions of an alternative embodiment according to embodiments of the present invention for inputting data and parameters to an analysis component. As will be seen, in this embodiment a number of the options use different terminology and have somewhat different functions.

Parameters

Add Stop codons at Internal C-termini—this feature will automatically add a stop codon at the C-terminus of any protein which ends before the end of the alignment. In terms of oligonucleotide assembly, these stops may be necessary if the heterogeneity of the source protein C-terminal lengths is to be passed on to clones resulting from oligonucleotide assembly.

Active Sequences—By default, the invention will process all protein sequences in the input alignment. However, if desired, a subset of these protein sequences can be defined here and the other sequences in the alignment will be ignored. Sequences should be specified by their position in the alignment (i.e. the uppermost sequence is number 1 etc.). Sequences in this field should be separated by spaces and/or commas, and ranges (e.g. 1-4) are accepted.

Sacred Sequences—By default, the invention will design a single set of oligonucleotides capable of encoding all active sequences in the input alignment. However, if desired, certain sequences may be identified as sacred—that is to say, oligonucleotides will be designed to encode each of these sequences individually. All sequences not specified as sacred are dubbed profane, and a single set of oligonucleotides will be designed for the entire set of profane sequences. Note that a possible mode of use for the invention would be to make all sequences sacred, to assemble the oligonucleotides for each protein sequence separately and then to recombine the resulting coding sequences subsequently. As for the active sequences, sacred sequences are specified by number and selections should be separated by spaces and/or commas. Ranges are also accepted (e.g. 1, 3, 5-7).

Codon Bias Text—The sequences designed according to specific embodiments of the present invention will use a codon bias of the user's choice. The codon bias data may be either pasted as text into the area provided, or selected from a number of bias files available in a local directory. Pasted text will be used by preference if present. The codon bias data should be in GCG format.

Codon Bias Choice—If no codon bias data is pasted into the form, the selection indicated on this pull-down menu will be used instead. In specific embodiments, when the program generates the input form, it looks for local codon bias files and lists them here. An error may result if the available files are changed while a user is filling in the input form. The codon bias files accompanying the program at the time of first installation according to specific embodiments of the present invention are part of a larger resource available at: iubio.bio-.indiana.edu/soft/molbio/codon/.

Codon Frequency Threshold—All codons with frequencies below this threshold will be discarded and may not be used in DNA sequence design. Frequencies should be expressed as a number between 0 (codon is never observed for amino acid X) and 1 (codon is observed for all instances of amino acid X).

Resolve Alternatives—In generating possible coding DNA sequences for the input protein sequences, a module calculates the minimally degenerate codons capable of encoding all of the active proteins. In some cases these codons will include alternative bases at certain positions—where any of 2 or more bases will encode the correct amino acid(s). If this option is active, any alternative bases will be eliminated, leaving only the base which will result in codons with highest frequencies overall. For example, suppose that at a given position in a protein alignment, a degenerate codon must be devised which can encode amino acids G or P. The codons for G are GGG, GGA, GGT and GGC, and those for P are CCG, CCA, CCT and CCC. So, the degenerate codon must allow C or G at the first two positions (specified by degenerate code S). The choice of bases for the third position depends upon whether the option to 'resolve alternatives' is active or not. If it is, a module will choose the single best base for the third position and there will be no degeneracy at this position. In this context, the best base is the one estimated to give the most favorable codon bias choices overall. In this case, we might end up using GGG to encode G and CCG to encode P. Suppose, however, that the most favorable codon for G is GGC, and the most favorable codon for P is CCG. If 'resolve alternatives' is not active, the process will not resolve the four alternatives at the third position down to a single choice and will instead allow the most favorable choices to be made for each amino acid. Now, G will be encoded by GGC and P by CCG. The principal significance of this parameter is as follows: resolving alternatives may lead to lower degeneracy but poorer codon bias choices, whereas not resolving alternatives may lead to higher degeneracy but allow more favorable codon bias choices.

Minimum Length—The shortest length that oligonucleotides may be. If oligonucleotide ends are restricted to codon boundaries, the minimum length will be rounded up to the next multiple of 3. Please note that some oligonucleotides covering sequence ends or gaps may necessarily be shorter than the specified minimum length.

Maximum Length—The greatest length that oligonucleotides may be. If oligonucleotide ends are restricted to codon boundaries, the effective maximum length will be the highest multiple of 3 less than or equal to the value entered.

Minimum Overlap—The shortest length of overlap permitted between neighboring oligonucleotides on opposite strands. NB if oligonucleotide ends are restricted to codon boundaries, the minimum overlap will be rounded up to the next multiple of 3.

Maximum End Overlap—The maximum limit on overlap of ends from one oligonucleotide to the next oligonucleotide on the same strand.

End Degeneracy—The length from each end of each oligonucleotide which should be kept free of degeneracy if possible. According to specific embodiments, the invention will test different oligonucleotide start and end positions to attempt to avoid end degeneracy.

Maximum Degeneracy—The maximum degree of nucleotide degeneracy permitted in each oligonucleotide. Defined as the total number of bases introduced by degeneracy divided by the length of the oligonucleotide (for example, the oligonucleotide GTRATN would have degeneracy $4/6$=67%). When the specified threshold is exceeded, the offending oligonucleotide is divided into two less degenerate oligonucleotides.

Disallow Stop Codons—Prevents the introduction of stop codons through degeneracy. A degenerate codon encoding a number of amino acids might also be able to encode a stop—if this option is active, such a codon will be eliminated by dividing the oligonucleotide in question into two less degenerate oligonucleotides.

Oligo Ends only at Codon Boundaries—Forces all oligonucleotides to start and end exactly at boundaries between codons. Hence when this option is active, all oligonucleotide lengths will be multiples of 3. This is desirable if oligonucleotides are to be synthesized from tri-nucleotide units.

Log Information about Progress—Enables the output of miscellaneous information about the programs calculations and progress. This information is likely to assist in ensuring that all parameters have been chosen correctly, and may be valuable if saved for future reference.

Output Warnings—If the program discovers a non-fatal violation of the input parameters, it will output a warning message and continue. These messages will only be displayed if this option is active.

Keep Sacred Duplicates—When identical duplicate oligonucleotides occur, a method according to specific embodiments of the present invention generally outputs only one of the duplicate set. However, if a user is designing oligonucleotides for separate synthesis of sacred sequences, it might be more convenient to display all oligonucleotides relating to those sequences even if they are identical to oligonucleotides found elsewhere in the output. If this option is active, this is what will happen, and duplicate oligonucleotides relating to sacred sequences will not be discarded.

Output Detailed Oligo Information—Enables the output of detailed information about each oligonucleotide, including which parts of the alignment it covers, the protein sequences which it was designed to encode and whether or not it encodes a protein end or ends.

Suppress Output except Oligo Sequences—Suppresses all forms of output except oligonucleotide sequences. This option might be desirable, once the values of all parameters have been carefully set, to output the oligonucleotide sequences in the form most easily fed into an oligonucleotide synthesizer.

Sorting Oligos—The oligonucleotides to be output may be sorted in either of two ways. The first is by position along the alignment; oligonucleotides beginning closer to the N-terminal end will be output first. The second is by protein sequence; oligonucleotides will be output in groups according to which protein sequences they encode (all profane oligonucleotides will be output together). The second option might be desirable if oligonucleotides for sacred sequences were to be assembled in isolation from oligonucleotides for other sequences.

Speed—According to specific embodiments of the present invention, the program may take from less than one second up to several minutes to finish a processing task. Most of this time is needed for deciding upon the minimal degenerate codon set, but oligonucleotide boundaries may be time consuming as well. The program is likely to run faster when: (1) No limit is placed on degeneracy in oligonucleotide ends; (2) Less range is allowed between minimum and maximum oligonucleotide lengths (3) Oligonucleotide end positions are restricted to codon boundaries. The speed of the program will also depend on various other factors including the length of the alignment, the number of constituent sequences and the processing speed and load on the computer system performing the calculations.

Number of Output Oligos—The number of oligonucleotides required to fulfill a given request depends upon many factors. If it is a priority to minimize the number of oligonucleotides required, consider increasing the degeneracy permitted and/or permitting potential stop codons introduced by degeneracy. Lowering the codon frequency threshold may also have a lesser effect. Gaps in the alignment have a profound effect upon the number of oligonucleotides required, particularly for alignments with a large number of profane sequences. For each gap in a profane sequence, oligonucleotides are designed such that assembly can result in this same gap being represented in the context of any of the profane sequences. In extreme cases, making all sequences sacred may actually reduce the number of oligonucleotides in the program output.

Mode of Use—Log files, warnings and detailed oligonucleotide information are important and a user can use and record this information possible. In general, it may be convenient and effective to run a program several times with this information being output, using it to refine the input parameters until the desired results are obtained. Then the program may be run again with the same parameters but with the extra forms of output suppressed in order to obtain the oligonucleotide sequences in the most convenient form.

6. Optional Additional Features

According to further specific embodiments, aspects of the present invention can be incorporated into a further software system that provides additional options and/or features as described below.

Protein size estimates are provided for input diversity. Further, if a user makes changes to the alignment (such as disallowing diversity or adding new diversity), a "Get Size" indication is provided to recalculate the estimate. Alternatively, this can be done automatically when changes are made. In specific embodiments, a system does not include gaps in the estimate unless single gap or gap oligos is selected in the tools dialog.

Manual oligonucleotide positions are available. According to specific embodiments, the first time a user runs the software, it returns the oligonucleotide positions generated by the algorithm. Indications are provided to set new positions and an indication allows a user to use the manual positions upon re-submit.

A user can load a set of reference minimal degenerate codons using a "Load" indication.

A user can request to have the system calculate the Tm for regions in the oligonucleotide pane be selecting a forward or reverse section and selecting a "Calculate Tm" indication. The system will produce the oligonucleotides and calculate and present the average minimum and average maximum Tm for the set.

An advanced tab in the tools dialog provides settings for CodonTools/GaCodonTools. This allows a user to set the threshold when a user wants the Genetic Algorithm to do the calculation. A degeneracy weight bar is also provided. Generally, a user should avoid 1.0 for the weight as this will produce all codons without reducing the degenerate codons. A value of 0.99 has been found to work well though.

For the reference degenerate codons, a user can import a FASTA DNA sequence. A user can also modify the set of degenerate codons (add, edit, delete) and the program will validate that the codon is well formed.

7. Monte Carlo Method for Identifying Oligonucleotide Sets

According to specific embodiments of the present invention, the invention determines a set of oligonucleotides for positions in the input sequence diversity using a method adapted from Monte Carlo statistical analysis. In general, Monte Carlo analysis provides approximate solutions to a variety of problems by performing statistical sampling experiments on a computer and can be used in problems with no probabilistic content as well as to those with inherent probabilistic structure. Monte Carlo methods originated from work on the atomic bomb during the second world war that involved a direct simulation of the probabilistic problems concerned with random neutron diffusion in fissile material. Monte Carlo methods are particularly useful for problems for which the time to evaluate an exact solution grows near exponentially with the number of possible solutions.

According to specific embodiments of the present invention, for a given polypeptide alignment, a Monte Carlo method returns a minimal solution set of ambiguous (e.g. degenerate) codons for each position in the alignment. The solution set for a position codes for the full diversity of amino acids specified at that position. A general method according to this embodiment of the present invention can be understood from the example provided below.

An initial solution set of ambiguous codons is selected for the amino acid diversity. This initial solution set can be determined in different ways according to various embodiments of the present invention. According to one set of specific embodiments of the present invention, this initial solution set is generated by selecting a random ambiguous codon for each amino acid in the diversity. (Note that, generally, both the amino acid diversity and codon solutions are unordered sets; in other words, position does not matter.) Each of these ambiguous codons is selected with the constraints that (a) it must code for the particular amino acid and (b) it must not code for any amino acids or stop codons outside of the diversity (though it may code for other amino acids in the diversity). In alternative embodiments, other methods can be used to select an initial solution. For example, a predetermined table can be established assigning one or more codons to every possible amino acid or to various possible groups of amino acids. This predetermined table can be populated to include codons with higher frequencies in a codon bias table, for example, or codons that have been determined or are believed to allow the method to more quickly and/or accurately find an optimal solution.

According to specific embodiments, the number of ambiguous codons selected for the initial solution is the same as the number of amino acids in the diversity, though, as will be understood from the teachings provided herein, more codons could be included in an initial solution set.

A set of all ambiguous codons that code for at least one amino acid in the diversity and that do not code for any amino acid not in the diversity or any stop codon is determined and designated the allowed codon set that will be used to search for a preferred solution according to this embodiment. Note that the total number of possible degenerate codons is 3375 (15×15×15), but most of these will not meet the criteria for most diversities.

Using the initial solution and the allowed codon set described above, a Monte Carlo algorithm is performed to attempt to find the best, or a near-best, preferred minimal ambiguous codon set for the amino acid diversity. Starting with the initial solution as a current solution, a method according to specific embodiments of the invention, changes a codon for a randomly selected amino acid in the current solution to another codon from the allowed set. This new solution is then compared to the current solution, using a scoring function and transition parameters as described below. Based on the scoring function and transition parameters, a decision is made to keep the current solution or to discard it and transition to the new solution. This process is repeated until some stop criteria is reached (e.g. a prescribed number of steps).

To compare a new solution to a current solution, a scoring function is determined. According to a specific embodiment of the present invention, a scoring function uses one or more properties calculated for each solution such as:

1. A number of unique codons (NUNIQ) in the solution. (Note that there might be inclusive codons, e.g., GAG is included in RAG, thus, a set of GAG and RAG has only one unique codon, RAG.)
2. A combined frequency (FREQ) from, for example, a selected codon bias table, for all the non-degenerate codons specified by the unique codons in a solution.
3. The total number of non-degenerate codons (NDEG) represented by the unique degenerate codons in the solution is computed. (e.g. NDEG of RAW+TAN+ACG=4+4+1=9).

The invention, according to specific embodiments, compares scores of solutions in the order: NUNIQ, FREQ, NDEG, According to specific embodiments, the solution with the smaller NUNIQ is considered "better." If the NUNIQ's are equal, then the solution with a lower NDEG is better. If NDEG's are also equal, the solution with a higher FREQ is better. In various specific embodiments, these criteria can be modified. For example, in some embodiments, NUNIQ's that are within 5% of each other are considered equal. Or, for example, if NUNIQ's are within 20% of each other, but the FREQ of one solution is more than five times greater than the frequency of the other solution, the solution with the higher FREQ is selected. It will be understood from the teachings herein that other criteria, including more complex combinations and comparisons of properties and calculation of different properties, can be used in various embodiments of the invention.

For many amino acid diversities, there will be many local minimums in the space of all solutions. Thus, according to specific embodiments of the present invention, the invention includes further parameters to help avoid settling on a local minimum that is not the true preferred minimum.

According to various embodiments of the present invention, a transition probability is used at transitions between a new and current solution. In specific embodiments, a transition probability is set to zero if the new solution does not code for all the amino acids in the diversity (meaning that the new solution will never replace the current solution) and is set to one if a new solution is better according to the scoring criteria than the current (meaning that the new solution will always replace the current solution). However, in order to move away from local minimums, at times a new solution will replace the current, even when the new solution is not better than the current solution. The frequency that this type of transition (better→worse) is allowed is, according to specific embodiments of the present invention, determined by a weighting factor referred to, according to the present invention, as temperature. According to specific embodiments, temperature is a selected number between 0 and 1 (0<=temperature<1) that determines the probability of transition to a new solution when the new solution is worse than the current solution. In a specific embodiment, for example, a temperature is set to a value, e.g. 0.8, and then a random number between 0 and 1 is generated using any random number generating technique or algorithm. If the random number is less than the temperature, the transition to a worse solution is allowed, otherwise the transition to a worse solution is not allowed. It will be understood from the teachings herein that higher values selected for temperature will result in higher probability of transition to a worse solution. Thus, temperature can be selected for a particular system to optimize performance, either to allow a system to find solutions more quickly or to allow the system to explore more areas of the solution space. Temperature can also be varied (usually gradually reduced) during search of the solution space to force the system gradually to retain better solutions.

To decide if an optimal solution has been found, according to specific embodiments, the invention performs one or more checks. An example check is to determine for how many cycles the solution has not changed. If the number of cycles exceeds any specified limit, the search process ends. Another check is to reduce the temperature over a number of cycles until reaching zero and at zero to check until a number of cycles have been performed without a change in the solution. A further check is for the system to always remember the best solution prior to the current solution that it has found. Once the termination condition has been reached, the invention compares scores of the best prior solution to the current solution so ensure that it did not find a solution elsewhere in the solution space that is better than the final solution.

It will be understood from the teachings herein that a number of variations on the specific example are within the scope of a Monte Carlo method according to embodiments of the present invention. For example, the transition probabilities need not be set exactly to 0 or 1 when the criteria described above are met. This will allow, at times, solutions that do not code for all amino acid in the diversity to be selected or will allow better solutions to not be selected. This may, in some embodiments, lengthen the search time but allow for more complete exploration of the search space.

It will also be understood from the teachings provided herein that a number of different optimization (or shortcuts) can be incorporated according to specific embodiments of the present invention. For example, NUNIQ, FREQ, NDEG may be calculated in order for each pair of solutions, so that if the NUNIQs are not equal, the other factors are not calculated. Likewise, if the NUNIQ's are equal, but the NDEGs are not, then FREQ need not be calculated. A further example optimization is that when finding solutions for a particular polypeptide or group of polypeptides, it may be found that identical or very related diversities are specified. Thus, once a final preferred minimal ambiguous codon solution is found for a diversity of amino acids, that preferred minimal ambiguous codon solution can be stored and used as the solution for any identical diversities of amino acids or can be used as an initial solution for closely related diversities of amino acids.

Figure 9:
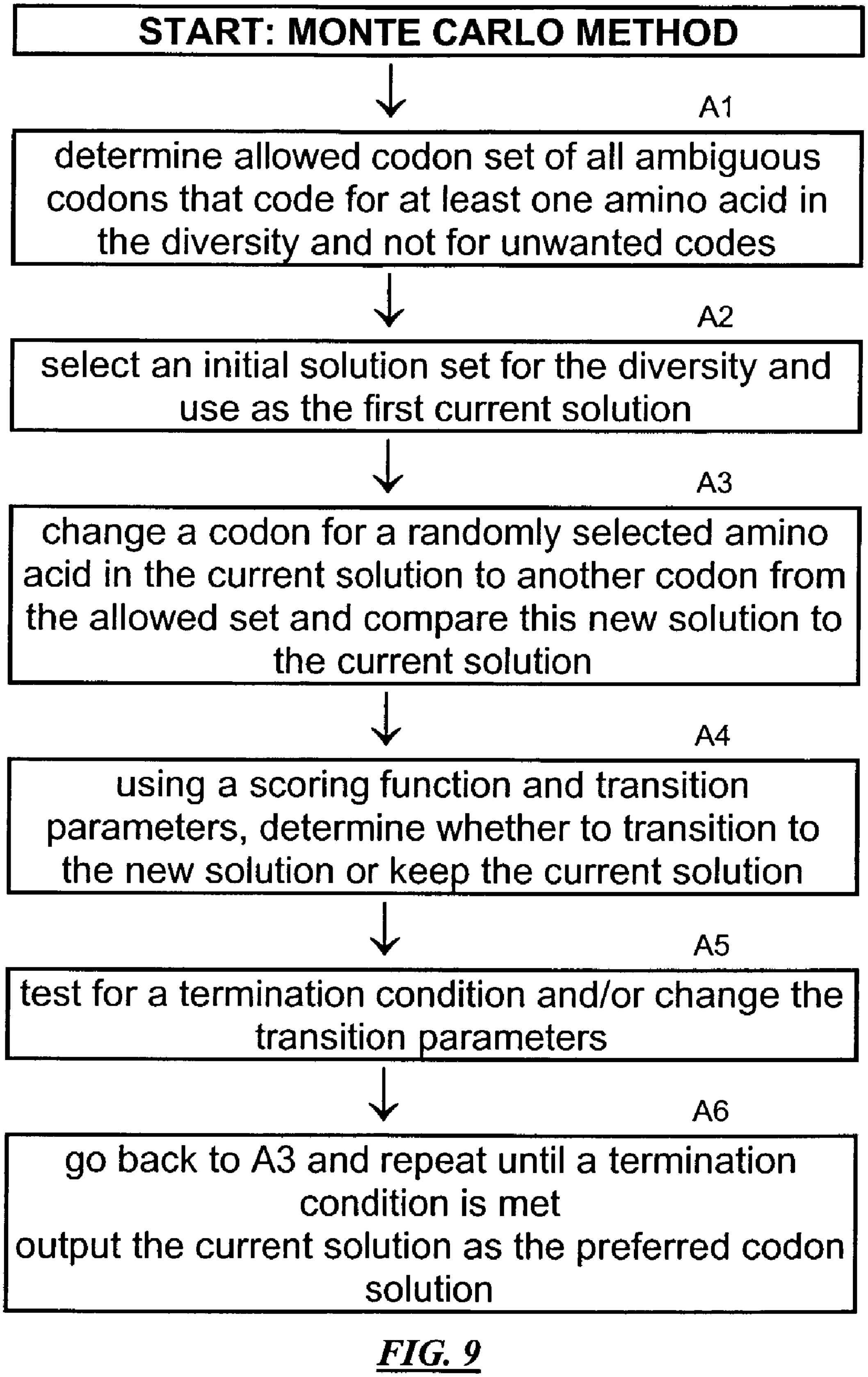
FIG. 9 is a flow chart illustrating an example Monte Carlo method according to specific embodiments of the invention.

FIG. 9 is a flow chart illustrating an example Monte Carlo method according to specific embodiments of the invention.

8. Genetic Method for Identifying Oligonucleotide Sets

In further specific embodiments, the present invention utilizes Genetic Algorithm methods to determine minimal degenerate or otherwise preferred oligonucleotides. A degenerate oligonucleotide is one that contains a codon with at least one or more ambiguous base codes. Genetic Algorithm methods are generally understood as computation methods for solving complex optimization problems for which the total possible solution space is too large to solve by conventional methods. A classical example of such a problem is referred to in the art as the "travelling salesman" problem.

In general, a problem to be solved by genetic methods is coded in terms of genes and chromosomes. In specific embodiments, definitions of terms must be made so that every gene is a possible value of the system and every possible combination of genes is a chromosome. A fitness function is determined or designed for the chromosomes, generally resulting in some type of fitness score. A selection operator is an operator that is used to select a subset of a population of chromosomes for some type of breeding and/or mutation. Generally, in a genetic algorithm system, an initial population of chromosomes is generated, either at random or by some initial methods or approximation. Then, using one or more fitness functions, selection operators, and allowed breeding or mutation operations, a first evolved generation is produced. From that generation, a second generation is produced. This procedure is repeated iteratively. If the initial problem is modeled correctly into the system, over several generations the system will generate a solution that is close to optimal or possibly optimal.

According to specific embodiments of the present invention, a genetic method is adapted to determine optimal codons to code for a diversity of amino acids. In specific example embodiments, this method can be described as comprising the following steps: (1) Create a population of chromosomes for each position in the alignment for which a minimal codon solution is sought; (2) Determine a number of desired genes in each chromosome, where each gene represents a possible codon (either ambiguous or non-ambiguous). It has been determined that a convenient number is one gene for every different amino acid in the diversity because this is the largest irreducible number of ambiguous codons that may be found in a solution. (3) Create an initial seed population of chromosomes. The number of chromosomes created can vary, with a convenient number found to be about 1,000. The initial genes used for the seed population can be selected in a number of ways including entirely at random and including ambiguous codons. However, it has been determined that a convenient method is to select genes/codons for chromosomes at random from a set comprising all the possible non-ambiguous codons above the cut-off frequency of the codon bias table that code for any one of the amino acids in the original diversity. According to specific embodiments of the present invention, this initial random selection does not require that all the amino acids are represented by a gene/codon in each chromosome. (4) Determine a fitness score for each chromosome according to a fitness function. (5) Select chromosomes to generate a next generation one or more selection operations. (6) Generate a next generation from selected chromosomes using one or more breeding and/or mutation operations. (7) Repeat steps 4 through 7 until a desired number of chromosomes (such as one) converges on a most-fit solution. Details according to specific example embodiments of the present invention regarding are described below.

An initial seed population according to specific embodiments of the invention is determined as follows: (a) back-translate each amino acid in the diversity to determine non-ambiguous codons above a cut-off in a codon bias table and place each determined codon into a selection set; (b) for each seed chromosome in the initial population select, at random, a number of codons/genes from the selection set. It will be understood from the teachings herein that this method will create chromosomes that include multiple codons for one of the original amino acids and do not include codons for other amino acids. Alternatively, selection can be done so that every chromosome includes, at random, codons for at least a specific number of amino acids in the diversity or for all the amino acids in the diversity. Also note that the overall method described herein will work with an initial population generated entirely at random from allowed symbols (e.g. A, C, T, G or A, C, T. G, R, Y, M, K, S, W, B, D, H, V, N) or an initial population with little or no variations, such as made up entirely of codons AAA or of repeating patterns of codons. However, the described seed populations is believed to more quickly converge to a desired.

A fitness function and/or fitness score according to specific embodiments of the present invention is used to indicate what makes a given solution more fit than another solutions. Determining such a fitness function can be challenging. A problem arises in going from the initial diversity to a minimal set. A balance should be struck between minimizing the number of ambiguous codons but not letting the amount of unambiguous codons get too large. A fitness function according to specific embodiments of the present invention proceeds as follows: (a)

One solution to the fitness function problem proceeds as follows:

(1) a chromosome should contain codons that code for, at a minimum, all the amino acids indicated by the diversity;

(2) a chromosome should not contain codons that code for anything else (3) a chromosome in some situations should include a minimized number of ambiguous codons (this might be important in regions where there is annealing going on, like at the end of the oligonucleotide, in order to do the recombination reaction)

(4) a chromosome should provide a reduced number of all codons (e.g. should have a smaller coding set). A "coding set" in this context, are the minimum codons/genes needed to represent all the genes in the chromosome. Thus, for chromosome MRT GCA GMA AGT (SEQ ID NO:1), a "coding set" is the subset MRT and GMA because the other codons (GCA and AGT) are contained within the first subset. Thus, ultimately, possible shortening of the chromosomes can result from the fitness function because ambiguous codons that will code for more than one of the amino acids in the diversity can be preferentially selected.

According to further embodiments of the present invention, the third and fourth parts of the fitness function are optional and their importance can be changed by a user input, such as a slider. The ability to easily vary such criteria is one of the strengths of a Genetic Algorithm according to specific embodiments of the present invention.

With a fitness score determined, one or more selection operators is used to determine how chromosomes from one generation will be used to populate the next. For example, an elitism operator is generally an operator that exactly copies some chromosomes from a current generation into a next generation. An example of a simple elitism operator directly copies the highest n % (where n=a number, such as 10, or can equal a function based, for example, on which generation is the current generation) of the current generation into the next generation. Other selection operators and/or methods are used to select parents to participate in breeding. For example, in a tournament selection method, three or more chromosomes are drawn at random from the chromosome pool. The fitness scores of these chromosomes are compared and the two chromosomes with the highest fitness scores are bred to produce one or more children.

A breeding operation is performed by applying some recombination rules to the genes of parent chromosomes to generate one or more child chromosomes, but generally without changing any of the genes/codons themselves. According to specific embodiments of the present invention, breeding is defined by determining a cross-over boundary at random for parents and creating one or more children with genes/codons from one parent up to one cross-over point and genes/codons from another parent from another cross-over point. According to specific embodiments of the present invention, crossovers only occur between genes and thus only occurs at codon boundaries. For example, consider two parents:

```
parent1: GGG GCA GTA | AGT       SEQ ID NO:2
parent2: ACA GTT AAA | CCG       SEQ ID NO:3
```

wherein the "|" character indicates a crossover position selected at random. This crossover would result in either or both of the offspring:

```
child 1: GGG GCA GTA | CCG       SEQ ID NO:4
child 2: ACA GTT AAA | AGT       SEQ ID NO:5
```

It will be apparent from the teachings herein that a variety of other breeding operations are possible. For example, only the first child need be used in the next generation, or both children can be used. Alternatively, three or more parents can be used, either with two or three or more crossover positions selected.

A genetic mutation operation, according to specific embodiments of the present invention, can be applied to some or all of the children produced after breeding or to chromosomes at some other point in the process, such as before or after selection as parents, etc. According to specific embodiments of the present invention, mutations are accomplished simply by switching one or more letters in one or more gene/codons in a chromosome. According to specific embodiments of the present invention, it is at this stage that ambiguous base codes can be added to the codons. Thus, for example, MRT might go to MRA or MAT or GRT. According to specific embodiments of the present invention, there are no rules or limitations as to which base code can be selected for a mutated base. Thus any of the fifteen commonly used base codes (e.g. A, C, T, G, R, Y, M, K, S, W, B, D, H, V, N) can be chosen at random to replace a base position selected at random on a chromosome. In alternative embodiments, various substitution rules can be defined and applied during genetic mutation operations. Thus, according to specific embodiments of the present invention, genes/codons can take on any value, they are not restricted to coding for a single amino acid, and there is no positional dependence, i.e. the positions in the chromosome do not correspond to any particular amino acid.

According to specific embodiments of the present invention, after selection and breeding operation are performed, a next generation of perhaps 1,000 chromosomes results. The Genetic Algorithm method then determines a fitness score for each chromosome in this next generation (with the option that fitness scores of chromosomes moved into the next generation through elitism are simply retained) and again performs selection, breeding, and mutation. This procedure is repeated until some type of convergence is detected. For example, in specific embodiments, convergence is detected after a number of generations (such as 10 to 15) are performed with the chromosome with the highest fitness score not changing. According to specific embodiments of the present invention, after convergence is determined, the best chromosome (e.g. the one with the highest fitness score) wins.

Figure 10:
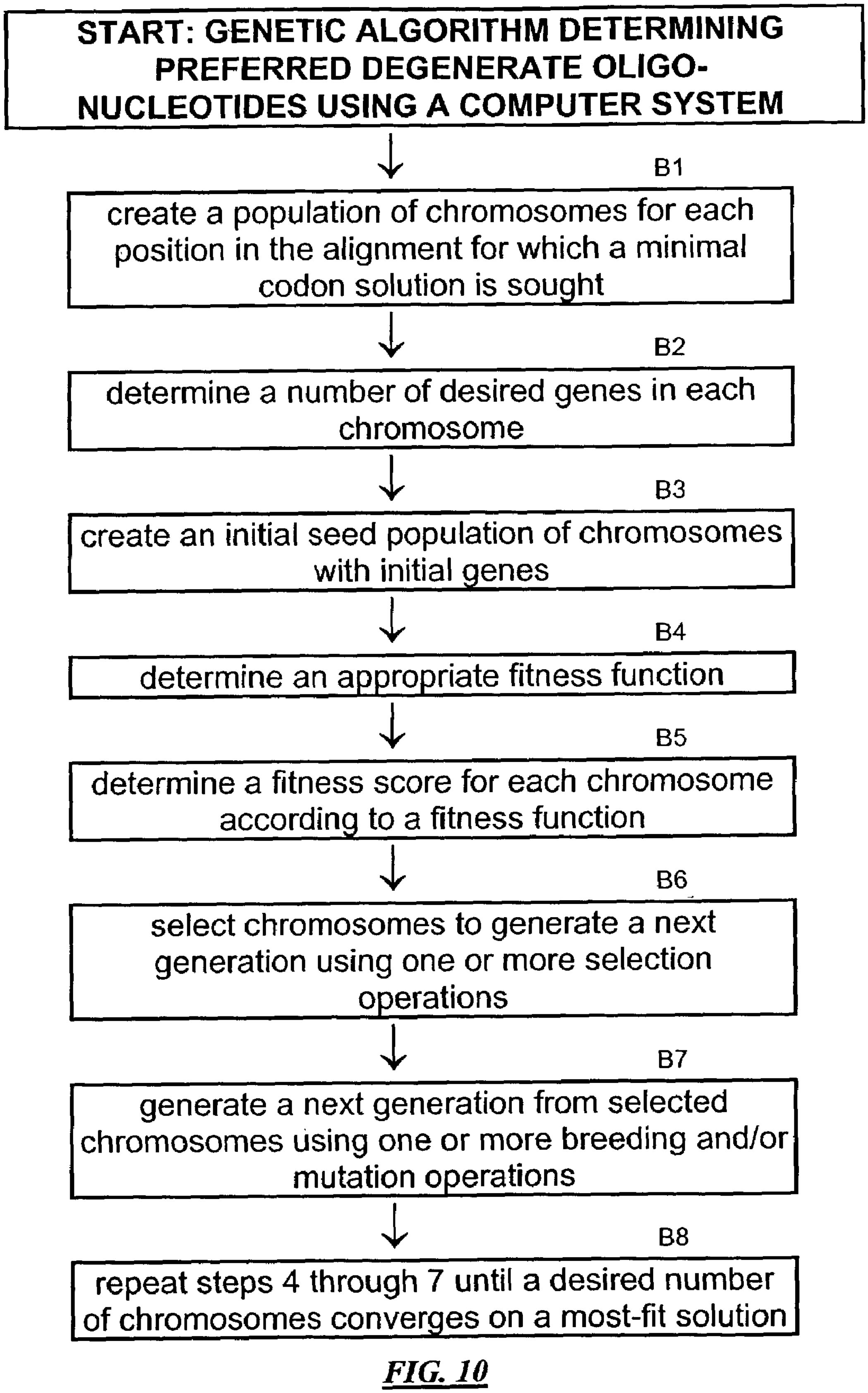
FIG. 10 is a flow chart illustrating an example genetic method according to specific embodiments of the invention.

FIG. 10 is a flow chart illustrating an example genetic method according to specific embodiments of the invention. In one embodiment, an genetic analysis method proceeds as follows: create a population of chromosomes for each position in the alignment for which a minimal codon solution is sought (Step A1); determine a number of desired genes in each chromosome (Step A2); create an initial seed population of chromosomes with initial genes (Step A3); determine an appropriate fitness function (Step A4); determine a fitness score for each chromosome according to a fitness function (Step A5); select chromosomes to generate a next generation using one or more selection operations (Step A6); generate a next generation from selected chromosomes using one or more breeding and/or mutation operations (Step A7); repeat steps 4 through 7 until a desired number of chromosomes converges on a most-fit solution (Step A8).

As described above, a number of variations in a genetic method according to specific embodiments of the present invention are possible and further variations will be understood from the teachings provided herein.

The following in a source-code listing, in Java, of an example computer source code that can be used to implement a genetic algorithm method according to specific embodiments of the present invention. Some of the supporting methods below will be understood by name and represent functions that will be clear to those familiar with the art. In this example implementation, coding for the requested amino acids is more important than not over-coding (1.0 vs. 0.5).

```
public double fitness ( )
{           HashSet aminoAcidsCodedFor = new HashSet( );
            HashSet degenCodingSet = getCodingSet( );
            int allCodonsCount = 0;
            for (Iterator degenCodonIter = degenCodingSet.iterator( );
                  degenCodonIter.hasNext( );
)     {        Symbol degenCodon = (Symbol)degenCodonIter.next( );
               HashSet nonDegenCodons = getCodonBiasTable( ).getCodonsForDCodon(degenCodon);
               allCodonsCount += nonDegenCodons.size( );
            for (Iterator nonDegenCodonIter = nonDegenCodons.iterator( );
nonDegenCodonIter.hasNext( );
)     {
            Symbol nonDegenCodon = (Symbol)nonDegenCodonIter.next( );
            aminoAcidsCodedFor.addAll(getCodonBiasTable( ).getAAsForDCodon (nonDegenCodon)
);
}        } // This constraint checks to see if all the amino acids requested are coded for by the
               current solution.
            this.codesForRequested = 1.0;
            if (!aminoAcidsCodedFor.containsAll (getInList ( ))) {
               this.codesForRequested = 0.0;
         }     // This constraint checks to see if the current solution does NOT code for more
               amino acids than requested.
            this.doesNotOvercode = 0.5;
for (Iterator codonIter = degenCodingSet.iterator( );
codonIter.hasNext( );
)     {
            Symbol codon = (Symbol)codonIter.next( );
            if (!is_codon_aalist(codon)) {
            this.doesNotOvercode = 0.0;
 break;
               }
            }
            double inSize = getInList( ).size( );
 int numDegenCodons = degenCodingSet.size( );
 this.efficiency = inSize/(inSize + numDegenCodons);
 this.codingFactor = (allCodonsCount > inSize) ?
(inSize/allCodonsCount) : 1.0;
            double result = this.codesForRequested;
 result += this.doesNotOvercode;
 result += (1.0 - getDegeneracyWeight( ))*this.codingFactor;
 result += getDegeneracyWeight( )*this.efficiency;
 return result;
            }
```

9. Scanning

In further specific embodiments, the present invention can provide for a scanning routine, at times referred to as a "scanning wizard." Scanning a protein is a technique for testing the importance of various positions in a protein in terms of function. This can be used, for example, to determine desirable directions to take in developing a protein.

Scanning according to specific embodiments of the present invention can be understood as involving a systematic replacement of residues in a protein with a certain amino acid or group of amino acids. Generally, for example, a new protein with one change is created for each scanned site. Then the new proteins are tested for function.

Alanine scanning is a common known variant where each residue in a protein is replaced with an alanine, creating N new proteins, where N is the length of the protein. Then each of the N new proteins is tested for function. If the protein has reduced or possible increased or altered function, then the replaced residue in that protein was important to function. Another reason to use scanning is to replace each position with one of a set of optimized peptides and test for added function.

According to specific embodiments of the present invention, a scanner tool can be incorporated as a wizard in a logic system of the invention. This tool, given a protein sequence, will create oligonucleotide for each of the proteins to be generated by scanning.

Figure 11:
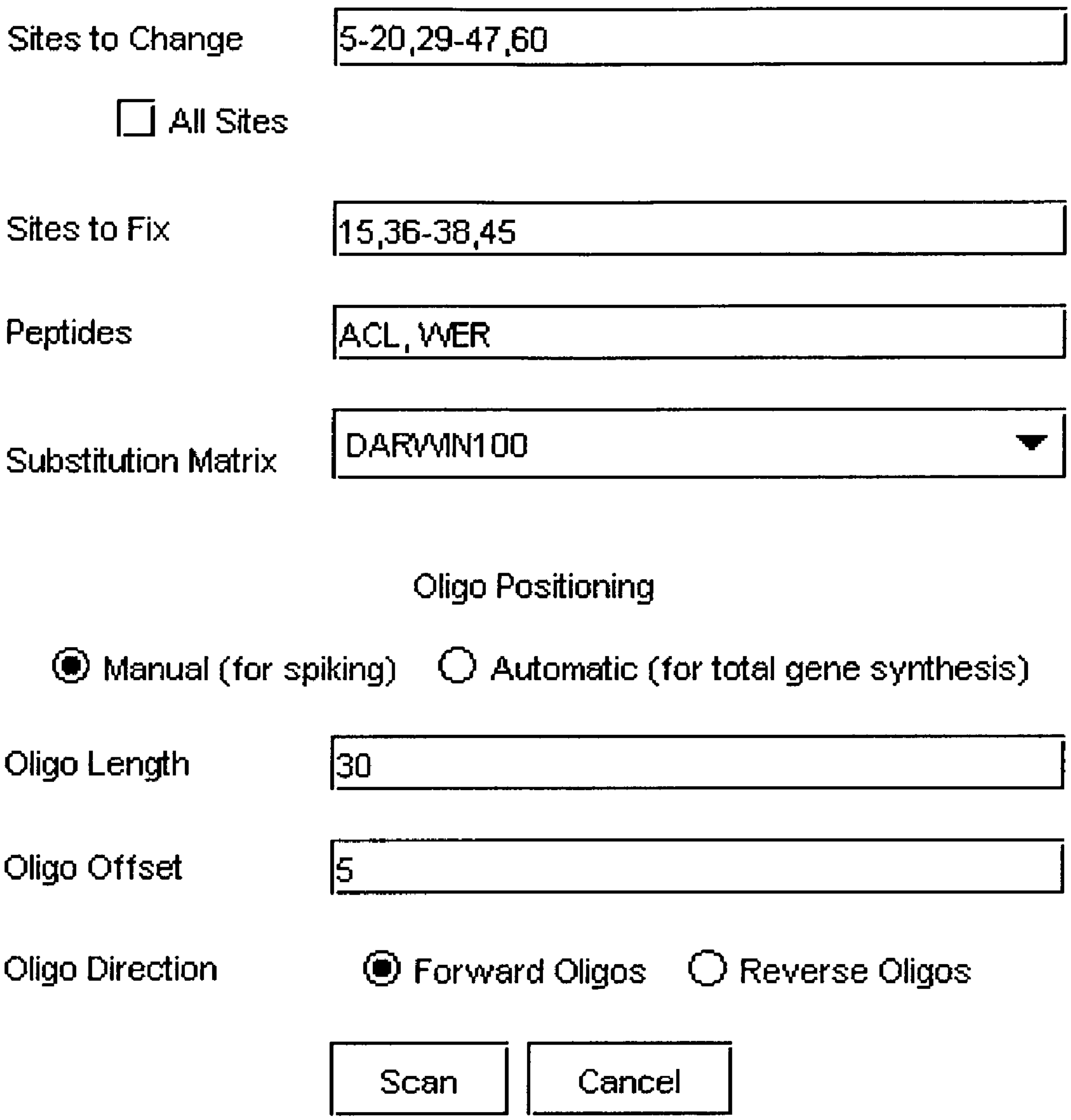
FIG. 11 illustrates an example graphical user interface providing options for a scanning tool according to specific embodiments of the present invention.

An example of options and capabilities of the tool are shown below in FIG. 11. In a particular embodiment, the tool will scan at specified sites, with the specified peptides. If more than one peptide are given, then the tool will choose which peptide is functionally closer to the original protein at each site using a substitution matrix. Two choices are given to actually create the scanned proteins, spiking the original protein, or completely synthesizing each new protein.

Figure 12:
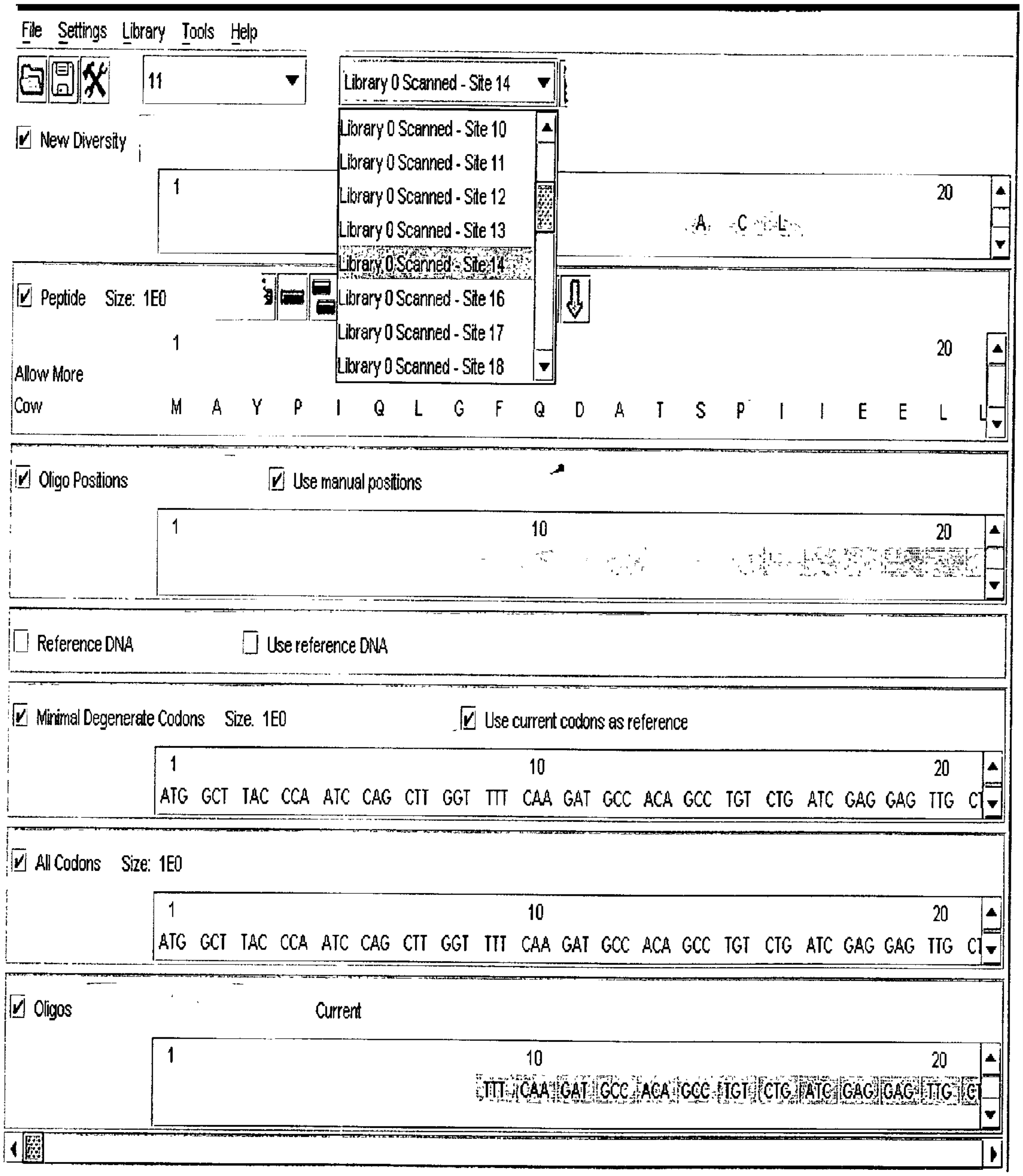
FIG. 12 illustrates an example graphical user interface providing results of scanning according to specific embodiments of the present invention. The graphical user interface depicts sequences corresponding to SEQ ID NOS: 11-13.

FIG. 12 illustrates an example of the results of scanning with the configuration in FIG. 11 and subsequently generating oligos.

10. Multiple Library Generation

According to specific embodiments of the present invention, a system according to the invention can also provide multiple library support to allow users to work with similar libraries, e.g. libraries using substantially similar peptide alignments but having different settings and diversity sizes. This allows users to share common oligonucleotide between libraries, handle similar libraries in a consistent way, and allow for the rapid, classical shuffling or recombination of clones from different libraries (owing to the similar DNA sequences).

Figure 13:
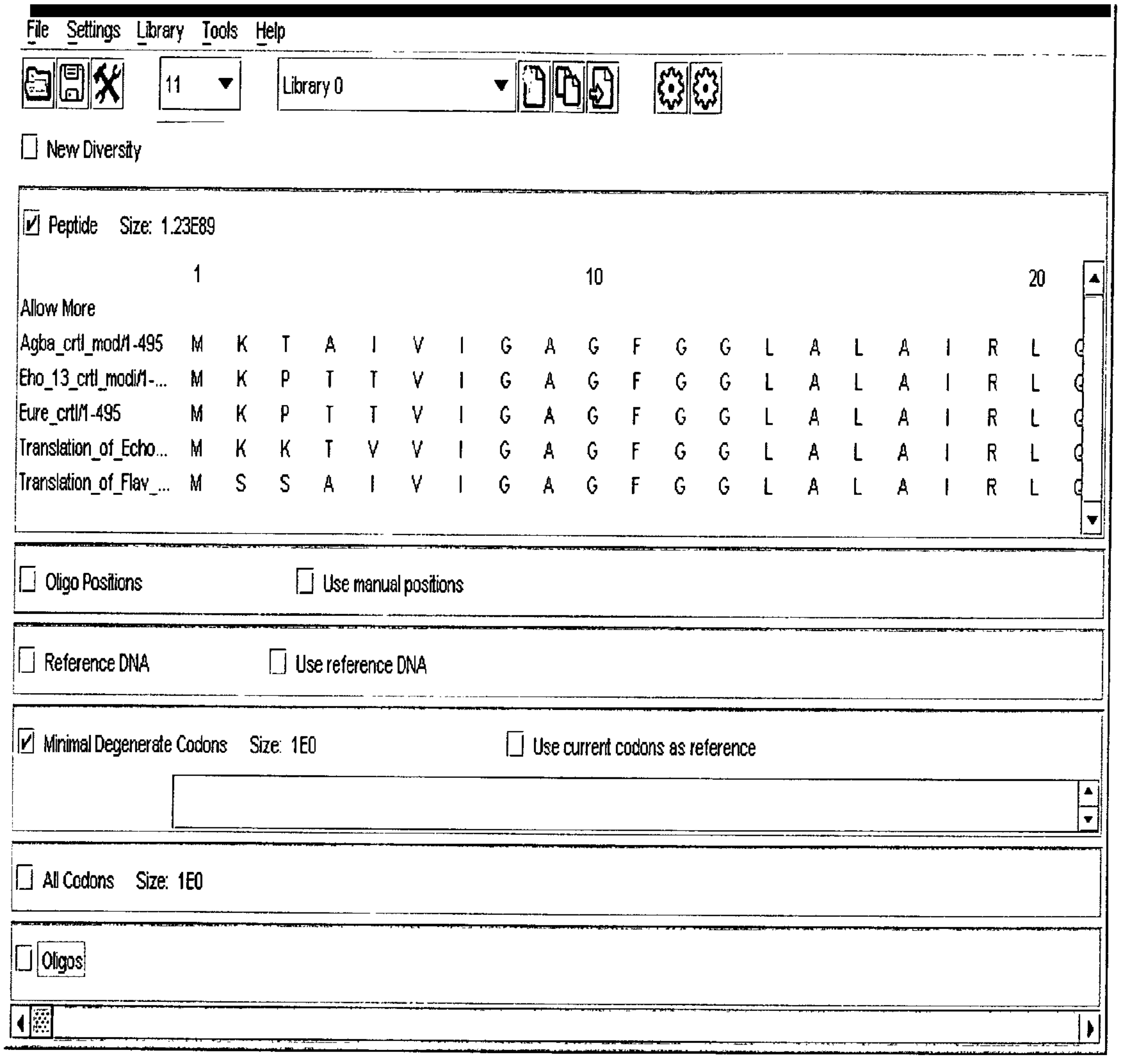
FIG. 13 illustrates an example graphical user interface showing peptide alignment whose diversity size is large according to specific embodiments of the present invention. The graphical user interface depicts sequences corresponding to SEQ ID NOS: 14-18.

In a specific embodiment, handling multiple libraries can be performed as follows:

1) Import a peptide alignment. FIG. 13 is an example of a peptide alignment whose diversity size is quite large ($1.23\times10^{89}$). Typically, the goal of creating multiple libraries is to screen a set of libraries of varying sizes that are subsets of the total diversity available.

Figure 14:
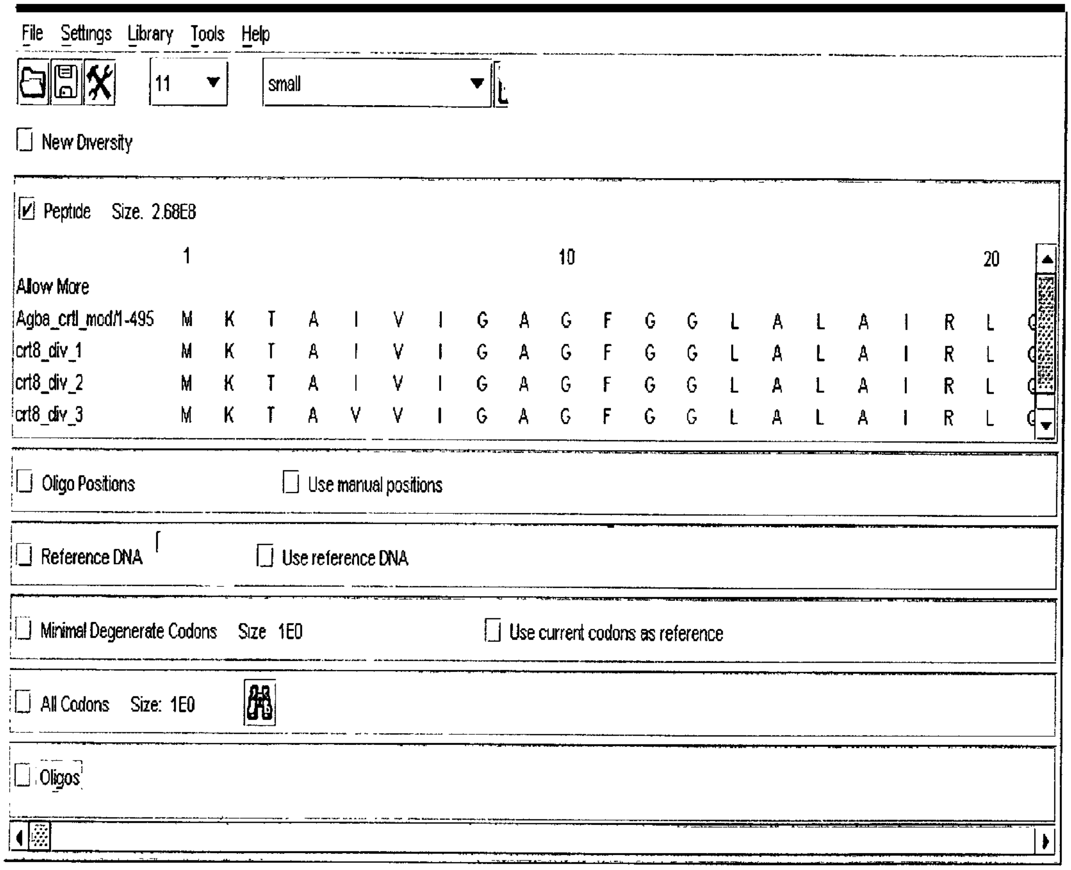
FIG. 14 illustrates an example graphical user interface showing a sample alignment generated from the diversity filter web page based on the alignment shown in FIG. 13 according to specific embodiments of the present invention. The graphical user interface depicts sequences corresponding to SEQ ID NOS: 14, 19, 20, and 21.

2) Create a new library and import a subset of the original diversity. Rename the library if desired. FIG. 14 shows a sample alignment generated from the diversity filter web page based on the alignment shown in FIG. 13 using a library size of $10^8$.

3) Select a codon usage table.

4) Adjust oligo generation parameters as desired according to provided options.

Figure 15:
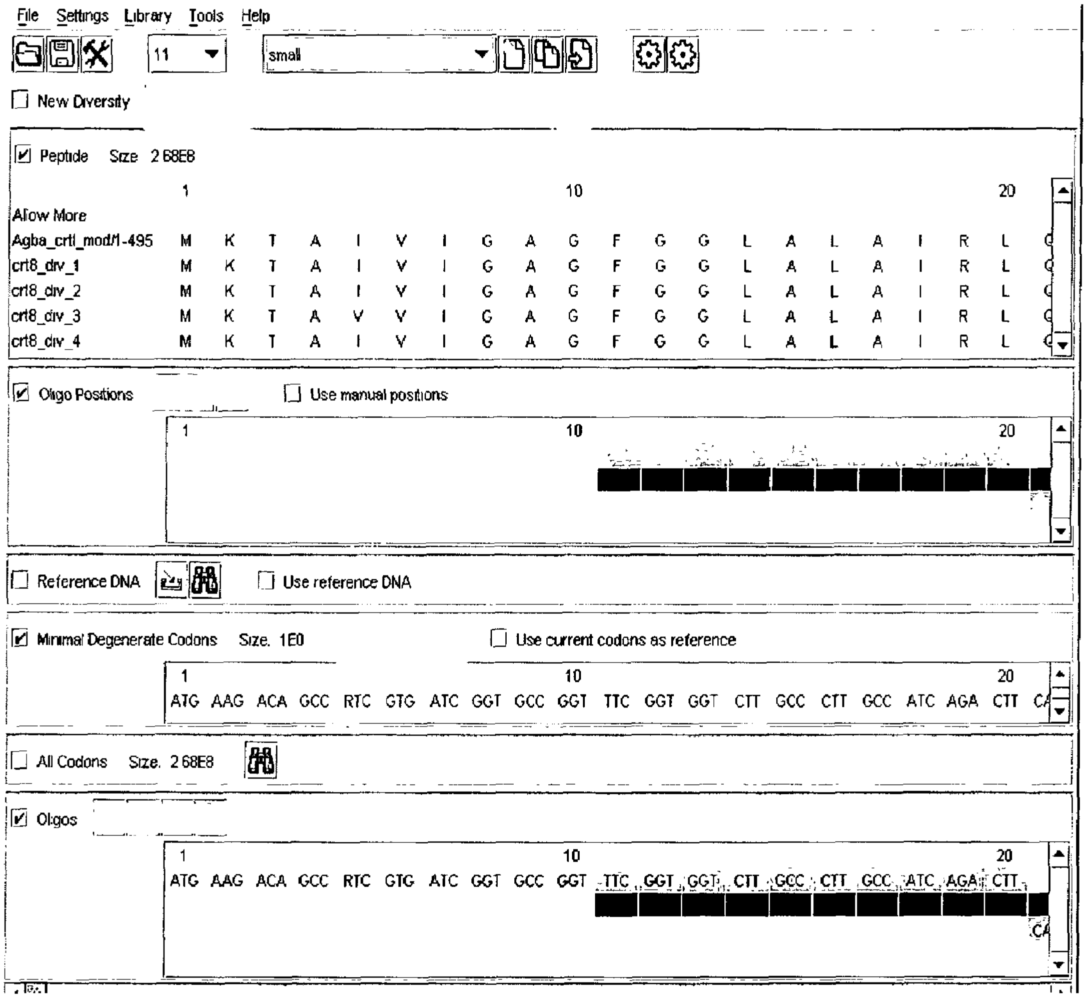
FIG. 15 illustrates an example graphical user interface showing minimal degenerate codons and oligos for a small library according to specific embodiments of the present invention. The graphical user interface depicts sequences corresponding to SEQ ID NOS: 14, 19, 20, and 21-23.

5) Create oligos for the current library by indicating 'Create Oligos' on an interface. FIG. 15 shows the minimal degenerate codons and oligos for the current library.

6) Create another library and import the peptide alignment.

7) Copy the oligo positions and minimal degenerate codons from the first library to the second one by indicating 'Copy Library Settings' provided on an interface.

8) A dialog appears prompting selection of source and destination libraries. In an example, we are copying the oligo positions and degenerate codons from a library of size $10^8$ to a new library of size $10^{12}$.

9) In the new library, check a provided indication to use manual positions.

10) In the new library, check a provided indication to use current codons as reference.

Figure 16:
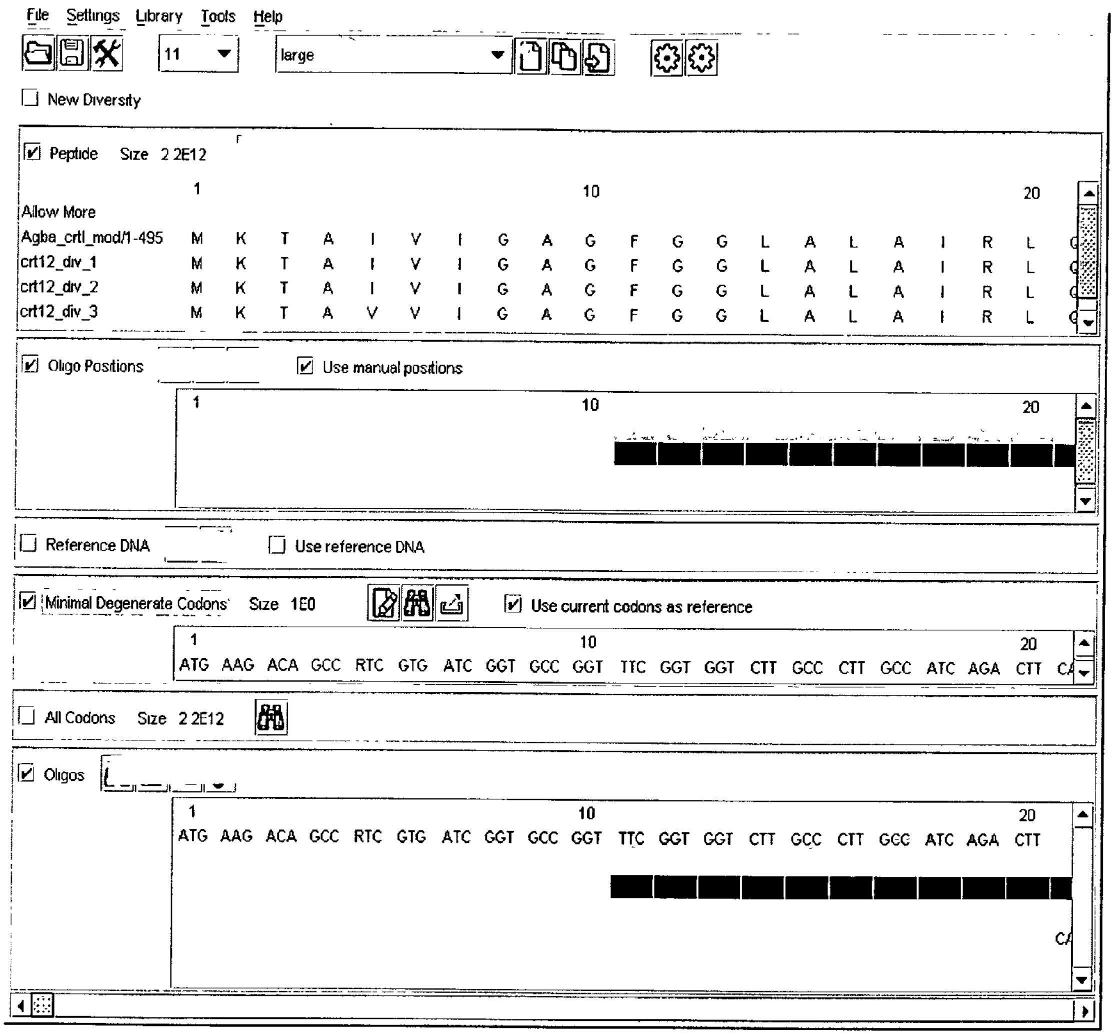
FIG. 16 illustrates an example graphical user interface showing results of oligonucleotide creation for large library minimal degenerate codons according to specific embodiments of the present invention. The graphical user interface depicts sequences corresponding to SEQ ID NOS: 14, 23, and 24-26.

11) Request creation of new oligos for this library. FIG. 16 shows the results of the oligo creation for the large library sample.

12) To order the oligos for these two libraries select a provided export all oligos menu item from the interface. In an example, among 50 total forward oligos from both libraries, only 34 are distinct.

11. General Method of Accessing Analysis Over a Network

FIG. 17A-E are flow chart illustrating methods of using a computer system to perform backtranslation, oligonucleotide identification, optionally oligonucleotide synthesis, optionally polypeptide synthesis, and optionally polypeptide screening according to specific embodiments of the invention. Such a method, performed on a server system or module in communication with a client system or module, can be described as beginning when a server module receives from a user data indicating one or more sequences (Step B1). In specific embodiments, a server can also receive indications of one or more processing options for one or more positions of sequence data (Step B2). In specific embodiments, a server can also receive indications of one or more overall processing parameters (Step B3). According to specific embodiments of the present invention, data an/or indications can be received at the server using any method for transmitting digital data, including HTML communication, FTP communication, email communication, interprocess communication, etc. In various embodiments, indications of initial data can be received from a human user using a graphical interface at a computing device, as described elsewhere herein. For example, a user may indicate a data file such as Aligned_Polypeptide.msf that contains a description of one or more polypeptide sequences and can include additional sequence data. In different embodiments, data may be submitted automatically by analysis equipment at a client site, in order to provide a desired analysis. For example, a protein analysis device that generates a polypeptide sequence data set can be programmed to forward that dataset to a server according to specific embodiments of the present invention.

Figure 17A:
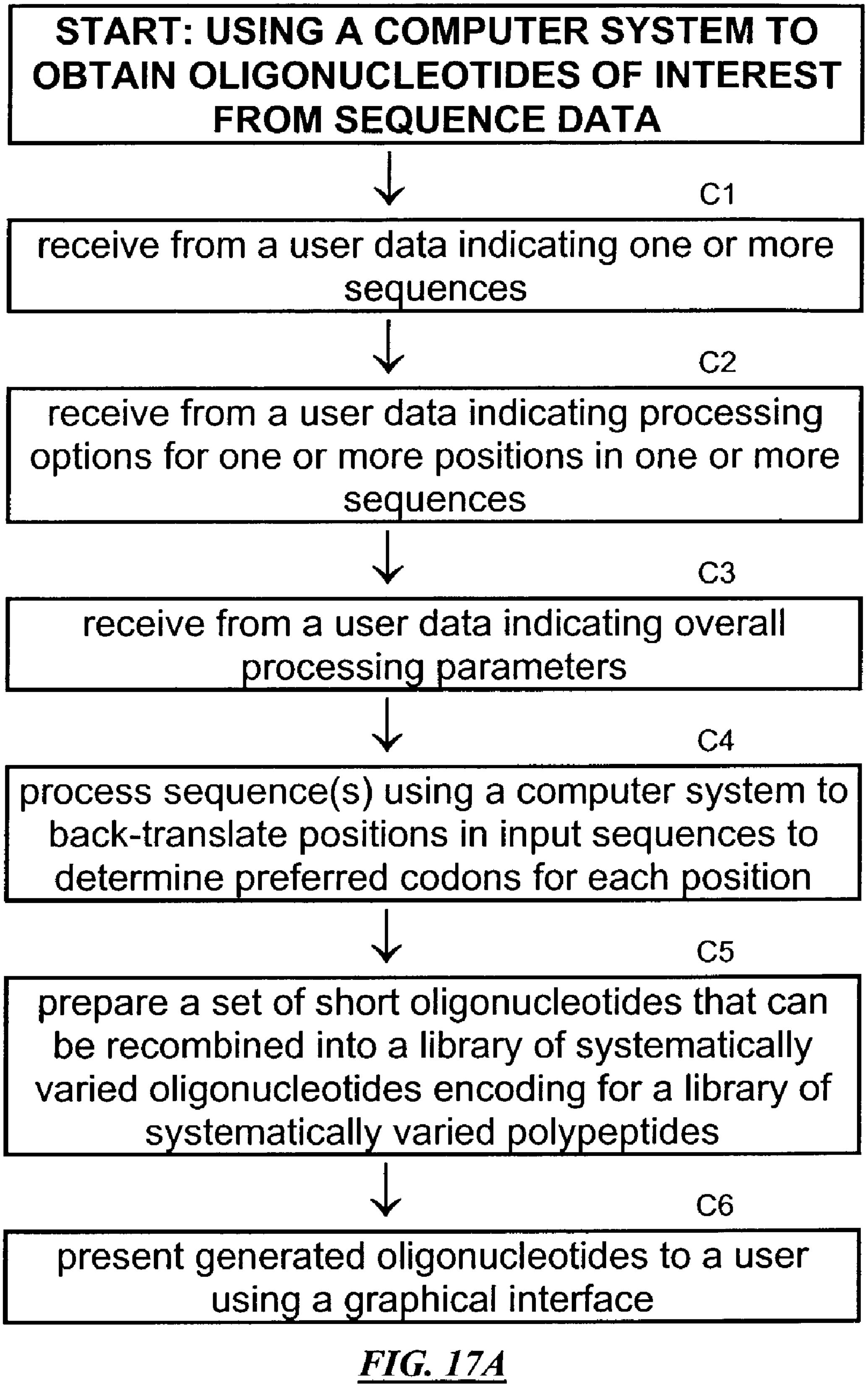
FIGS. 17A-E are flow chart illustrating methods of using a computer system to perform backtranslation, oligonucleotide identification, optionally oligonucleotide synthesis, optionally polypeptide synthesis, and optionally polypeptide screening according to specific embodiments of the invention.
Figure 17B:
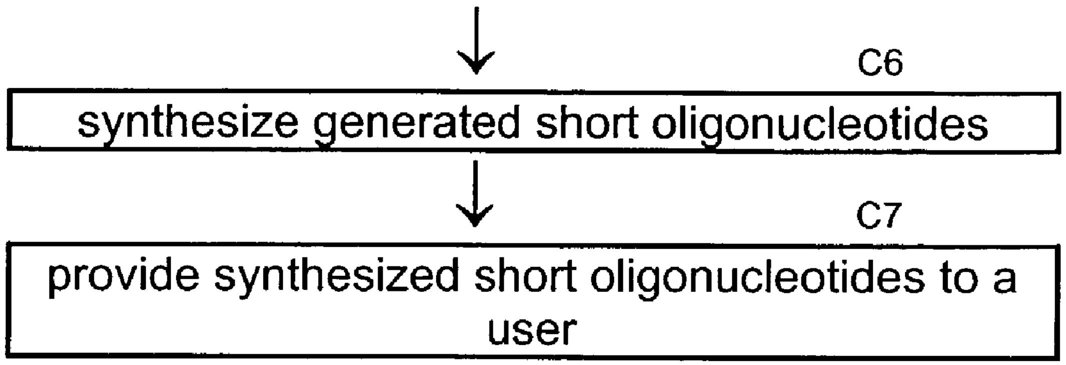
Figure 17C:
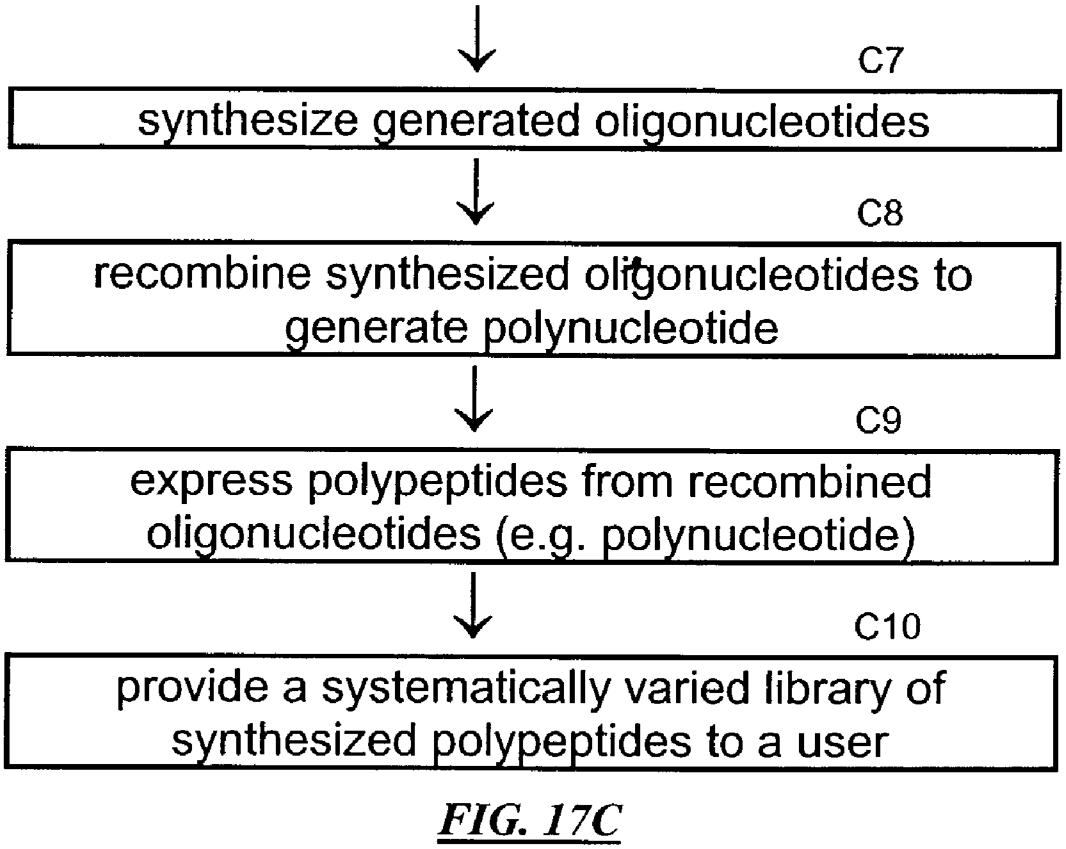
Figure 17D:
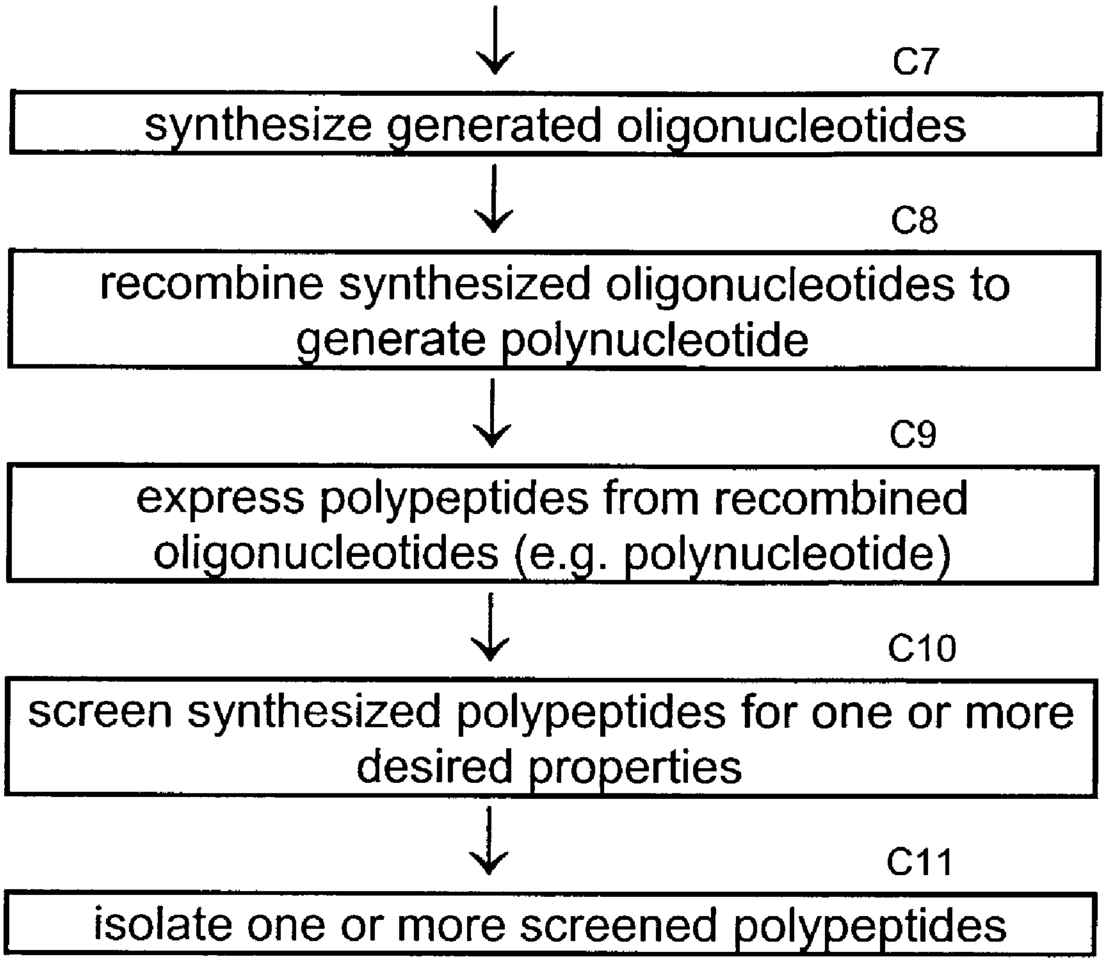
Figure 17E:
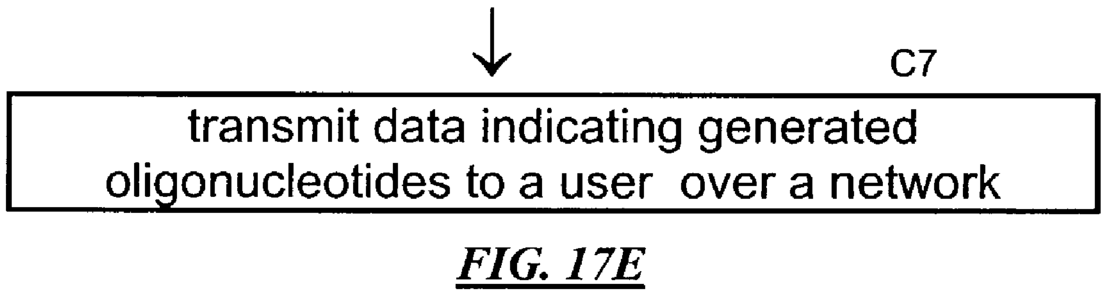

Once the request and any additional data is received at a server, it is analyzed and back-translated to determine preferred codons for each position (Step B4). From the preferred codons for each position, the server determines a set (or library) of short oligonucleotides that can be used in a recombination type reaction to generate a systematically varied library based on the initial data sequence(s) (Step B5). Once data indicating such a systematically varied library is determined, a number of delivery options are possible, as indicated in FIGS. 17A-E. For example, the results may be returned as electronic data (FIG. 17A, Step B6) that can be displayed or otherwise presented to a user or that can be used as a data file to specify oligonucleotide for synthesis. Alternatively, the data can be used at the server system to synthesize a library of oligonucleotides appropriate for recombination and that synthesized library can be delivered as specified by a user. (FIG. 17B, Steps B6 et seq.) Optionally, determined oligonucleotides can be used in a diversity generation recombination reaction to generate a systematically varied library of polypeptides and that library can be returned to a user (FIG. 17C, Steps B6 et seq.). Optionally, such polypeptides can be screening at the server system prior to being delivered as indicated by a user. (FIG. 17D, Steps B6 et seq.)

Thus, the present invention enables a method for a client user to receive oligonucleotide determining results, including recombination analysis results, over a communications network from a remote analysis system. These results can also be used to make biological molecules, or libraries of such molecules, which can be ordered by the client and delivered to the client in a physical form, such as one or more synthesized biological molecules.

12. Examples Formats for Initial Data Files and Results Data Files

Example Initial Data File Format

FIG. 18 illustrates a portion of an example of initial aligned sequence data according to specific embodiments of the invention As indicated, this aligned data input can include gaps (indicated in the figure by "-". In this example, the aligned amino acid are provided in an MSF format, but other input data formats can be accepted by specific embodiments of the invention.

Example Results Data File Format

FIG. 19 illustrates a portion of an example of backtranslation results data showing codon listings according to specific embodiments of the invention. As illustrated in the figure, this back translation data provides one non-degenerate codon for each amino acid position in the original protein.

Example Intermediate Data File Format

Figures 20, 21A:
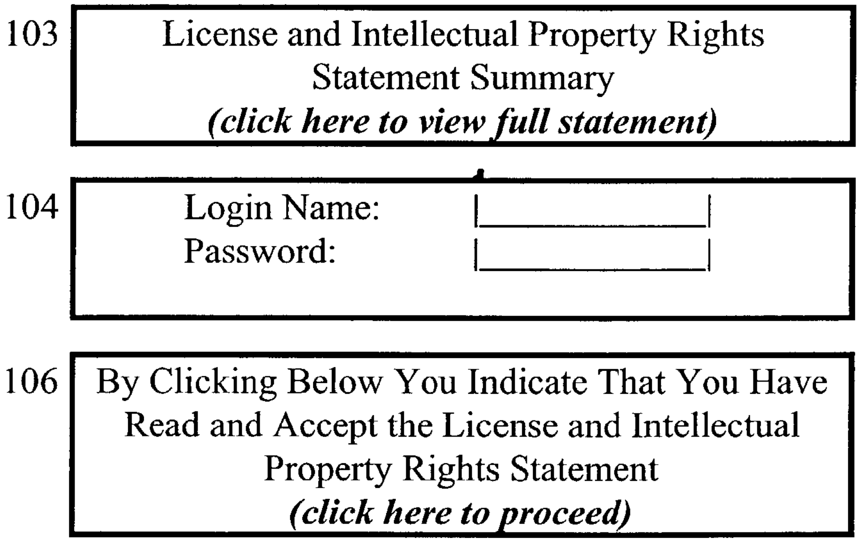

FIG. 20 illustrates a portion of an example XML data holding input data, output data, and processing options according to specific embodiments of the invention. It will be understood from the teachings provided herein that a variety of different specific file formats are possible according to specific embodiments of the present invention. In this figure, an XML file stores data regarding sequences as displayed in FIG. 4 and this storage allows a user or the system to resume a previous analysis input and/or results to allow a user to perform further processing, possibly changing one or more options and/or data inputs.

13. Additional Example Web Interface for Accessing Backtranslation Analysis Over a Network FIGS. 21A-C is a block diagram illustrating example interfaces and a process for oligonucleotide determination results according to specific embodiments of the present invention FIG. 21A illustrates the display of an example interface in the form of a Web page for inputting login information and initiation an oligonucleotide determination analysis, according to specific embodiments of the present invention. According to specific implementations and/or embodiments of the present invention, this example interface page was sent from the server system to the client system when a user accessed the server system. This example Web page contains a License and Intellectual Property Rights Statement section 103, a user identification section 104, and an proceed selection 106. One skilled in the art would appreciate that these and various other interface sections described herein can be omitted or rearranged or adapted in various ways. The 103 section provides information that identifies and describes an applicable License and Intellectual Property Rights and/or restrictions that will apply to an oligonucleotide determination operation in according to specific embodiments of the present invention. The 104 section provides a conventional capability to enter account information or payment information or login information.

FIG. 21B illustrates the display of an example interface in the form of a Web page providing additional information about a request according to specific embodiments of the present invention. As indicated, in this example interface, a user can be informed that certain intermediate data may be used to perform an analysis (such as by section 110). This data may be used according to a variety of licensing provisions, discussed further herein. Optionally a user may be given options to accept or decline such licensing provisions for use of intermediate (such as in sections 112 and 114).

FIG. 21C illustrates the display of an example interface in the form of a Web page for finally confirming a request. The confirming Web page can contain various information pertaining to an order (such as sections 120, 122, 124, and 126). This display can optionally include a confirmation indication allowing a user to make a final confirmation to proceed with the request (such as 130). For particular systems or analysis, this page may also include warnings regarding use of proprietary data or methods and can include additional license terms, such as any rights retained by the owner of the server system in either the submitted initial data, and/or the results data, and/or any intermediate data. Optionally, this final interface can allow a user to review a delivery destination and to change the delivery destination (such as 128).

Figure 22:
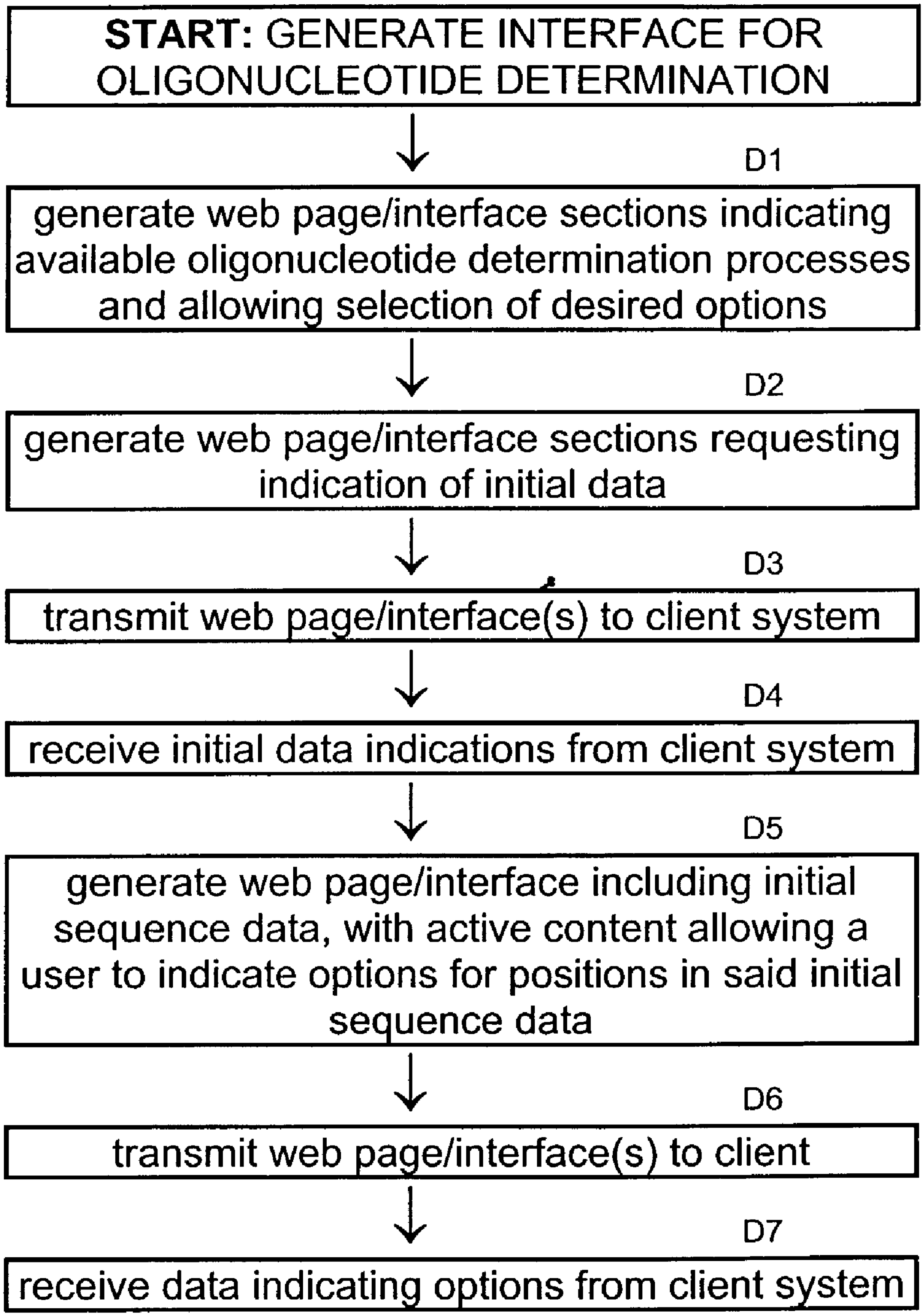
FIG. 22 is a flow diagram of a routine that enables a customer to access oligonucleotide determination services using an interface according to specific embodiments of the present invention.

FIG. 22 is a flow diagram of a routine that enables a customer to access oligonucleotide determination services using an interface according to specific embodiments of the present invention. As will be understood from the teachings herein, an example process proceeds as follows. A server system generates interface sections or portions indicating available oligonucleotide determination processes and allowing selection of desired options (Step C1). A server system also generates web page/interface sections requesting indication of initial data (Step C2). These interfaces are communicated to client device (Step C3). The server component receives initial data indications from the client device (Step C4). The server component generates one or more interfaces including initial sequence data, with active content allowing a user to indicate options for positions in said initial sequence data (Step C5). These interfaces are communicated to a client component (Step C6). The server component receives data indicating options from the client component (Step C7).

Figure 23:
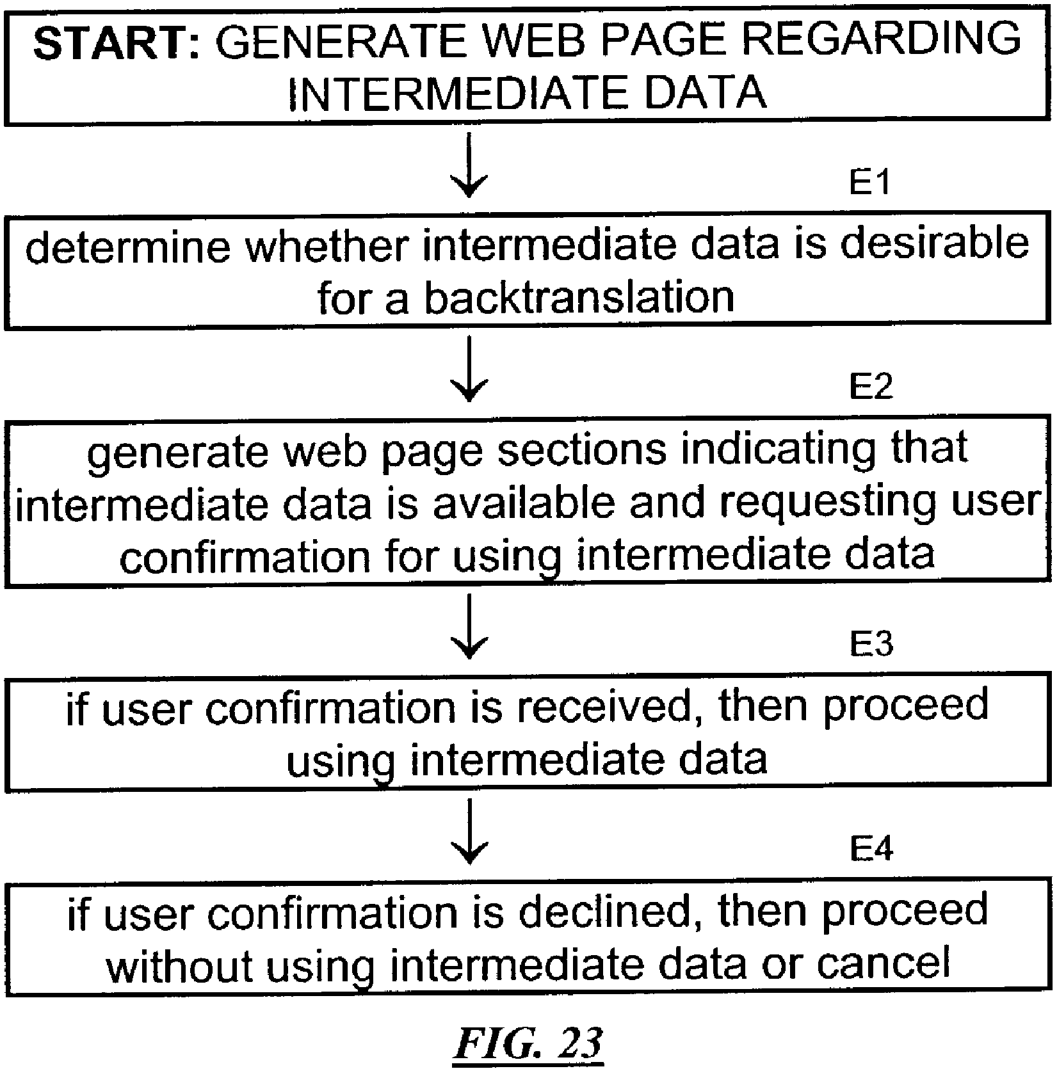
FIG. 23 is a flow diagram of a routine that enables a customer to accept or decline licensing associated with intermediate data according to specific embodiments of the present invention.

FIG. 23 is a flow diagram of a routine that enables a customer to accept or decline licensing associated with intermediate data according to specific embodiments of the present invention.

14. Example System Embodiment

Figure 24:
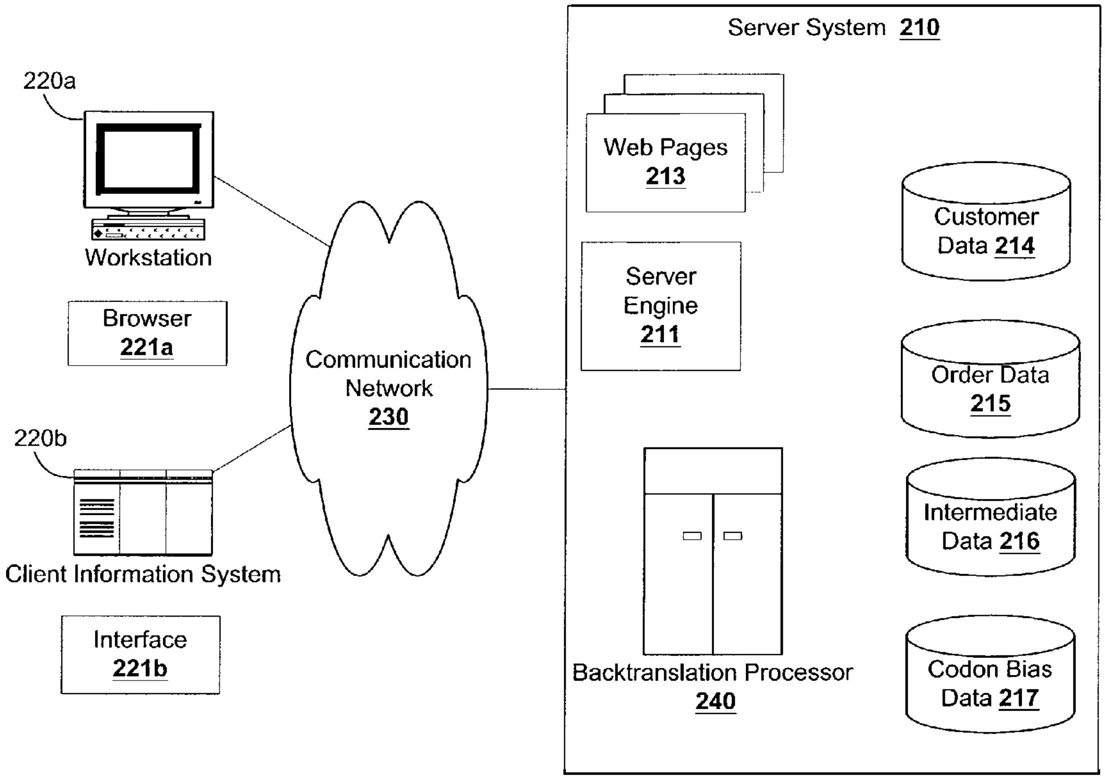
FIG. 24 is a block diagram illustrating various embodiments of the present invention as a system for ordering and delivering oligonucleotide determination or gene synthesis results.

FIG. 24 is a block diagram illustrating various embodiments of the present invention as a system for ordering and delivering oligonucleotide determination or gene synthesis results. This particular example embodiment supports providing oligonucleotide determination over the Internet. The server system 210 includes a server engine 211, various Web pages 213, an optional customer database 214, and an order tracking database 215. According to specific embodiments of the invention, the server system further includes or is in communication with a processor 240 that further comprises one or more logic modules for determining oligonucleotides and can optionally access one or more sets of intermediate data 216.

One skilled in the art would appreciate that the technique for providing biologic operations and data results can be used in various environments other than the Internet. For example, requests for oligonucleotide determination and results can also be communicated using an electronic mail environment in which initial data is indicated in an electronic mail message along with an indication of the desired analysis and/or options to be performed. Also, various communication channels may be used such as data buss connections, local area network, wide area network, or point-to-point dial up connection. Also, a server system may comprise any combination of hardware and/or software that can process requests for determining oligonucleotides in response to client requests. A client system may also comprise any combination of hardware and/or software that can interact with the server system. These systems may include digital workstation or computer systems (an example of which is shown as 220*a*) including a logic interface module (such as 221*a*) and/or various other systems or products through which data and requests can be communicated to a server system. These systems may also include laboratory-workstation-based systems (an example of which is shown as 220*b*) including a logic interface module (such as 221*b*) or various other systems or products through which data and requests can be communicated to a server system.

Although the present invention has been described in terms of various embodiments, it is not intended that the invention be limited to these embodiments. Modification within the spirit of the invention will be apparent to those skilled in the art. For example, according to specific embodiments, a server system and client system can be logic routines running on the same computer hardware system. Various different actions can be used to effect a request for an analysis. For example, a voice command may be spoken by the purchaser, a key may be depressed by the purchaser, a button on a client-side scientific device may be depressed by the user, or selection using any pointing device may be effected by the user.

15. Further Example System Embodiments

Figure 25:
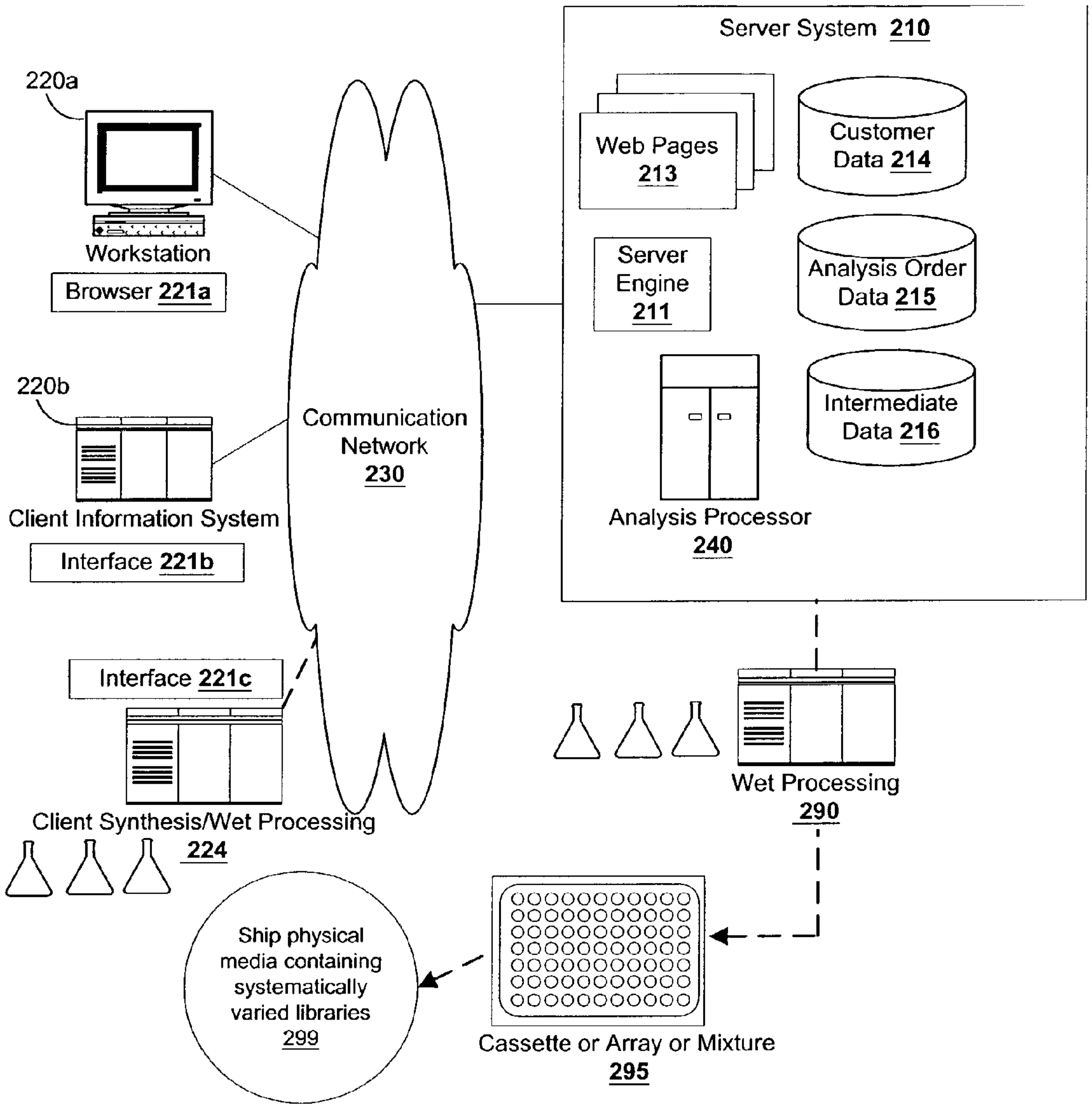
FIG. 25 is a block diagram illustrating various embodiments of the present invention as a system for ordering and delivering oligonucleotide determination or gene synthesis results further including wet or physical processing and/or delivery of a physical result.

According to further embodiments of the present invention, the invention can enable more efficient delivery of directed evolution results using in part a communications interface. FIG. 25 is a block diagram illustrating various embodiments of the present invention as a system for ordering and delivering oligonucleotide determination or gene synthesis results further including wet or physical processing and/or delivery of a physical result. According to these specific embodiments, the invention may include operation steps that may involve sequence synthesis and/or selection using a "wet" or physical processes at a server side, such as illustrated by synthesis module 290. The results of operations done on a system such as 290 can be used by server system 210 in further processing to produce a digital data result that is transmit back to client system such as 220. Alternatively, a result of a physical processing a system such as 290 can comprise an physical output, such as cassette or array or mixture 295 that can be delivered to a client as a result of an order placed using a communication network.

In a further example embodiment, a server system 210 can transmit digital results to a client physical processing system, such as 224, for some type of physical processing by such a systems. Such digital data can be provided whether or not any physical processing is done at the server side.

While some related services may have previously been provided by, for example, scientific consulting institutions, typically these services have involved considerable expense and have been arranged and engaged on a specific and individual basis. Using the teachings provided herein, the present invention, according to specific embodiments, provides a method allowing customers to more easily order a directed evolution service or directed evolution product and can allow a service provider to provide such services at substantially reduced costs.

According to specific embodiments of the present invention, a number of physical products can be provided to customers using the teachings provided herein, including such things as biological molecules, arrays or cassettes containing multiple molecules or groups of libraries of molecules, etc.

16. Embodiment in a Programmed Information Appliance

Figure 26:
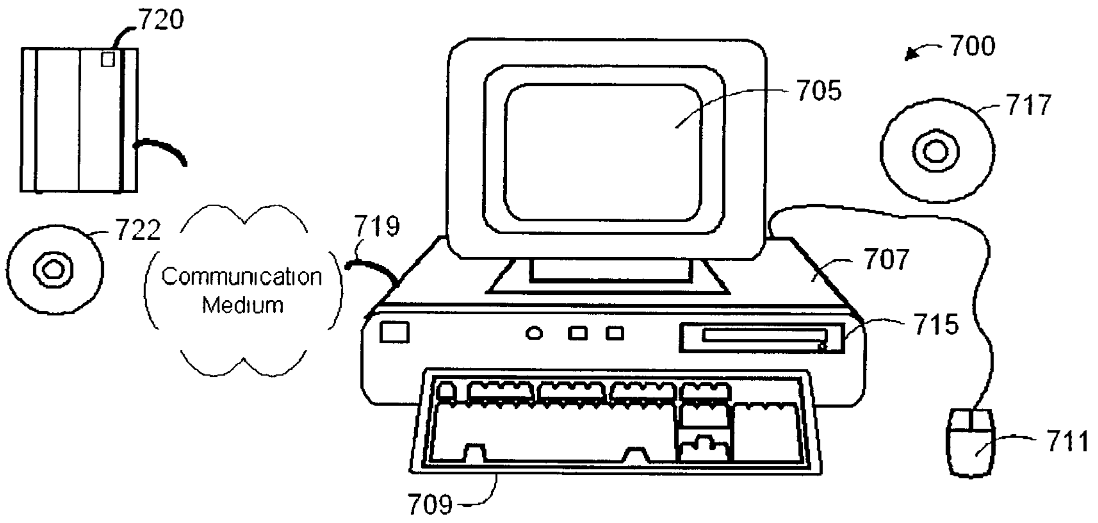
FIG. 26 is a block diagram showing an example logic device in which various aspects of the present invention may be embodied.

FIG. 26 is a block diagram showing an example logic device in which various aspects of the present invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 26 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional display 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

17. Other Embodiments

The invention has now been described with reference to specific embodiments. Other embodiments will be apparent to those of skill in the art. In particular, a user information appliance has generally been illustrated as a personal computer. However, the digital computing device is meant to be any information appliance for interacting with a data application, and could include such devices as a digitally enabled television, cell phone, personal digital assistant, information enabled laboratory systems, etc. In addition, communication channels have generally been described as traditional digital network connections, with the appropriate corresponding hardware and software. However, channels are meant to be any channels capable of carrying data, including wireless channels, optical channels, electrical channels, telephone lines, publicly accessible data networks and internetwork, private data networks, or data communications occurring between components in an information system.

As a further embodiment, it will be understood from the teachings herein that it is possible to start with a nucleotide sequence, forward translate and then proceed as described herein. Additionally, according to further embodiments of the present invention, the same type of analysis could be performed only on DNA, e.g. still attempting to create the minimal set of oligos, but possibly using a slightly different scoring function, e.g. creating all the crossovers, but use the codons supplied from the DNA sequence.

It is understood that the examples and embodiments described herein are for illustrative purposes and that various modifications or changes in light thereof will be suggested by the teachings herein to persons skilled in the art and are to be included within the spirit and purview of this application and scope of the claims. All publications, patents, patent applications or other documents cited herein or filed with this application, including any references filed as part of an Information Disclosure Statement, are incorporated by reference in their entirety.

What is claimed:

1. A method of providing degenerate oligonucleotide data using one or more logic processing systems, the method comprising:

receiving one or more indications of initial digital data from a user, said initial digital data indicating one or more polypeptide input sequences;

receiving options digital data from the user, said options data indicating one or more processing and/or input and/or output options for said sequences;

backtranslating said one or more polypeptide input sequences using one or more of said logic processing systems to create a set of backtranslated oligonucleotides;

using one or more items of said options digital data to affect said backtranslating, said options digital data affecting said backtranslating by specifying or varying input and/or output and/or processing of said backtranslating;

determining a set of degenerate oligonucleotides from said set of backtranslated oligonucleotides;

recombining and forward translating said set of degenerate oligonucleotides to produce systematically varied libraries of said one or more polypeptide input sequences; and transmitting, using one or more of said systems, digital data representing said set of degenerate oligonucleotides to the user.

2. The method of claim 1 further comprising:

after receiving said indications of initial digital data indicating one or more polypeptide input sequences, generating one or more user interfaces including indications allowing the user to specify positional options data regarding positions in one or more of said input sequences;

presenting said one or more interfaces to the user; and registering user actions indicating the positional options data regarding said one or more positions.

3. The method of claim 2 wherein:

said receiving and said transmitting are performed over a communications network;

said receiving and said transmitting are performed between a client system and a server system;

said backtranslating is performed under control of said server system;

said determining is performed under control of said server system;

said transmitting is performed under control of said server system;

said presenting is performed under control of said client system; and said registering is performed under control of said client system.

4. The method of claim 1 wherein said receiving and said transmitting are performed over a communications network.

5. The method of claim 4 wherein said receiving and said transmitting are performed between a client system and a server system.

6. The method of claim 1 wherein said initial digital data comprises data representing two or more aligned polypeptide sequences.

7. The method of claim 1 wherein said initial digital data comprises data representing two or more unaligned polypeptide sequences and further comprising using an alignment algorithm to align said sequences.

8. The method of claim 1 further comprising:

during said backtranslating and/or said determining, accessing one or more analysis routines, wherein the details of operation of said analysis routines are not revealed to the user.

9. The method of claim 1 further comprising:

during said backtranslating and/or said determining, accessing one or more sets of intermediate data, wherein said intermediate data are not revealed to the user.

10. The method of claim 1 wherein said method is performed entirely on one or more information processing devices, with no in-vitro or in-vivo analysis or synthesis steps.

11. The method of claim 1 further comprising:

at said one or more logic processing systems ensuring that said initial digital data is kept secret and is not accessible to any operators of said computer system.

12. The method of claim 1 further comprising producing one or more nucleic acids by in vitro recombination, which nucleic acids are encoded using said transmitted data to synthesize.

13. The method of claim 1, wherein transmitting digital data representing said set of degenerate oligonucleotides to the user comprises displaying on a display said set of degenerate oligonucleotides.

14. The method of claim 1, wherein said recombining is performed digitally.

15. The method of claim 1, further comprising transmitting, using one or more of said systems, digital data representing said systematically varied libraries to the user.

16. A method of providing minimum degenerate oligonucleotides, the method comprising:

receiving one or more indications of initial digital data from a user at one or more of logic processing systems, said initial digital data indicating one or more polypeptide sequences;

receiving options digital data from the user at one or more of said systems, said options data indicating one or more processing options for said one or more polypeptide sequences;

backtranslating said one or more polypeptide sequences using one or more of said systems;

digitally determining using one or more of said systems a set of degenerate oligonucleotides;

recombining and forward translating to produce systematically varied libraries of said one or more polypeptide sequences or related polypeptides;

delivering a synthesized product to the user.

17. The method of claim 16 wherein said synthesized product comprises a library of synthesized oligonucleotides corresponding to said digitally determined set.

18. The method of claim 16 wherein said synthesized product comprises a library of synthesized oligonucleotides corresponding to said digitally determined set, with further characteristics of said library selected to facilitate physically recombining and combining said library.

19. The method of claim 16 further comprising:

performing a recombination reaction using said synthesized oligonucleotides;

translating the products of said recombination reaction to a plurality of polypeptide sequences that are systematically varied as a result of prior steps; and wherein said synthesized product comprises a library of said systematically varied polypeptide sequences.

20. The method of claim 16 further comprising:

performing a recombination reaction using said synthesized oligonucleotides;

translating the products of said recombination reaction to a plurality of polypeptide sequences that are systematically varied as a result of prior steps;

selecting from said plurality of systematically varied polypeptide sequences for a desired sequence characteristic;

wherein said synthesized product comprises one or more selected polypeptide sequences.

* * * * *

SEQUENCE LISTING

```
<160> NUMBER OF SEQ ID NOS: 42

<210> SEQ ID NO 1
<211> LENGTH: 12
<212> TYPE: DNA
<213> ORGANISM: Artificial Sequence
<220> FEATURE:
<223> OTHER INFORMATION: Computer generated

<400> SEQUENCE: 1

mrtgcagmaa gt                                                        12


<210> SEQ ID NO 2
<211> LENGTH: 12
<212> TYPE: DNA
<213> ORGANISM: Artificial Sequence
<220> FEATURE:
<223> OTHER INFORMATION: Computer generated

<400> SEQUENCE: 2

ggggcagtaa gt                                                        12


<210> SEQ ID NO 3
<211> LENGTH: 12
<212> TYPE: DNA
<213> ORGANISM: Artificial Sequence
<220> FEATURE:
<223> OTHER INFORMATION: Computer generated

<400> SEQUENCE: 3

acagttaaac cg                                                        12


<210> SEQ ID NO 4
<211> LENGTH: 12
<212> TYPE: DNA
<213> ORGANISM: Artificial Sequence
<220> FEATURE:
<223> OTHER INFORMATION: Computer generated

<400> SEQUENCE: 4

ggggcagtac cg                                                        12


<210> SEQ ID NO 5
<211> LENGTH: 12
<212> TYPE: DNA
<213> ORGANISM: Artificial Sequence
<220> FEATURE:
<223> OTHER INFORMATION: Computer generated

<400> SEQUENCE: 5
```

-continued acagttaaaa gt 12

<210> SEQ ID NO 6
<211> LENGTH: 14
<212> TYPE: PRT
<213> ORGANISM: Artificial Sequence
<220> FEATURE:
<223> OTHER INFORMATION: Computer generated

<400> SEQUENCE: 6

Trp Ser Gly Asp Asp Asn Ser Ala Lys His Val Arg Gly Glu
1 5 10

<210> SEQ ID NO 7
<211> LENGTH: 14
<212> TYPE: PRT
<213> ORGANISM: Artificial Sequence
<220> FEATURE:
<223> OTHER INFORMATION: Computer generated

<400> SEQUENCE: 7

Trp Thr Gly Asp Asp Thr Ser Ala Ala His Val Arg Gly Asn
1 5 10

<210> SEQ ID NO 8
<211> LENGTH: 14
<212> TYPE: PRT
<213> ORGANISM: Artificial Sequence
<220> FEATURE:
<223> OTHER INFORMATION: Computer generated

<400> SEQUENCE: 8

Trp Thr Gly Asp Asp Thr Ser Ala Ala His Val Arg Gly Asn
1 5 10

<210> SEQ ID NO 9
<211> LENGTH: 42
<212> TYPE: DNA
<213> ORGANISM: Artificial Sequence
<220> FEATURE:
<223> OTHER INFORMATION: Computer generated

<400> SEQUENCE: 9
agtaggactg gaaatrgcgg cactaagtgt agatcacact gt 42

<210> SEQ ID NO 10
<211> LENGTH: 12
<212> TYPE: DNA
<213> ORGANISM: Artificial Sequence
<220> FEATURE:
<223> OTHER INFORMATION: Computer generated

<400> SEQUENCE: 10
tctgacgacc ag 12

<210> SEQ ID NO 11
<211> LENGTH: 21
<212> TYPE: PRT
<213> ORGANISM: Artificial Sequence
<220> FEATURE:
<223> OTHER INFORMATION: Computer generated

<400> SEQUENCE: 11

Met Ala Tyr Pro Ile Gln Leu Gly Phe Gln Asp Ala Thr Ser Pro Ile
1 5 10 15

Ile Glu Glu Leu Leu

-continued

20

<210> SEQ ID NO 12
<211> LENGTH: 62
<212> TYPE: DNA
<213> ORGANISM: Artificial Sequence
<220> FEATURE:
<223> OTHER INFORMATION: Computer generated

<400> SEQUENCE: 12
atggcttacc caatccagct tggttttcaa gatgccacag cctgtctgat cgaggagttg 60
ct 62

<210> SEQ ID NO 13
<211> LENGTH: 38
<212> TYPE: DNA
<213> ORGANISM: Artificial Sequence
<220> FEATURE:
<223> OTHER INFORMATION: Computer generated

<400> SEQUENCE: 13
tttcaagatg ccacagcctg tctgatcgag gagttgct 38

<210> SEQ ID NO 14
<211> LENGTH: 21
<212> TYPE: PRT
<213> ORGANISM: Artificial Sequence
<220> FEATURE:
<223> OTHER INFORMATION: Computer generated

<400> SEQUENCE: 14

Met Lys Thr Ala Ile Val Ile Gly Ala Gly Phe Gly Gly Leu Ala Leu
1 5 10 15

Ala Ile Arg Leu Gln
20

<210> SEQ ID NO 15
<211> LENGTH: 21
<212> TYPE: PRT
<213> ORGANISM: Artificial Sequence
<220> FEATURE:
<223> OTHER INFORMATION: Computer generated

<400> SEQUENCE: 15

Met Lys Pro Thr Thr Val Ile Gly Ala Gly Phe Gly Gly Leu Ala Leu
1 5 10 15

Ala Ile Arg Leu Gln
20

<210> SEQ ID NO 16
<211> LENGTH: 21
<212> TYPE: PRT
<213> ORGANISM: Artificial Sequence
<220> FEATURE:
<223> OTHER INFORMATION: Computer generated

<400> SEQUENCE: 16

Met Lys Pro Thr Thr Val Ile Gly Ala Gly Phe Gly Gly Leu Ala Leu
1 5 10 15

Ala Ile Arg Leu Gln
20

<210> SEQ ID NO 17
<211> LENGTH: 21

<212> TYPE: PRT
<213> ORGANISM: Artificial Sequence
<220> FEATURE:
<223> OTHER INFORMATION: Computer generated

<400> SEQUENCE: 17

```
Met Lys Lys Thr Val Val Ile Gly Ala Gly Phe Gly Gly Leu Ala Leu
 1               5                  10                  15

Ala Ile Arg Leu Gln
            20
```

<210> SEQ ID NO 18
<211> LENGTH: 21
<212> TYPE: PRT
<213> ORGANISM: Artificial Sequence
<220> FEATURE:
<223> OTHER INFORMATION: Computer generated

<400> SEQUENCE: 18

```
Met Ser Ser Ala Ile Val Ile Gly Ala Gly Phe Gly Gly Leu Ala Leu
 1               5                  10                  15

Ala Ile Arg Leu Gln
            20
```

<210> SEQ ID NO 19
<211> LENGTH: 21
<212> TYPE: PRT
<213> ORGANISM: Artificial Sequence
<220> FEATURE:
<223> OTHER INFORMATION: Computer generated

<400> SEQUENCE: 19

```
Met Lys Thr Ala Ile Val Ile Gly Ala Gly Phe Gly Gly Leu Ala Leu
 1               5                  10                  15

Ala Ile Arg Leu Gln
            20
```

<210> SEQ ID NO 20
<211> LENGTH: 21
<212> TYPE: PRT
<213> ORGANISM: Artificial Sequence
<220> FEATURE:
<223> OTHER INFORMATION: Computer generated

<400> SEQUENCE: 20

```
Met Lys Thr Ala Ile Val Ile Gly Ala Gly Phe Gly Gly Leu Ala Leu
 1               5                  10                  15

Ala Ile Arg Leu Gln
            20
```

<210> SEQ ID NO 21
<211> LENGTH: 21
<212> TYPE: PRT
<213> ORGANISM: Artificial Sequence
<220> FEATURE:
<223> OTHER INFORMATION: Computer generated

<400> SEQUENCE: 21

```
Met Lys Thr Ala Val Val Ile Gly Ala Gly Phe Gly Gly Leu Ala Leu
 1               5                  10                  15

Ala Ile Arg Leu Gln
            20
```

<210> SEQ ID NO 22

-continued

<211> LENGTH: 21
<212> TYPE: PRT
<213> ORGANISM: Artificial Sequence
<220> FEATURE:
<223> OTHER INFORMATION: Computer generated

<400> SEQUENCE: 22

Met Lys Thr Ala Ile Val Ile Gly Ala Gly Phe Gly Gly Leu Ala Leu
1 5 10 15

Ala Ile Arg Leu Gln
20

<210> SEQ ID NO 23
<211> LENGTH: 62
<212> TYPE: DNA
<213> ORGANISM: Artificial Sequence
<220> FEATURE:
<223> OTHER INFORMATION: Computer generated

<400> SEQUENCE: 23
atgaagacag ccrtcgtgat cggtgccggt ttcggtggtc ttgcccttgc catcagactt 60
ca 62

<210> SEQ ID NO 24
<211> LENGTH: 21
<212> TYPE: PRT
<213> ORGANISM: Artificial Sequence
<220> FEATURE:
<223> OTHER INFORMATION: Computer generated

<400> SEQUENCE: 24

Met Lys Thr Ala Ile Val Ile Gly Ala Gly Phe Gly Gly Leu Ala Leu
1 5 10 15

Ala Ile Arg Leu Gln
20

<210> SEQ ID NO 25
<211> LENGTH: 21
<212> TYPE: PRT
<213> ORGANISM: Artificial Sequence
<220> FEATURE:
<223> OTHER INFORMATION: Computer generated

<400> SEQUENCE: 25

Met Lys Thr Ala Ile Val Ile Gly Ala Gly Phe Gly Gly Leu Ala Leu
1 5 10 15

Ala Ile Arg Leu Gln
20

<210> SEQ ID NO 26
<211> LENGTH: 21
<212> TYPE: PRT
<213> ORGANISM: Artificial Sequence
<220> FEATURE:
<223> OTHER INFORMATION: Computer generated

<400> SEQUENCE: 26

Met Lys Thr Ala Val Val Ile Gly Ala Gly Phe Gly Gly Leu Ala Leu
1 5 10 15

Ala Ile Arg Leu Gln
20

<210> SEQ ID NO 27
<211> LENGTH: 26

-continued

<212> TYPE: PRT
<213> ORGANISM: Artificial Sequence
<220> FEATURE:
<223> OTHER INFORMATION: Computer generated

<400> SEQUENCE: 27

Met Leu Thr Trp Ser Asp Asp Asn Lys Cys Arg Ser Gly Ala Lys Gly
1 5 10 15

Lys Trp Lys Cys Phe Cys Tyr Phe Asn Cys
20 25

<210> SEQ ID NO 28
<211> LENGTH: 28
<212> TYPE: PRT
<213> ORGANISM: Artificial Sequence
<220> FEATURE:
<223> OTHER INFORMATION: Computer generated

<400> SEQUENCE: 28

Met Leu Cys Glu Thr Trp Thr Cys Asp Thr Gln Cys Lys Ser Gly Ala
1 5 10 15

Ala Gly Lys Trp Met Cys Phe Cys Tyr Phe Asn Cys
20 25

<210> SEQ ID NO 29
<211> LENGTH: 33
<212> TYPE: PRT
<213> ORGANISM: Artificial Sequence
<220> FEATURE:
<223> OTHER INFORMATION: Computer generated

<400> SEQUENCE: 29

Met Leu Cys Glu Lys Ala Ser Thr Trp Thr Cys Asp Thr Lys Cys Arg
1 5 10 15

Ser Trp Glu Gly Ala Ala Gly Lys His Met Cys Phe Cys Tyr Phe Asn
20 25 30

Cys

<210> SEQ ID NO 30
<211> LENGTH: 34
<212> TYPE: PRT
<213> ORGANISM: Artificial Sequence
<220> FEATURE:
<223> OTHER INFORMATION: Computer generated

<400> SEQUENCE: 30

Glu Leu Cys Glu Lys Ala Ser Arg Thr Trp Ser Asp Asp Asn Lys Cys
1 5 10 15

Arg Ser Trp Glu Gly Ala Lys Gly Lys Trp Lys Cys Phe Cys Tyr Phe
20 25 30

Asn Cys

<210> SEQ ID NO 31
<211> LENGTH: 34
<212> TYPE: PRT
<213> ORGANISM: Artificial Sequence
<220> FEATURE:
<223> OTHER INFORMATION: Computer generated

<400> SEQUENCE: 31

Asn Leu Cys Glu Lys Ala Ser Leu Thr Trp Thr Cys Asp Thr Gln Cys
1 5 10 15

Lys Ser Trp Glu Gly Ala Ala Gly Lys Trp Met Cys Phe Cys Tyr Phe

-continued

```
            20                  25                  30

Asn Cys


<210> SEQ ID NO 32
<211> LENGTH: 34
<212> TYPE: PRT
<213> ORGANISM: Artificial Sequence
<220> FEATURE:
<223> OTHER INFORMATION: Computer generated

<400> SEQUENCE: 32

Asn Leu Cys Glu Lys Ala Ser Leu Thr Trp Thr Cys Asp Thr Lys Cys
 1               5                  10                  15

Arg Ser Trp Glu Gly Ala Ala Gly Lys His Met Cys Phe Cys Tyr Phe
            20                  25                  30

Asn Cys


<210> SEQ ID NO 33
<211> LENGTH: 123
<212> TYPE: DNA
<213> ORGANISM: Artificial Sequence
<220> FEATURE:
<223> OTHER INFORMATION: Computer generated

<400> SEQUENCE: 33

atgaccaacc agccgactga gattgcgatt gttggaggtg gaatggtggg tggcgcactc      60

gcgctgggct tggcacagca cggattcgcg gtgacggtga ttgagcatgc tgagccagcc     120

cct                                                                   123


<210> SEQ ID NO 34
<211> LENGTH: 132
<212> TYPE: DNA
<213> ORGANISM: Artificial Sequence
<220> FEATURE:
<223> OTHER INFORMATION: Computer generated

<400> SEQUENCE: 34

atgcacgctg atcttgtgat tgttggagct ggaatggtgg gttccgcact cgcgctggcc      60

ttggaaggtt cgggattgga ggtgttgttg gttgatggtg gttctcttga tgttgcccct     120

tttaaaccag ag                                                         132


<210> SEQ ID NO 35
<211> LENGTH: 132
<212> TYPE: DNA
<213> ORGANISM: Artificial Sequence
<220> FEATURE:
<223> OTHER INFORMATION: Computer generated

<400> SEQUENCE: 35

atgcacgctg atcttgtgat tgttggagct ggaatggtgg gttccgcact cgcgctggcc      60

ttggaaggtt cgggattgga ggtgttgttg gttgatggtg gttctcttga tgttgcccct     120

tttaaaccag ag                                                         132


<210> SEQ ID NO 36
<211> LENGTH: 126
<212> TYPE: DNA
<213> ORGANISM: Artificial Sequence
<220> FEATURE:
<223> OTHER INFORMATION: Computer generated

<400> SEQUENCE: 36
```

-continued

```
atgaccaacc agccgactga gattgcgatt gttggaggtg gaatggtggg tggcgcactc     60

gcgctgggct tggcacagca cggattcacg gtgacggtga ttgagcatgc tgagccagcc    120

cctttt                                                               126


<210> SEQ ID NO 37
<211> LENGTH: 126
<212> TYPE: DNA
<213> ORGANISM: Artificial Sequence
<220> FEATURE:
<223> OTHER INFORMATION: Computer generated

<400> SEQUENCE: 37

atggacgtta tccagaagga tatgatcgtt gttggaggtg gaatggtggg tgccgcatgc     60

gcgctgggct tgggaaagca gggacaccag gtgcagttga ttgagcatgc tcctcttccc    120

cagttt                                                               126


<210> SEQ ID NO 38
<211> LENGTH: 126
<212> TYPE: DNA
<213> ORGANISM: Artificial Sequence
<220> FEATURE:
<223> OTHER INFORMATION: Computer generated

<400> SEQUENCE: 38

atgaccaacc agccgactga gattgcgatt gttggaggtg gaatggtggg tggcgcactc     60

gcgctgggct tggcacagca cggattcgcg gtgacggtga ttgagcatgc tgagccagcc    120

cctttt                                                               126


<210> SEQ ID NO 39
<211> LENGTH: 19
<212> TYPE: PRT
<213> ORGANISM: Artificial Sequence
<220> FEATURE:
<223> OTHER INFORMATION: Computer generated

<400> SEQUENCE: 39

Met Leu Cys Glu Lys Ala Ser Thr Trp Lys His Met Cys Phe Cys Tyr
 1               5                  10                  15

Phe Asn Cys


<210> SEQ ID NO 40
<211> LENGTH: 69
<212> TYPE: DNA
<213> ORGANISM: Artificial Sequence
<220> FEATURE:
<223> OTHER INFORMATION: Computer generated

<400> SEQUENCE: 40

atgcagaccc tatcgattca acacgggacc ttggtcacaa actgtgctga agcagtccgc     60

agtggtatc                                                             69


<210> SEQ ID NO 41
<211> LENGTH: 20
<212> TYPE: DNA
<213> ORGANISM: Artificial Sequence
<220> FEATURE:
<223> OTHER INFORMATION: Computer generated

<400> SEQUENCE: 41

atgcagaccc tatgtttatc                                                 20
```

-continued

```
<210> SEQ ID NO 42
<211> LENGTH: 67
<212> TYPE: DNA
<213> ORGANISM: Artificial Sequence
<220> FEATURE:
<223> OTHER INFORMATION: Computer generated

<400> SEQUENCE: 42

tggaaccagt gttacctggt catggcagcc cagaacccac tgtcaaccca tgtacaagtc     60

cccatag                                                               67
```